United States Patent
Hata et al.

(10) Patent No.: US 11,051,892 B2
(45) Date of Patent: Jul. 6, 2021

(54) CONTROL APPARATUS AND TENDON-DRIVEN DEVICE

(71) Applicants: CANON U.S.A., INC., Melville, NY (US); The Brigham and Women's Hospital, Inc, Boston, MA (US)

(72) Inventors: Nobuhiko Hata, Newton, MA (US); Takahisa Kato, Brookline, MA (US); Ichiro Okumura, Abiko (JP); Kiyoshi Takagi, Tokyo (JP); Hidekazu Kose, Atlanta, GA (US)

(73) Assignees: Canon U.S.A., Inc., Melville, NY (US); The Brigham and Women's Hospital, Inc., Boston, MA (US)

( * ) Notice: Subject to any disclaimer, the term of this patent is extended or adjusted under 35 U.S.C. 154(b) by 1017 days.

(21) Appl. No.: 14/491,796

(22) Filed: Sep. 19, 2014

(65) Prior Publication Data

US 2015/0088161 A1 Mar. 26, 2015

Related U.S. Application Data

(60) Provisional application No. 61/880,692, filed on Sep. 20, 2013, provisional application No. 61/935,677, filed on Feb. 4, 2014.

(51) Int. Cl.
*A61B 1/00* (2006.01)
*A61B 1/005* (2006.01)
(Continued)

(52) U.S. Cl.
CPC ............ *A61B 34/30* (2016.02); *A61B 1/0016* (2013.01); *A61B 1/0055* (2013.01);
(Continued)

(58) Field of Classification Search
CPC ..... A61B 19/2203; A61B 34/30; A61B 34/71; A61B 1/0016; A61B 1/0055; A61B 1/0057
(Continued)

(56) References Cited

U.S. PATENT DOCUMENTS

| 4,686,963 | A | | 8/1987 | Cohen et al. | |
|---|---|---|---|---|---|
| 5,297,443 | A | * | 3/1994 | Wentz | B25J 15/12 |
| | | | | | 74/490.04 |

(Continued)

FOREIGN PATENT DOCUMENTS

| EP | 0659387 A1 | 6/1995 |
|---|---|---|
| EP | 2289592 A2 | 3/2011 |

(Continued)

OTHER PUBLICATIONS

Butler EJ et al.;"Robotic Neuro-Endoscope with Concentric Tube Augmentation;" IEEE/RSJ Intternational Conference on Intelligent Robots and Systems; Oct. 7-12, 2012; pp. 2941-2946.

(Continued)

*Primary Examiner* — Timothy J Neal
*Assistant Examiner* — William B Chou
(74) *Attorney, Agent, or Firm* — Canon U.S.A., Inc. IP Division

(57) ABSTRACT

An apparatus including a tendon-driven device such as an endoscope comprising a bendable body, a tendon attached to and extending a length of said body, and an actuator that will actuate said tendon based on a control signal from a controller. The controller is configured to send said control signal to said actuator and comprises a forward-kinematic-mapping unit that estimates an angular displacement, wherein the kinematic-mapping unit is configured for: providing a tension value of the tendon to obtain a desired angular displacement wherein the tension has a nonlinear (Continued)

relationship with the desired angular displacement based on information of friction where the tension is greater that would be calculated without including the effect of friction. The friction coefficient may be determined as it changes over time.

25 Claims, 41 Drawing Sheets

(51) Int. Cl.
*A61B 34/30* (2016.01)
*A61B 34/00* (2016.01)
*A61B 17/00* (2006.01)

(52) U.S. Cl.
CPC ............ *A61B 1/0057* (2013.01); *A61B 34/71* (2016.02); *A61B 2017/00323* (2013.01); *A61B 2034/301* (2016.02)

(58) Field of Classification Search
USPC ................ 600/109, 117, 139, 140–152, 160
See application file for complete search history.

(56) References Cited

U.S. PATENT DOCUMENTS

| | | | |
|---|---|---|---|
| 5,469,254 A | 11/1995 | Konomura | |
| 6,733,458 B1* | 5/2004 | Steins | A61B 8/0833 600/461 |
| 6,858,005 B2 | 2/2005 | Ohline et al. | |
| 7,591,783 B2 | 9/2009 | Boulais et al. | |
| 7,752,920 B2 | 7/2010 | Blumenkranz et al. | |
| 7,785,252 B2 | 8/2010 | Danitz et al. | |
| 7,850,642 B2 | 12/2010 | Moll et al. | |
| 7,855,712 B2 | 12/2010 | Powers et al. | |
| 7,914,466 B2 | 3/2011 | Davis et al. | |
| 8,125,755 B2 | 2/2012 | Garcia et al. | |
| 8,219,246 B2 | 7/2012 | Buckingham et al. | |
| 8,347,757 B2 | 1/2013 | Duval | |
| 8,348,861 B2 | 1/2013 | Glozman et al. | |
| 8,394,054 B2 | 3/2013 | Wallace et al. | |
| 8,403,833 B2 | 3/2013 | Umemoto | |
| 8,412,378 B2 | 4/2013 | Abdallah et al. | |
| 8,424,941 B2 | 4/2013 | Ihrke et al. | |
| 8,578,810 B2 | 11/2013 | Donhowe | |
| 9,144,370 B2 | 9/2015 | Kato et al. | |
| 9,282,993 B1* | 3/2016 | Cohen | A61B 17/3421 |
| 2003/0045778 A1 | 3/2003 | Ohline et al. | |
| 2004/0138525 A1 | 7/2004 | Saddat et al. | |
| 2005/0131279 A1 | 6/2005 | Boulais et al. | |
| 2006/0015010 A1* | 1/2006 | Jaffe | A61B 1/0008 600/114 |
| 2007/0219581 A1 | 9/2007 | Dohi et al. | |
| 2008/0039715 A1 | 2/2008 | Wilson et al. | |
| 2008/0221592 A1 | 9/2008 | Kawai | |
| 2008/0281293 A1 | 11/2008 | Peh et al. | |
| 2008/0287741 A1 | 11/2008 | Ostrovsky et al. | |
| 2009/0012533 A1 | 1/2009 | Barbagli et al. | |
| 2009/0093712 A1* | 4/2009 | Busch | A61B 5/06 600/424 |
| 2009/0095112 A1 | 4/2009 | Buckingham et al. | |
| 2010/0010298 A1 | 1/2010 | Bakos et al. | |
| 2010/0168721 A1 | 7/2010 | Rogers et al. | |
| 2010/0300230 A1 | 12/2010 | Helmer | |
| 2011/0196199 A1 | 8/2011 | Donhowe et al. | |
| 2011/0224688 A1 | 9/2011 | Larkin et al. | |
| 2011/0251519 A1 | 10/2011 | Romoscanu | |
| 2011/0257480 A1 | 10/2011 | Takahashi et al. | |
| 2011/0319910 A1 | 12/2011 | Roelle et al. | |
| 2012/0046522 A1 | 2/2012 | Naito | |
| 2012/0065628 A1 | 3/2012 | Naito | |
| 2012/0071752 A1 | 3/2012 | Sewell | |
| 2012/0078053 A1 | 3/2012 | Phee et al. | |
| 2012/0123200 A1 | 5/2012 | Rogers | |
| 2012/0123441 A1 | 5/2012 | Au et al. | |
| 2012/0136381 A1 | 5/2012 | Morrison et al. | |
| 2012/0203142 A1 | 8/2012 | Bedell | |
| 2012/0265220 A1* | 10/2012 | Menn | A61B 17/1285 606/142 |
| 2012/0271109 A1 | 10/2012 | Belson | |
| 2013/0085333 A1 | 4/2013 | Ramamurthy et al. | |
| 2013/0090763 A1 | 4/2013 | Simaan et al. | |
| 2013/0165945 A9 | 6/2013 | Roelle et al. | |
| 2013/0197539 A1 | 8/2013 | Simaan et al. | |
| 2013/0218005 A1 | 8/2013 | Desai et al. | |
| 2013/0231679 A1 | 9/2013 | Wallace et al. | |
| 2014/0243592 A1 | 8/2014 | Kato et al. | |
| 2015/0164596 A1 | 6/2015 | Ramo et al. | |
| 2017/0304014 A1* | 10/2017 | Au | A61B 34/30 |

FOREIGN PATENT DOCUMENTS

| | | |
|---|---|---|
| EP | 2471437 A1 | 7/2012 |
| JP | 2000-279376 A | 10/2000 |
| JP | 2002-264048 A | 9/2002 |
| JP | 2005-059110 A | 3/2005 |
| WO | 2007/141784 A2 | 12/2007 |
| WO | 2009097461 A1 | 8/2009 |
| WO | 2012/054829 A2 | 4/2012 |
| WO | 2013/026012 A1 | 2/2013 |
| WO | 2011/062079 A1 | 4/2013 |
| WO | 20141134475 A1 | 9/2014 |

OTHER PUBLICATIONS

Camarillo DB, et al.; "Configuration Tracking for Continuum Manipulators With Coupled Tendon Drive;" IEEE Transactions on Robotics; vol. 25, No. 4; Aug. 2009; pp. 798-808.

Chiang, LS et al., "Tendon Sheath Analysis for Estimation of Distal End Force and Elongation ;" 2009 IEE/ASME Intl. Conf. on Advanced Intelligent Mechatronics, Singapore, Jul. 14-17, 2009; pp. 332-337.

Hannan, M. W. and Walker, I. D.; "Kinematics and the Implementation of an Elephant's Trunk Manipulator and Other Continuum Style Robots;" Journal of Robotic Systems, 20(2), 45-63 (2003); DOI: 10.1002/rob.10070 ; (2003); pp. 45-63.

Jones, B.A.; "Kinematics for Multisection Continuum Robots;" IEEE Transactions on Robotics; vol. 22, No. 1; Feb. 2006; pp. 43-55.

Kato T, Okumura I, Song SE, Hata N.; "Multi-section continuum robot for endoscopic surgical clipping of intracranial aneurysms.;" Med Image Comput Comput Assist Interv.; 2013; 16(01): 364-371.

Neppallii et al.; "Closed-Form Inverse Kinematics for Continuum Manipulators;" Advanced Robotics 23 (2009) 2077-2091.

Phee, SJ et al., "Tendon Sheath Analysis for Estimation of Distal End Force and Elongation for Sensorless Distal End;" Robotica: p. 1-10, 2010.

Webster RJ III, et al.; "Design and Kinematic Modeling of Constant Curvature Continuum Robots: A Review;" International Journal of Robotics Research. 2010; 29(13):1661-1683.

Weiss, JA and JC Gardiner; "Computational Modeling of Ligament Mechanics;" Critical Review in Biomedical Engineering 29(4):1-70 (2001).

Yoon HS et al.; "Active Bending Endoscope Robot System for Navigation through Sinus Area;" IROS, 2011 IEE/RSJ Intl Conf; Sep. 25-30, 2011; pp. 967-972.

Yoshimitsu K Kato T, Song SE, Hata N.; "A novel four-wire-driven robotic catheter for radio-frequency ablation treatment;" Int J Comput Assist Radiol Surg. ; Sep. 2014; 9(5): 867-874. doi:10.1007/s11548-014-0982-3.

Gupta, S. et al, "Using a Coaxial Technique with a Curved Inner Needle for CT-Guided Fine-Needle Aspirationb Biopsy", Technical Innovation, AJR:179, Jul. 2002, pp. 109-112.

Singh, A.K., et al, "Core Biopsy with Curved Needle Technique", Vascular and Interventional Radiology, Clinical Observations, AJR:191, Dec. 2008, pp. 1745-1750.

(56) References Cited

OTHER PUBLICATIONS

Phee, S.J., et al, "Tendon sheath analysis for estimation of distal end force and enlongation for sensorless distal end", Robotics, 2010, Cambridge University Press.
Butler, E. J., et al, "Robotic Neuro-Endoscope with Concentric Tube Augmentation", IEEE/RSJ International Conference on Intelligent Robots and Systems, Oct. 7-12, 2012, pp. 2941-2946.
Amarillo, D.B., et al, "Configuration Tracking for Contiuum Manipulators with Coupled Tendon Drive", IEEE Transactions on Robotics, Aug. 2009, pp. 798-808, vol. 25, No. 4, with Abstract.
Chiang, L.S., et al, "Tendon Sheath Analysis for Estimation of Distal End Force and Elongation", IEEE/ASME International Conference on Advanced Intelligent Mechatroincs, Jul. 14-17, 2009, pp. 332-337.
Yoon, H., et al, "Active Bending Endoscopy Robot System for Navigation through Sinus Area", IEEE/RSJ International Conference on Intelligent Robots and Systems, Sep. 25-30, 2011, pp. 967-972.
Weiss, J.A., et al, "Computational Modeling of Ligament Mechanics", Critical Reviews™ in Biomedical Engineering, 2001, pp. 1-70, vol. 29, No. 4.

\* cited by examiner

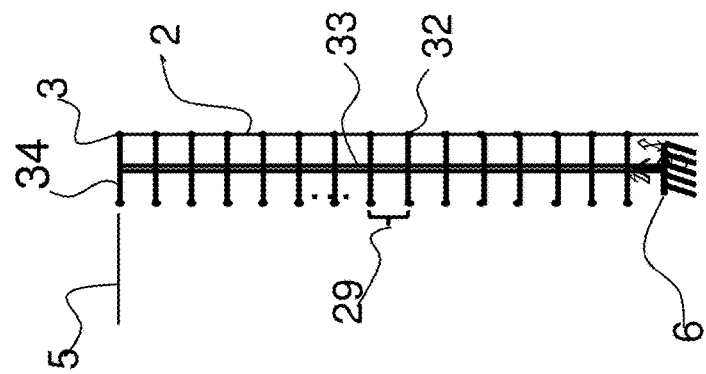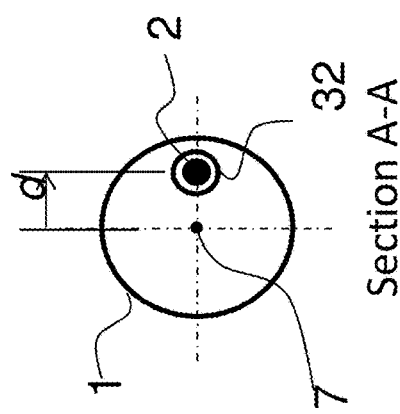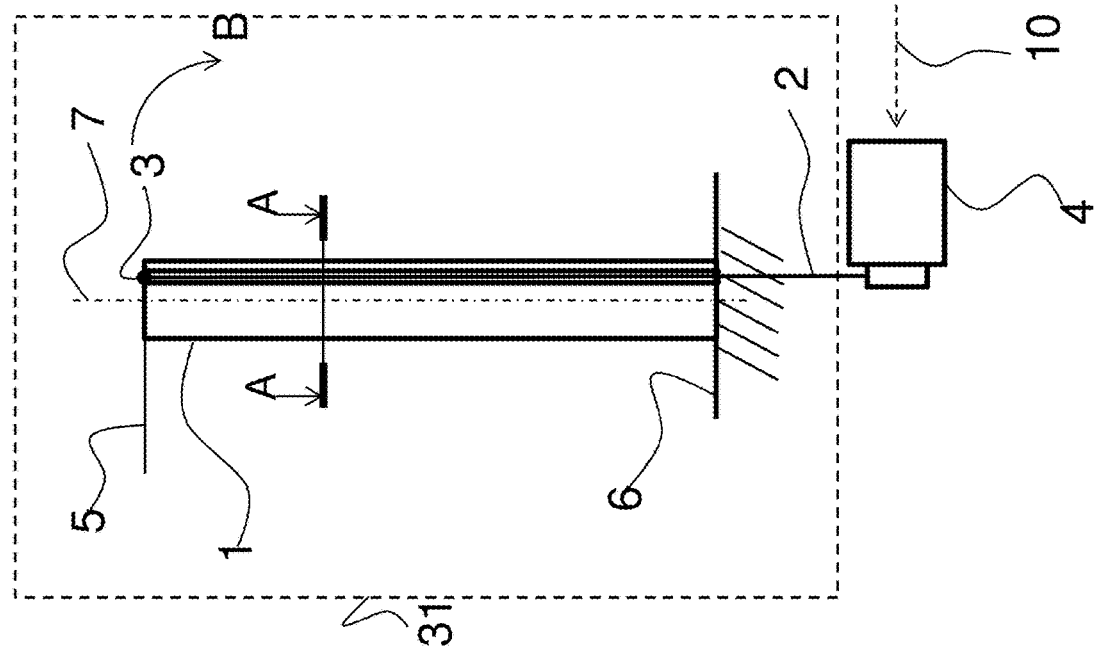

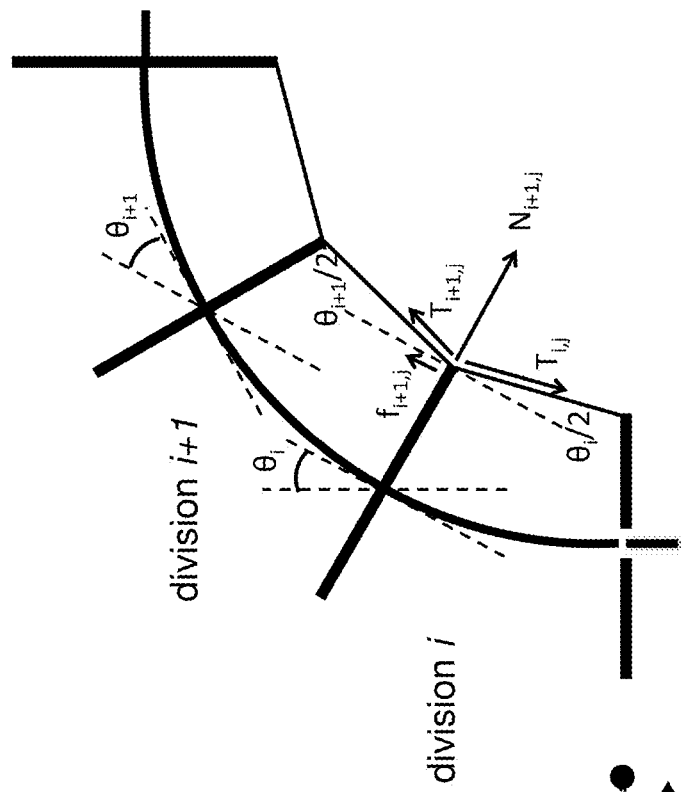
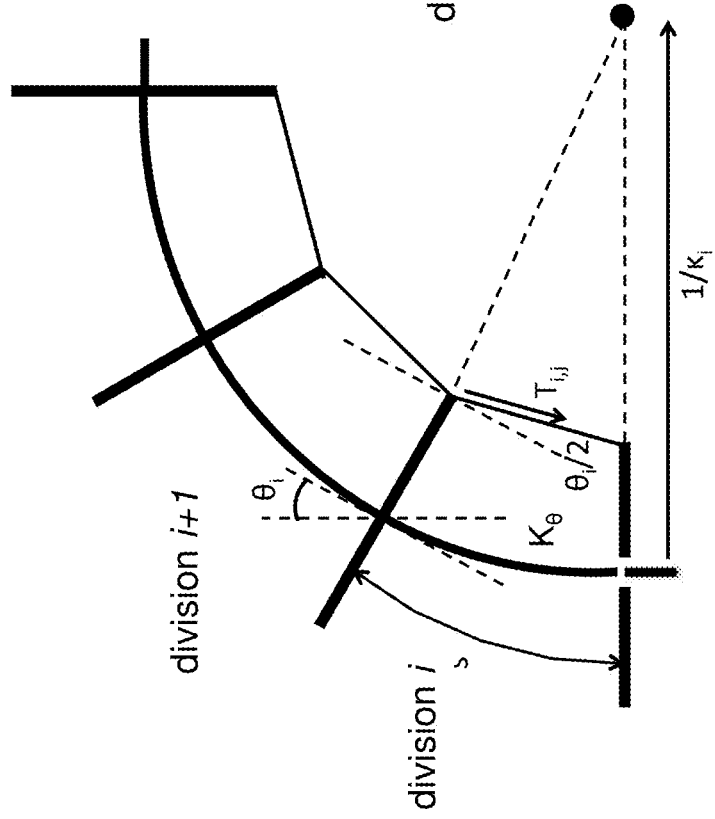
Fig. 2(a)
Fig. 2(b)

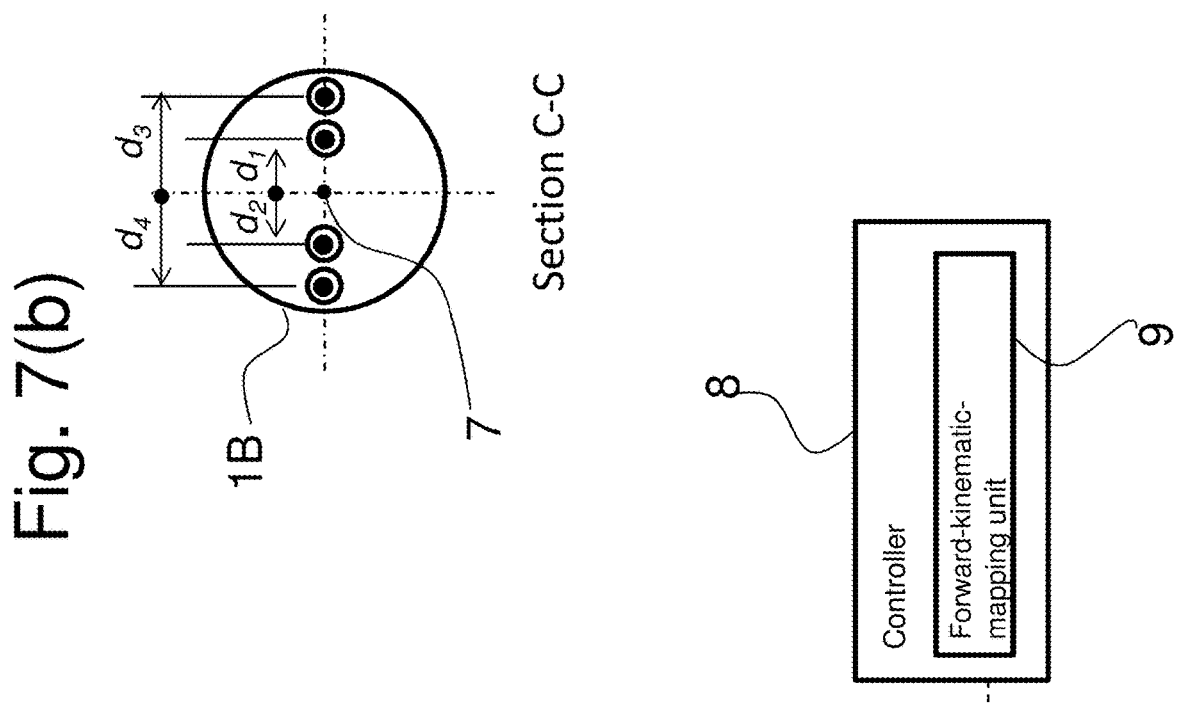
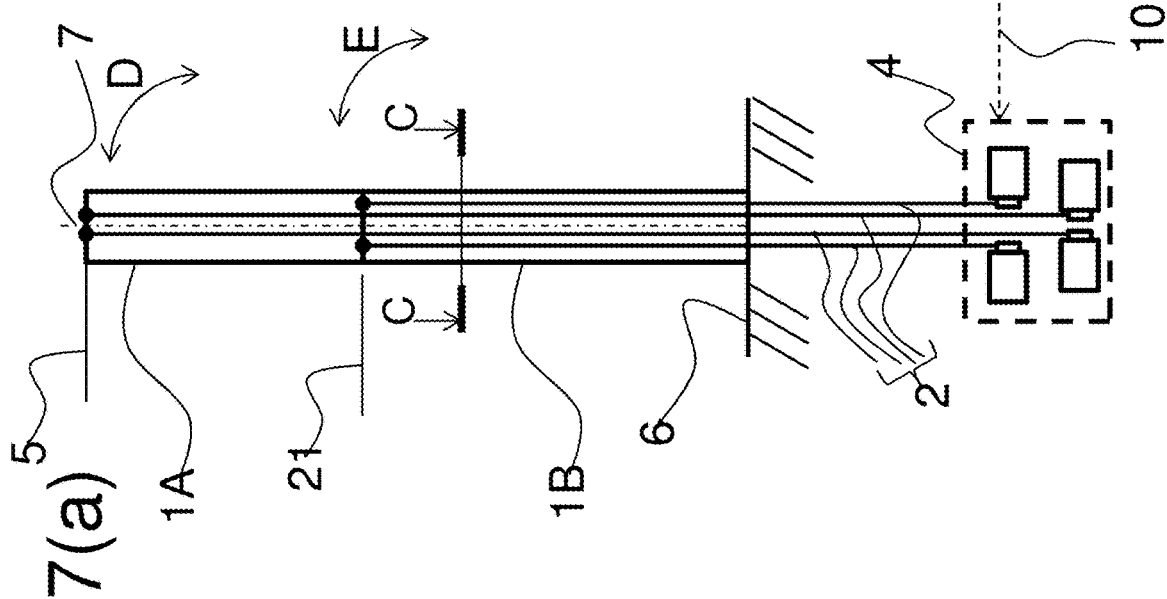

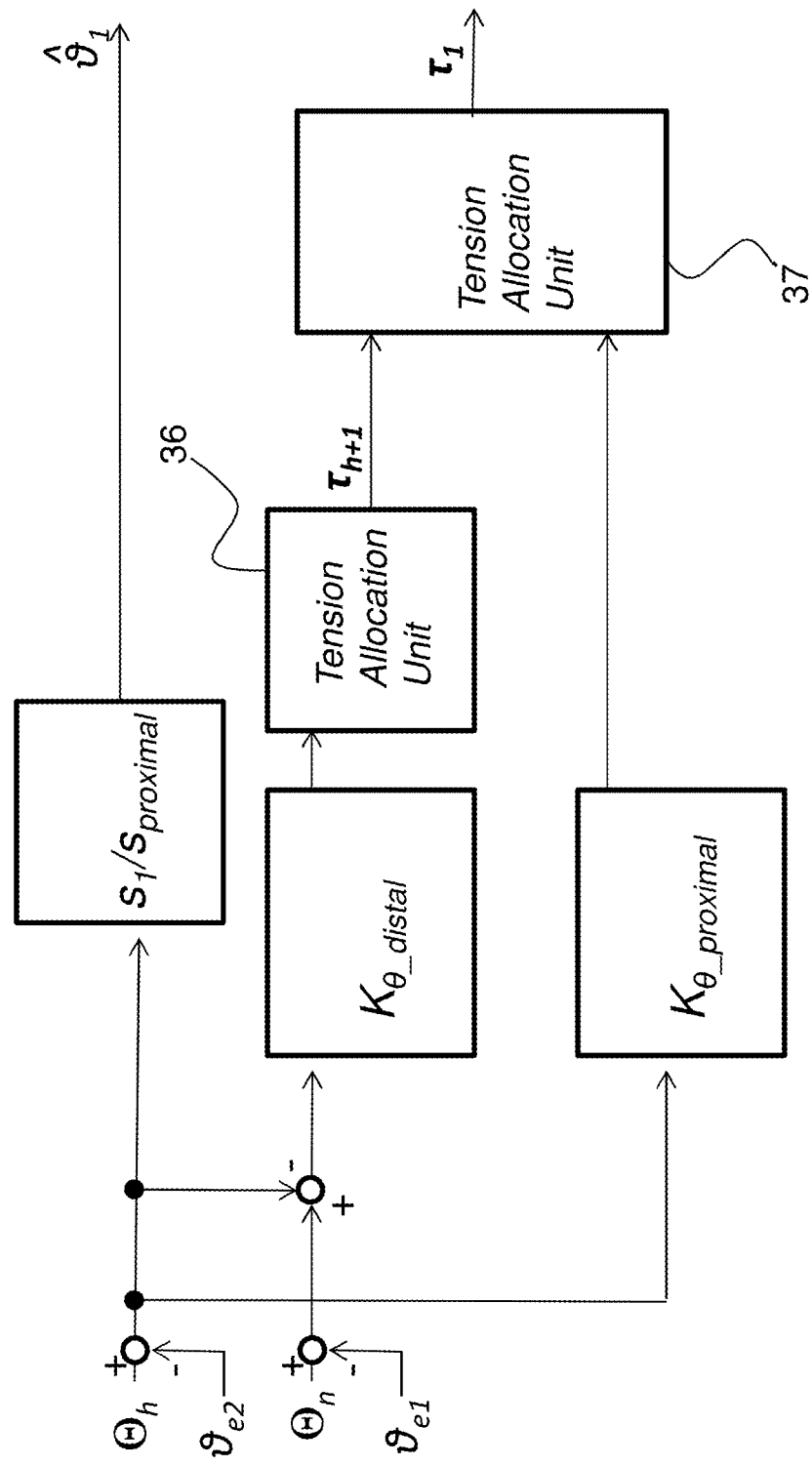

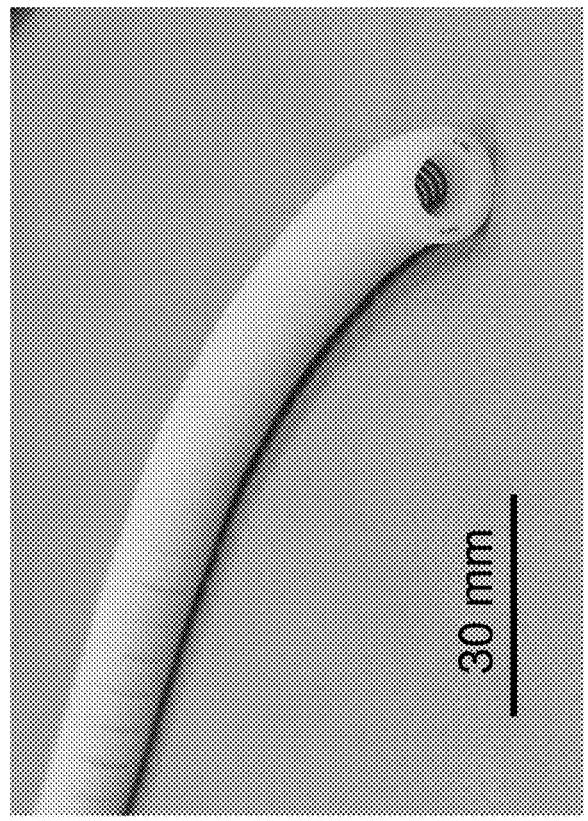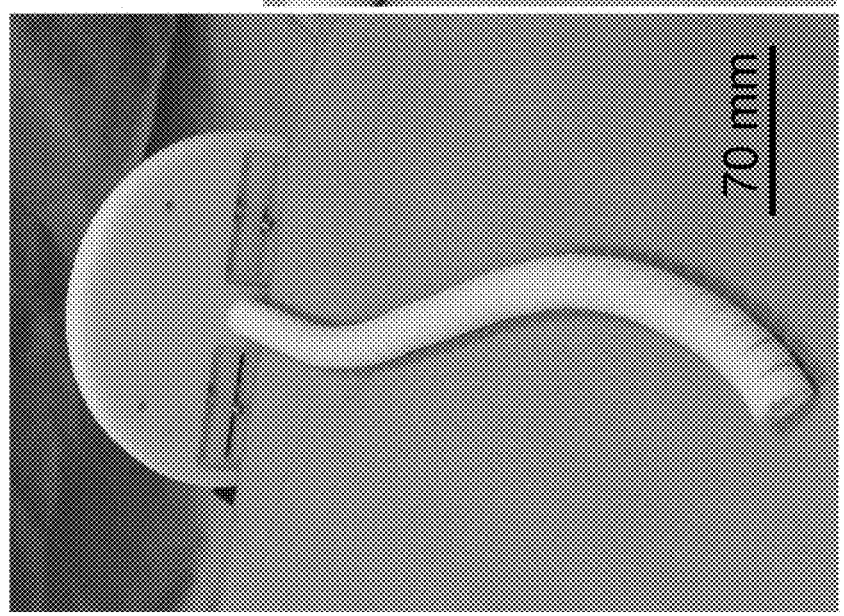

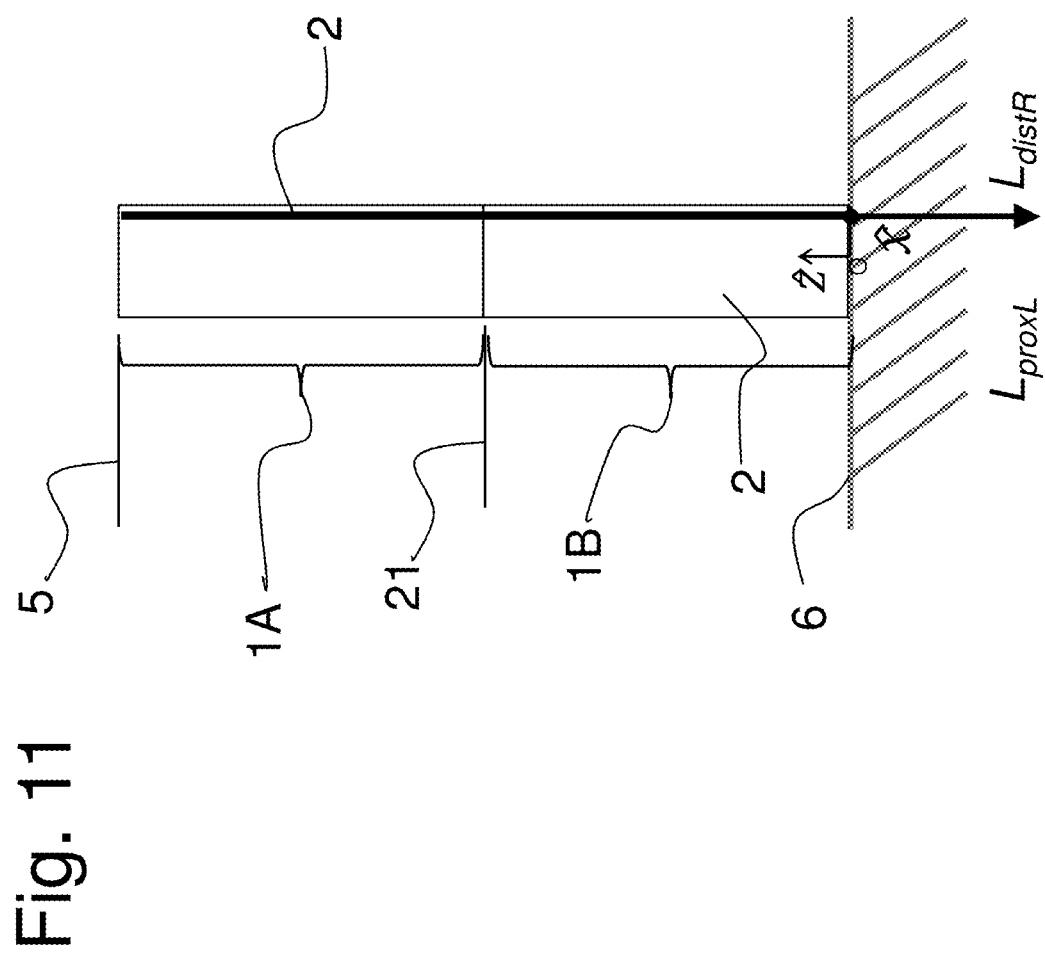

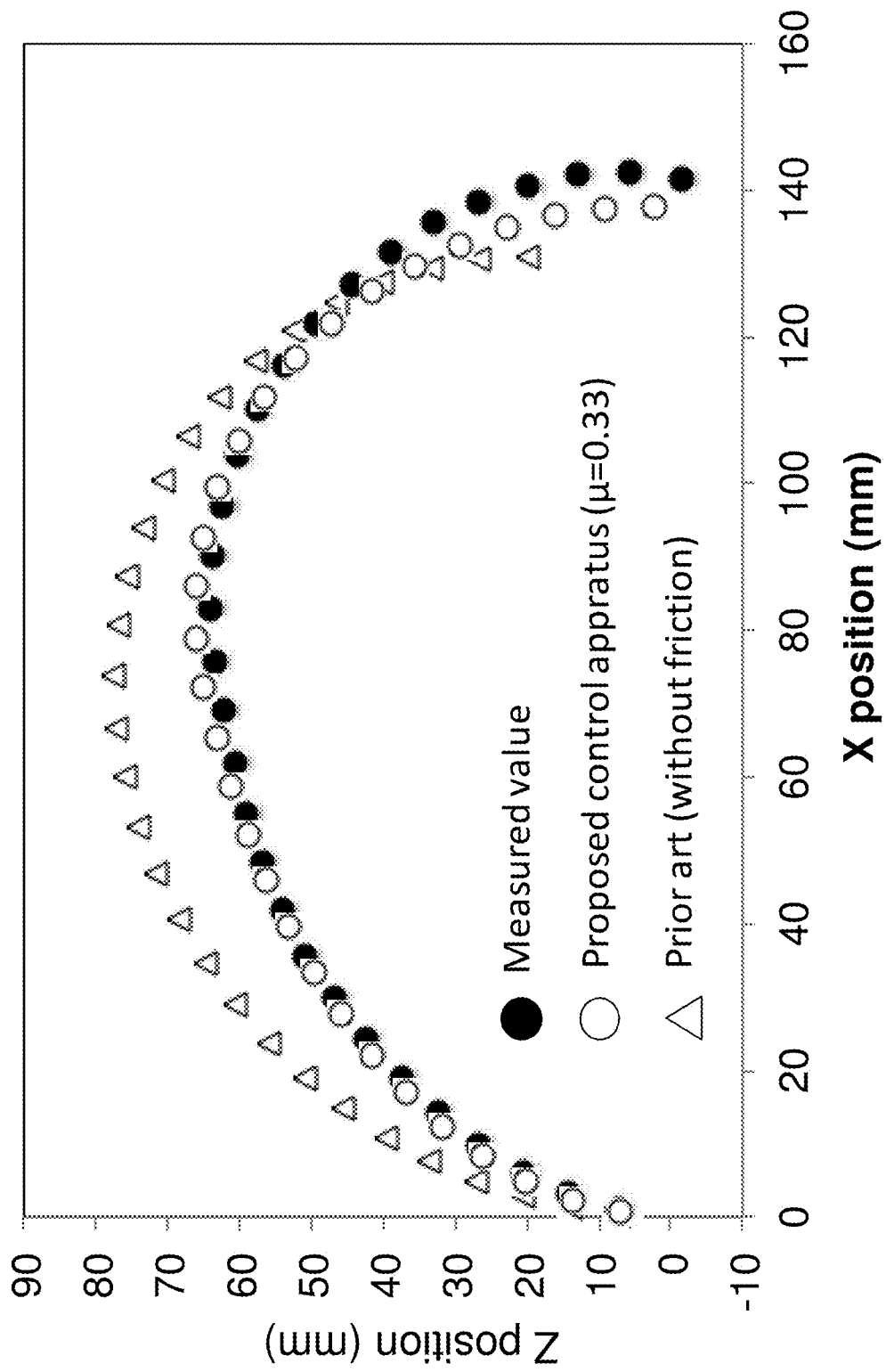

A

B

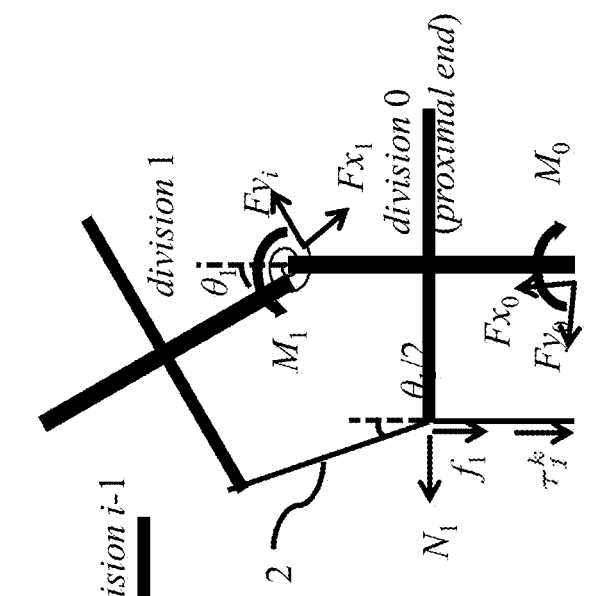
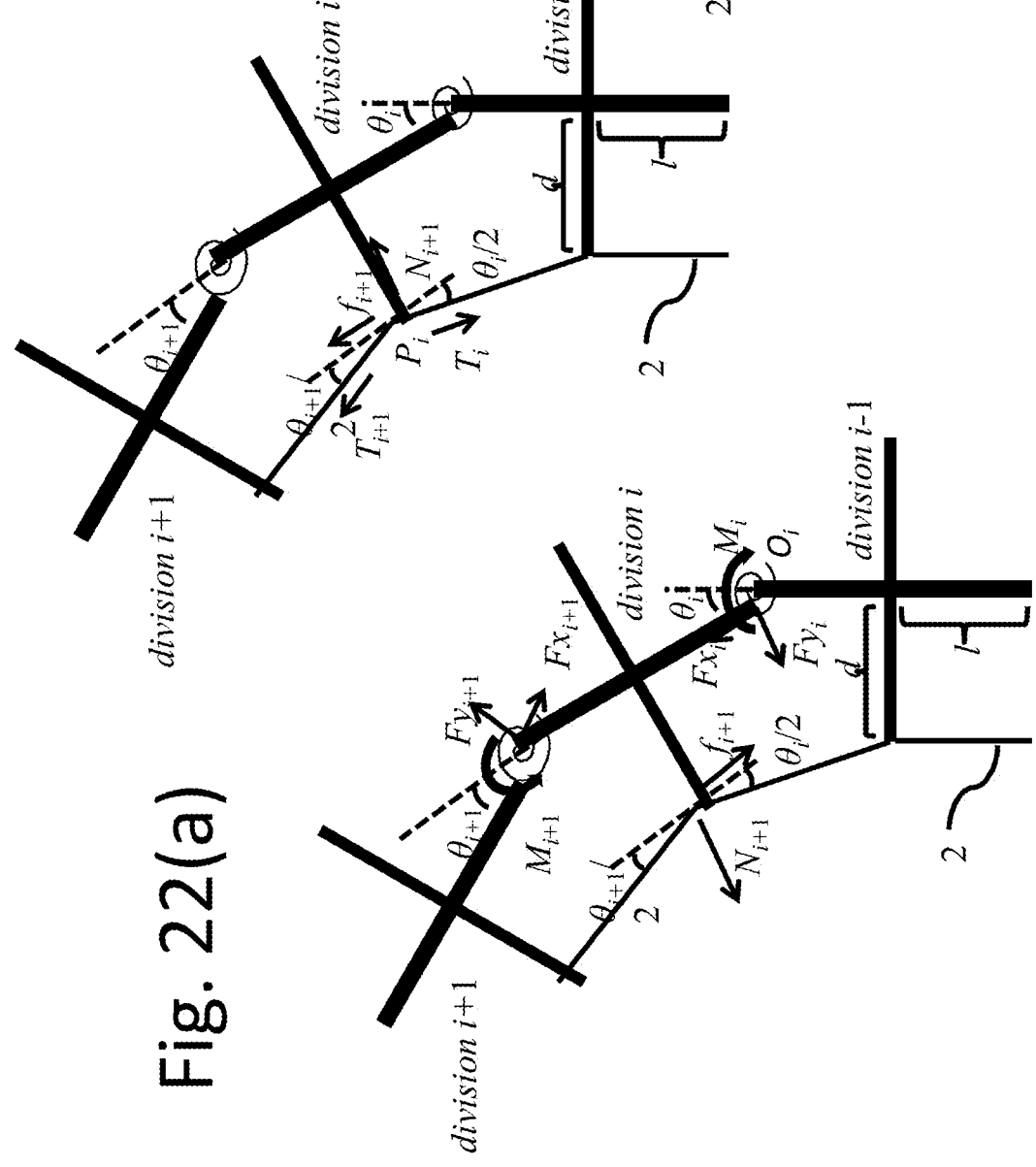
Fig. 22(a) Fig. 22(b) Fig. 22(c)

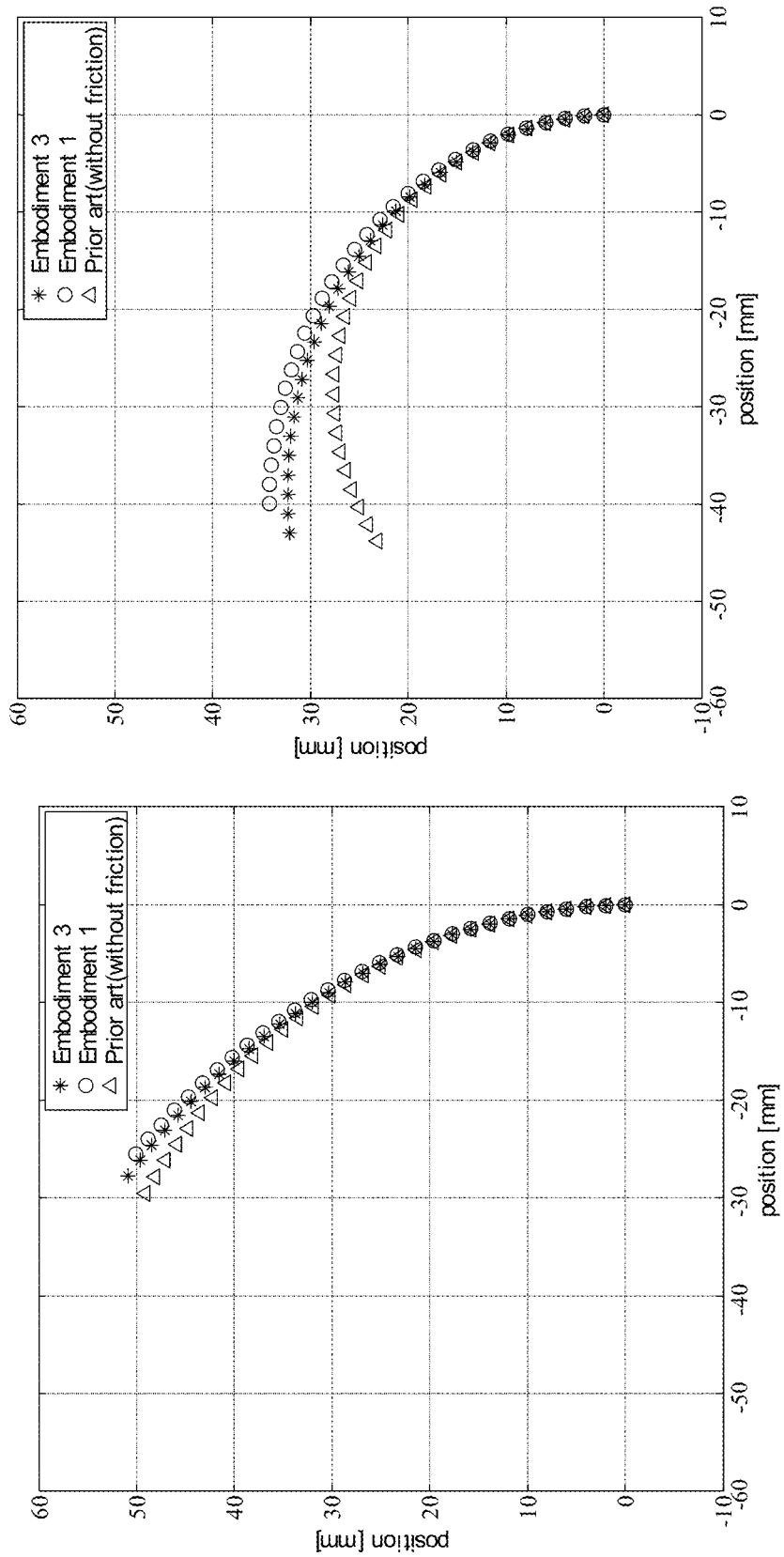

CONTROL APPARATUS AND TENDON-DRIVEN DEVICE

CROSS-REFERENCE TO RELATED APPLICATIONS

This application claims priority from Provisional Application No. 61/880,692 filed 20 Sep., 2013 and Provisional Application No. 61/935,677 filed 4 Feb. 2014, the disclosure of which are both hereby incorporated by reference herein in their entireties.

FIELD OF THE INVENTION

This application relates generally to medical devices and in particular to an articulated device applicable to remote robotic manipulation of surgical tools and instruments, such as endoscopes.

BACKGROUND

Endoscopic surgical instruments and tools are well known and continue to gain acceptance in the medical field. An endoscopic instrument or tool generally includes a rigid or flexible tube commonly referred to as a sleeve or sheath. One or more tool channels extend along (typically inside) the sheath to allow access to end effectors located at a distal end of the sheath. Control mechanisms located at a proximal end of the sheath are configured to enable remote manipulation of the end effectors via the one or more tool channels. Accordingly, the control apparatus for the sheath plays a key role in ensuring flexible access to end effectors, while protecting delicate organs and tissues of a patient. As used herein and elsewhere in the art of endoscopic medical devices, the term "end effector" refers to the actual working part of a surgical instrument or tool.

Endoscopic surgical tools may include clamps, graspers, scissors, staplers, needle holders, and other like tools, which serve to manipulate body parts (organs or tissue) during examination or surgery. Endoscopic instruments primarily include a light delivery system which serves to illuminate a body part under inspection, and an imaging system which serves to observe the body part under inspection. In a typical endoscopic light delivery system, the light source is located outside the patient's body and the light is delivered via an optical fiber system. In an endoscopic imaging system, an objective lens located at the distal end of the sheath transmits the image, formed by collected light, via a bundle of optical fibers to a viewing device or sensor located at the proximal end of the sheath. An example of a surgical endoscopic instrument includes a laparoscope, but many more exist.

Current endoscopic technology endeavors to reduce the amount of negative side effects and increase patient comfort, by providing minimally invasive surgery (MIS). However, one of the major shortcomings in the current state of the art of endoscopic tools is the lack of dexterity and sensitivity offered to health professionals (endoscopists and surgeons) who perform endoscopic procedures.

In highly delicate surgical operations, such as neurosurgery, it is necessary to avoid the contact of endoscope or any other surgical tools with the critical brain tissues and nerves in the periphery of the lesion. To that end, it is necessary to maneuver with precisely controlled shape of the sheath and to know with a high degree of certainty how much force or tension is being applied to an end effector. It is also necessary to view in detail the lesion from various directions, often even from an opposite direction from which the endoscope is inserted. In this manner, the operation can be performed without damaging delicate structures located near the organ or tissue being operated. To that end, it is necessary to be able to easily bend the sheath to a controlled shape in all directions and in any location, without exerting excessive force.

Many conventional endoscopic instruments with rigid or flexible sheaths prevent the surgeon or endoscopist from easily maneuvering endoscopic tools and instruments due to the rigidity of the mechanical structure of the sheath.

A potential solution to overcome the above-mentioned issues is to use a robotized articulation device to drive the endoscope camera in order to attain better view of the surgical lesion with minimal invasion to the surrounding critical structure under accurate control by a control apparatus. Improved instrumentation (e.g. endoscopes and catheters) using the robotized articulation device has been an area of active interest in clinical and engineering research groups.

A first approach is a device that uses a concentric tube. The concentric-tube robot is composed of precurved elastic tubes arranged in a concentric fashion. To control this robot with multi-sections, these tubes are rotated and translated with respect to one another. Bending torques are "built-in" as precurved tubes and are transmitted by rotational and translational motion of tubes. A second approach uses a multi-backbone robot in push-pull actuation. Among multiple backbones, one primary backbone is centrally located and is attached to a base disk and an end disk. The secondary backbones attached to the end disk are equidistant from each other. To generate bending torques, the secondary backbones are pushed and pulled against a base disk. These multi-section robots have been proposed to be applied to skull-based surgeries, neuro-endoscopes for endoscopic third ventriculostomy and choroid plexus cauterization, single-port surgery and transurethral surveillance and interventions.

Another type of robotized articulation device is a tendon-driven continuum robot. This approach has passive compliance when tendons are held by appropriate tensions. This feature ensures increased safety for patients in the case of high risk of contact with anatomies. An example includes a tendon-driven steerable catheter. For independent control of multi-sections, a linear beam configuration model that transforms beam configuration to tendon displacement including both mechanical and geometrical coupling among multi-sections has been proposed.

However, the tendon-driven continuum robot needs further refinement before becoming applicable to endoscopic support. The current state of the art in control and trajectory planning of the tendon-driven robot assumes that the one bending unit, or section, has constant curvature throughout the multiple sections as the pulling force propagates constantly through sections. In reality, a friction force between tendons and their guide structures within a section reduces the propagating pulling force, thus lessening the curvature from the proximal to the distal end of the robot. Limitation in size and material selection prohibits the reduction of this friction force, making it unrealistic to ignore friction force in control and trajectory planning.

Thus, there is a need to incorporate friction in kinematic mapping and extend such control and trajectory planning to develop a flexible endoscope. This is particularly useful as a neuroendoscope for surgical clipping of intracranial aneurysms.

Furthermore, there is a need to attain the control apparatus for tendon-driven devices with a feed-forward-control system with the kinematic mapping considering salient features of friction in tendons so that the control apparatus can generate control signal with high control bandwidth accurately.

SUMMARY

According to at least one embodiment of the invention, there is provided an apparatus comprising a tendon-driven device having a proximal end fixed mechanically and a distal end, comprising: a bendable body, and a tendon attached to and extending a length of said body. For calculation purposes, the tendon-driven device can be understood as divided into multiple divisions between said distal end and said proximal end. The apparatus further comprises an actuator connected to said tendon, configured to actuate said tendon based on a control signal; and a controller configured to send said control signal to said actuator, comprising a forward-kinematic-mapping unit that estimates an angular displacement at the distal end, wherein the kinematic-mapping unit is configured for: providing a tension value of the tendon to obtain a desired angular displacement at the distal end of said tendon-driven device, wherein the tension has a nonlinear relationship with the desired angular displacement, and wherein the relationship is based on information of friction between said tendon and said body and the tension is greater that would be calculated without including the effect of friction.

In some embodiments, the kinematic-mapping unit is configured to map tension to curvature for a first division at the proximal end of said tendon-driven device from information of friction between said tendon and said first division and angular displacement of the first division; propagate a tension ratio between adjacent divisions of said tendon-driven device from the tension of the more proximally located division and from information of friction between said tendon and said division and angular displacements of the adjacent divisions; and estimate the angular displacement in said divisions from said tension ratio.

In other embodiments, there is provided an apparatus as well as a method for inverse kinematic mapping for the multi-section tendon-driven robot. The method comprising using a vectorized tension propagation model as disclosed herein. For example, the inverse kinematic mapping is applied to a two-section tendon-driven robot with a prismatic joint to generate reference trajectories with wide range of combination of directions and locations in the robot workspace.

Further embodiments, which may be combined with other various embodiments, include updating the friction coefficient. Yet other embodiments that may be combined with other various embodiments include providing less approximation and more precise attitude estimation by additional calculations.

Additional embodiments include an endoscopic apparatus. Further features of the present invention will become apparent from the following description of exemplary embodiments with reference to the attached drawings.

BRIEF DESCRIPTION OF DRAWINGS

Further objects, features and advantages of the present invention will become apparent from the following detailed description when taken in conjunction with the accompanying figures showing illustrative embodiments of the present invention.

FIG. 1(a) illustrates an exemplary control apparatus for a tendon-driven device according to a first embodiment. FIG. 1(b) is a cross-sectional view along line A-A shown in FIG. 1(a). FIG. 1(c) illustrates a lamped-parameter model for the tendon-driven device illustrated in FIG. 1(a).

FIG. 2 (FIGS. 2(a) and 2(b)) illustrates the relationship of combining angular displacements for divisions.

FIG. 3 illustrates an exemplary control apparatus according to the first embodiment. More specifically.

FIG. 4 illustrates another example of a control apparatus according to the first embodiment. More specifically.

FIG. 5 illustrates another example of a control apparatus according to the first embodiment. More specifically.

FIG. 7(a) illustrates of an exemplary control apparatus according to a second embodiment. FIG. 7(b) is a cross-sectional view along line C-C shown in FIG. 7(a).

FIG. 8 illustrates an exemplary control unit according to the second embodiment. More specifically.

FIG. 9 illustrates an exemplary initial-value-generating unit.

FIGS. 10(a) and 10(b) show an exemplary prototype of the tendon-driven device including a proximal body and a distal body.

FIG. 11 illustrates the two tendons embedded in the prototype.

FIG. 12 illustrates the validation result of the prototype.

FIGS. 14(A) and 13(B) illustrate the relationship of combining angular displacements for the proximal and distal sections of a continuum robot.

FIG. 22 illustrates a coordinates system of a robot according to several embodiments. More specifically, FIG. 22(a) illustrates force and moment acting on division i, and FIG. 22(b) r illustrates force acting on tendon 2 at a point of contact Pi of the division i and tendon 2. FIG. 22(c) illustrates force and moment acting on the proximal end and division 1.

In FIGS. 24(a) and 24(b), the asterisks, circles, and triangles respectively represent response according to the method of the third embodiment, the method of the first embodiment, and the related art where friction is not taken into consideration.

FIGS. 33(a) and 33(b) are charts showing the position error of the extended FKM in mm for each of the 30 cells within an embodied snake robot for tensions between 0.10 N and 0.40 N. The bars signify the mean values of the position error among three trials.

FIG. 34(a) is the arching posture; FIG. 34(b) is the extending posture.

DETAILED DESCRIPTION

Figure 3A:
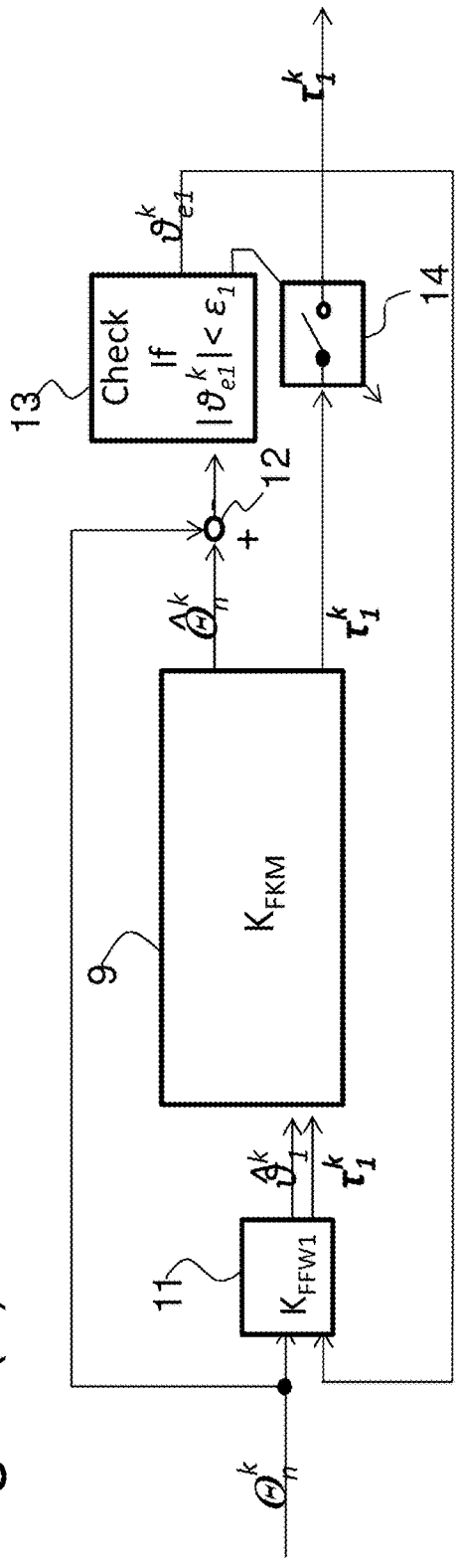
FIG. 3(a) illustrates an exemplary control unit and FIG. 3(b) illustrates an exemplary forward-kinematic-mapping unit in the control unit shown in FIG. 3(a).

In the following description, reference is made to the accompanying drawings which are illustrations of embodiments in which the disclosed invention may be practiced. It is to be understood, however, that those skilled in the art may develop other structural and functional modifications without departing from the novelty and scope of the instant disclosure.

In referring to the description, specific details are set forth in order to provide a thorough understanding of the examples disclosed. In other instances, well-known methods, procedures, components and circuits have not been described in detail as not to unnecessarily lengthen the present disclosure.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Exemplary embodiments will be described below with reference to the several drawings, wherein like reference numerals designate identical or corresponding parts throughout the several views and embodiments. Accordingly, descriptions of such parts with like reference numerals will not be repeated with respect to multiple figures.

FIG. 1(a) illustrates an exemplary control apparatus according to a first embodiment. A control unit 8 controls an actuator 4 by a control signal 10. The actuator is connected to a tendon 2 in a tendon-driven device 31. The actuator 4 can actuate the tendon 2 based on the control signal 10. The tendon-driven device 31 includes a body 1 with a distal end 5 and a proximal end 6. The tendon 2 is attached at an end fitting 3 to the distal end 5 on the body 1. The body 1 is fixed on the proximal end 6 mechanically so that the tip of the tendon-driven device 31 on the distal end 5 can be bent to a direction of an arrow B. As the tendon 2 is being actuated, the tip of the tendon-driven device 31 on the distal end 5 can be moved.

FIG. 1(b) is a cross-sectional view along line A-A show in FIG. 1(a). The tendon 2 is located with an offset from a centroid 7 by distance d. The tendon 2 goes through an eyelet 32 in the body 1. Consequently, when the tendon 2 is actuated by actuator 4, the body 1 is loaded with a bending torque by the tendon 2 because the distance d works as a moment arm for tension in the tendon 2.

The control unit 8 includes a forward-kinematic-mapping unit 9 that computes estimations of angular displacement of the tendon-driven device 31 based on a kinematic mapping of a lamped-parameter model of the tendon-driven device in FIG. 1(c). The kinematic mapping maps an input tension in a tendon to an angular displacement of the tendon-driven device 31. For configuration parameters of the tendon-driven device 31, the tendon-driven device 31 is decomposed into multiple divisions 29, which are units of curvature. By concatenating the curvatures of the divisions, the kinematic mapping describes the posture of the tendon-driven device 31 even if the posture has an uneven curvature.

In the lamped-parameter model illustrated in FIG. 1(c), each division 29 has a linear spring constant for bending as a restoring element 33, pictured in gray in FIG. 1(c). This spring constant of the restoring element 33 corresponds to a bending stiffness of the body 1 in an interval of one division 29. In addition, a moment arm element 34 on edges of one division 29 represents the eyelet 32 and the offset with distance d as the moment arm for the tendon 2 in the body 1.

The following assumptions have been made for this lamped-parameter model:

A1: The tendon-driven device 31 does not extend or contract in the longitudinal direction.

A2: Each division 29 bends in a circular shape.

A3: The inclined angle between the tendon 2 and the moment arm element 34 is small. This assumption is valid when the lamped-parameter model has enough divisions 29 to make the angular displacement of divisions 29 small enough. For example, at least 20, 25, 30, 35, 40 or more divisions each having the same width may be described.

A4: The eyelet 32 is assumed to be a point. The tendon 2 is subject to a friction force at every eyelet 32. Friction forces and normal forces acting on the tendon 2 are concentrated forces. The direction of normal forces is a tangential direction of the restoring element 33 in each cell.

A5: Quasi-static equilibrium is satisfied. Friction forces are equal to maximum static friction forces proportional to the normal force at eyelets 32.

To map tension in the tendon 2 at a proximal side to tension in the tendon 2 at a distal side, propagation of tension in tendon 2 is modeled with friction force between adjoining divisions 29. FIG. 2 shows this relationship combining angular displacements for division i as the proximal side and division i+1 as the distal side among adjoining divisions 29.

In FIG. 2(a), tension j in division i ($T_{i,j}$) bends the restoring element of division i with moment arm d. Thus, the following constitutive equation is derived:

$$\kappa_i s_i = \frac{dT_i}{K_\theta} \tag{1}$$

where $\kappa_i$ denotes curvature of division i and $s_i$ denotes the length of division i, and $K_\theta$ denotes a bending stiffness of restoring element 33.

By using equation (1), the angular displacement $\theta_i$ (i.e., $\kappa_i s_i$) in FIG. 2 is calculated from tension in tendon 2 in division i. Due to this angular displacement, tension $T_{i,j}$ is decreased by friction force $f_{i,j}$ at the eyelet 32 between division i and i+1 as shown in FIG. 2(b).

Under assumption A4, force equilibrium is described as, $$T_{i+1}\sin\left(\frac{\theta_{i+1}}{2}\right) + T_i\sin\left(\frac{\theta_i}{2}\right) - N_i = 0 \tag{2}$$

$$T_{i+1}\cos\left(\frac{\theta_{i+1}}{2}\right) - T_i\cos\left(\frac{\theta_i}{2}\right) + f_i = 0 \tag{3}$$

Under assumption A5, friction force is proportional to normal force with friction coefficient $\mu$, $$f_i = \mu N_i \tag{4}$$

Under assumption A3, Equation (3) is described by, $$T_{i+1} = T_i - f_i \tag{5}$$

Using equations (2), (4), and (5), and assuming $\sin(\theta_i/2) \approx \sin(\theta_{i+1}/2)$, a ratio of tension $T_{i+1,j}$ and $T_{i,j}$ is described explicitly as, $$\frac{T_{i+1,j}}{T_{i,j}} = \left(\frac{1 - \mu\sin\frac{\theta_i}{2}}{1 + \mu\sin\frac{\theta_i}{2}}\right) \tag{6}$$

The assumption of $\sin(\theta_i/2) \approx \sin(\theta_{i+1}/2)$ gives an approximation of variation ratio of the angular displacement of adjoining divisions 29 in many situations, when there are enough divisions in the tendon-driven device 31. Equation (6) allows one to calculate tension $T_{i+1,j}$ by using only division i parameters. By using equation (1) and (6) from the proximal end 6 to the distal end 5 alternatively, tensions and angular displacement for all divisions 29 in the tendon-driven device 31 can be calculated.

Figure 3B:
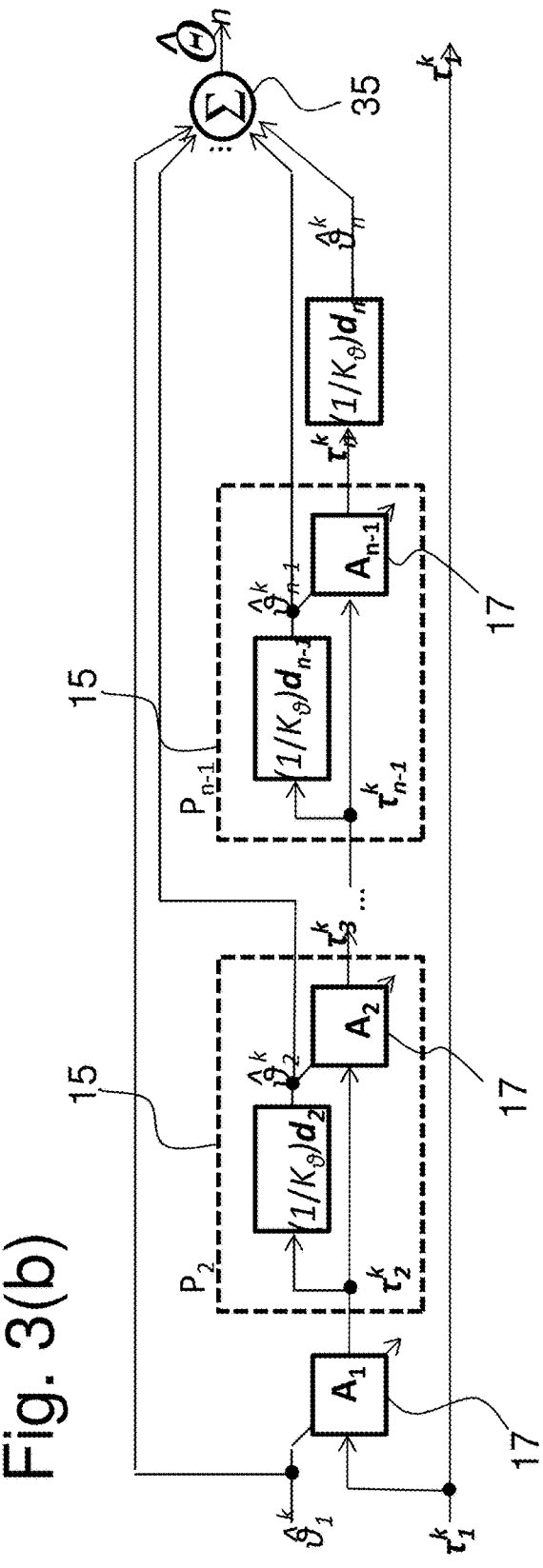

FIG. 3 illustrates a control block diagram of an exemplary control apparatus according to the first embodiment. FIG. 3(a) shows the control unit 8 and FIG. 3(b) shows the forward-kinematic-mapping unit 9 in the control unit 8 in FIG. 3(a). In the illustration, every signal is a discrete-time signal for discrete time k. There are n divisions in the device 31, thus, the division 1 denotes the division 29 at the proximal end 6 and the division n denotes the division 29 at the distal end 5. The control unit 8 controls the angular displacement $\Theta_n^k$ on the distal end 5 based on a coordinate system on the proximal end 6. To control the actuator 4, the control unit 9 sends tension $\tau_1^k$ that is the tension in tendon 2 at the division 1 (i.e., at the proximal end 6) as the control signal 10 for the actuator 4.

The control target $\Theta_n^k$ is input to an initial-value-generating unit 11. The initial-value-generating unit 11 outputs an estimation of angular displacement $\theta_1^{k\wedge}$ at the proximal end 6 and tension $\tau_1^k$ at the proximal end 6. These signals are input to the forward-kinematic-mapping unit 9. The forward-kinematic-mapping unit 9 outputs an estimation of angular displacement $\Theta_n^{k\wedge}$ at the proximal end 6 based on the coordinate system on the proximal end 6 and tension $\tau_1^k$ at the proximal end 6. The estimation of angular displacement $\Theta_n^{k\wedge}$ is input to an adding unit 12. The adding unit 12 calculates the difference $\theta e_1^k$ between the estimation of angular displacement $\Theta_n^{k\wedge}$ and the control target $\Theta_n^k$. This difference $\theta e_1^k$ is input to a checking unit 13. The checking unit 13 compares an absolute value of the difference $\theta e_1^k$ with a convergence criterion $\varepsilon_1$.

In the checking unit 13, if the difference $\theta e_1^k$ is smaller than the convergence criterion $\varepsilon_1$, the checking unit 13 outputs an activate signal to switch unit 14. Once the activate signal is input to the switch unit 14, the tension $\tau_1^k$ is sent to the actuator 4 as the control signal 10. Thus, the control unit 8 can control the actuator 4 for the control target $\Theta_n^k$. After that, the next control target $\Theta_n^{k+1}$ at k+1 is processed.

On the other hand, if the difference $\theta e_1^k$ is larger than the convergence criterion $\varepsilon_1$, the checking unit 13 sends the difference $\theta e_1^k$ to the initial-value-generating unit 11. The initial-value-generating unit 11 calculates the estimation of angular displacement $\theta_1^{k\wedge}$ and the tension $\tau_1^k$ based on both the control target $\Theta_n^k$ and the difference $\theta e_1^k$ iteratively.

An exemplary computing method for the estimation of angular displacement $\theta_1^{k\wedge}$ the tension $\tau_1^k$ in the initial-value-generating unit 11 is described as follows:

(1) calculate a difference between the control target $\Theta_n^k$ and the difference $\theta e_1^k$.
(2) multiply a ratio of length of division 1 and total length of the body 1 $s_1/s_{body}$ to the difference computed in (1) in order to calculate the estimation of angular displacement $\theta_1^{k\wedge}$
(3) multiply a bending stiffness of body 1 to the difference computed in (1) and then divide it by the moment arm d of the tendon 2 in order to calculate the tension $\tau_1^k$.

Thus, wherein the initial-value-generating unit is capable of computing an angular displacement and tension in a tendon at the proximal end based on a compensated value and adding the difference if the difference is larger than a convergence criterion.

FIG. 3(b) illustrates a control block diagram of the forward-kinematic-mapping unit 9 in FIG. 3(a). The forward-kinematic-mapping unit 9 computes the estimation $\Theta_n^{k\wedge}$ based on equations (1) and (6). A division-computing unit 15 pictured in a dashed line in FIG. 3(b) computes an estimation of angular displacement for each division serially. The division-computing unit $P_i$ calculates the estimation of angular displacement for division i and the tension for division i+1.

The tension for division i is mapped to the estimation of angular displacement $\theta_i^{k\wedge}$ by a block of $(1/K_\theta) d_i$ based on equation (1).

The tension ratio block 17 generates the tension for division i+1 from the tension for division i and the estimation of angular displacement for division i based on equation (6). Therefore, the tension ratio block 17 estimates the tension for division on the distal side by using only information for division on the proximal side.

After calculating estimations of an angular displacement for all of divisions, angular-displacement-adding unit 35 generates estimation $\Theta_n^{k\wedge}$ by summing them up.

FIG. 4 is another example of a control block diagram of an exemplary control apparatus according to the first embodiment. In FIG. 4, blocks and signals with same functionality as the ones in FIG. 3 are indicated by the same annotation signs as the ones in FIG. 3 and descriptions thereof are not repeated herein. Differences between the exemplary control apparatus of FIG. 4 as compared to the one of FIG. 3 are described below.

Figure 4A:
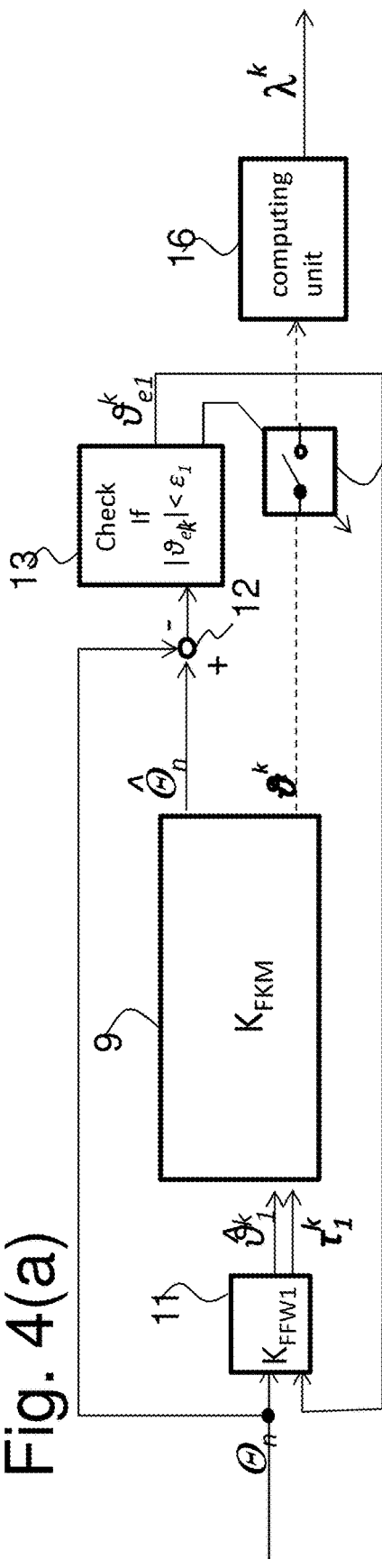
FIG. 4(a) illustrates an exemplary control unit shown in FIG. 1.

FIG. 4(a) is a control block diagram of the control unit 8 in FIG. 1. The control unit 8 in FIG. 4 outputs tendon displacement $\lambda^k$ as the control signal 10 instead of tension $\tau_1^k$ in FIG. 3. The tendon displacement $\lambda^k$ is amount of tendon pull or feed for the actuator 4. To output this signal, the control unit 8 has two differences from the control unit 8 in FIG. 3 as described below.

First, the forward-kinematic-mapping unit 9 outputs a vector of angular displacement for divisions $\theta^{k\wedge}$. Components of this vector are estimations of angular displacement for each division. Therefore the vector is described as, $$\theta^{k\wedge} = [\theta_1^{k\wedge}, \theta_2^{k\wedge}, \theta_3^{k\wedge} \ldots , \theta_n^{k\wedge}]^T \qquad (7)$$

Second, the vector of equation (7) is input to a tendon-displacement-computing unit 16. And then the tendon-displacement-computing unit 16 outputs the tendon displacement $\lambda^k$.

Figure 4B:
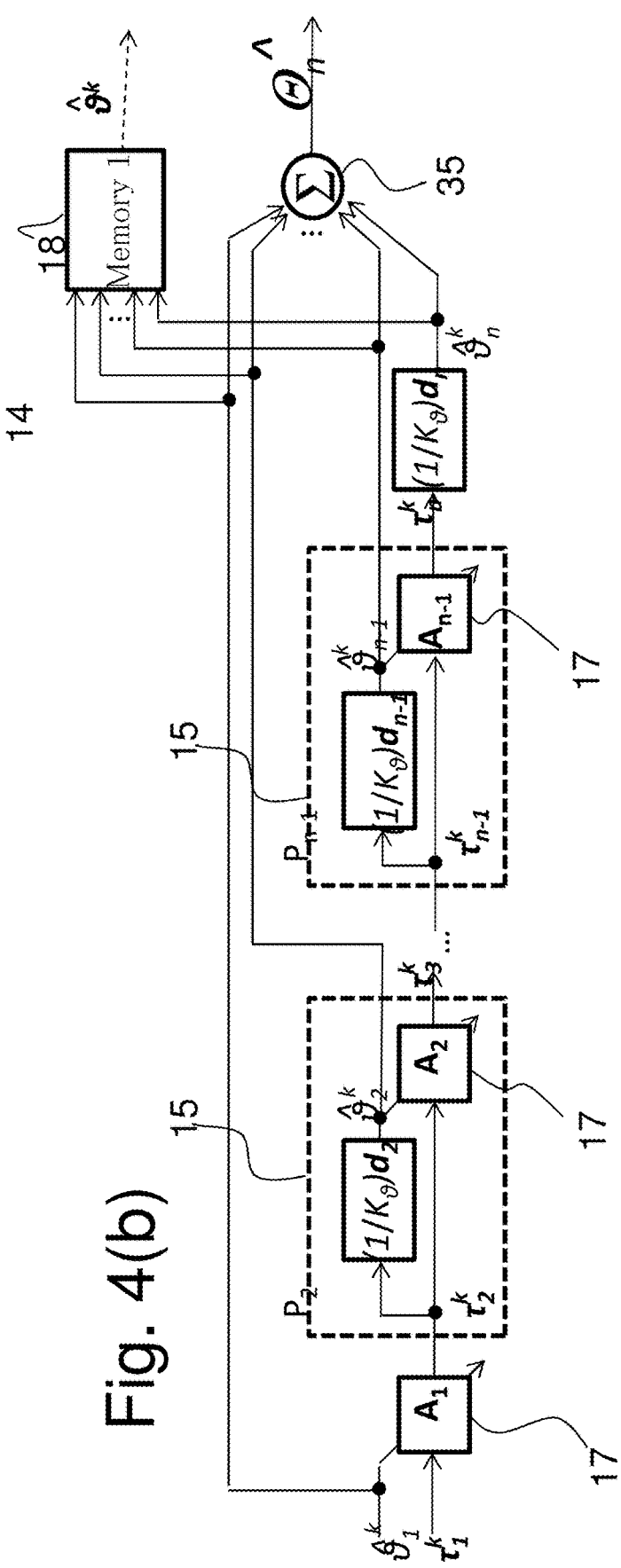
FIG. 4(b) illustrates an exemplary forward-kinematic-mapping unit shown in FIG. 4(a)

FIG. 4(b) illustrates a control block diagram of the forward-kinematic-mapping unit 9 in FIG. 4(a). To output the vector of estimations of angular displacement for divisions $\theta^{k\wedge}$, a first memory unit 18 computes this vector by storing all of output of an estimation of angular displacement for every division.

Figure 4C:
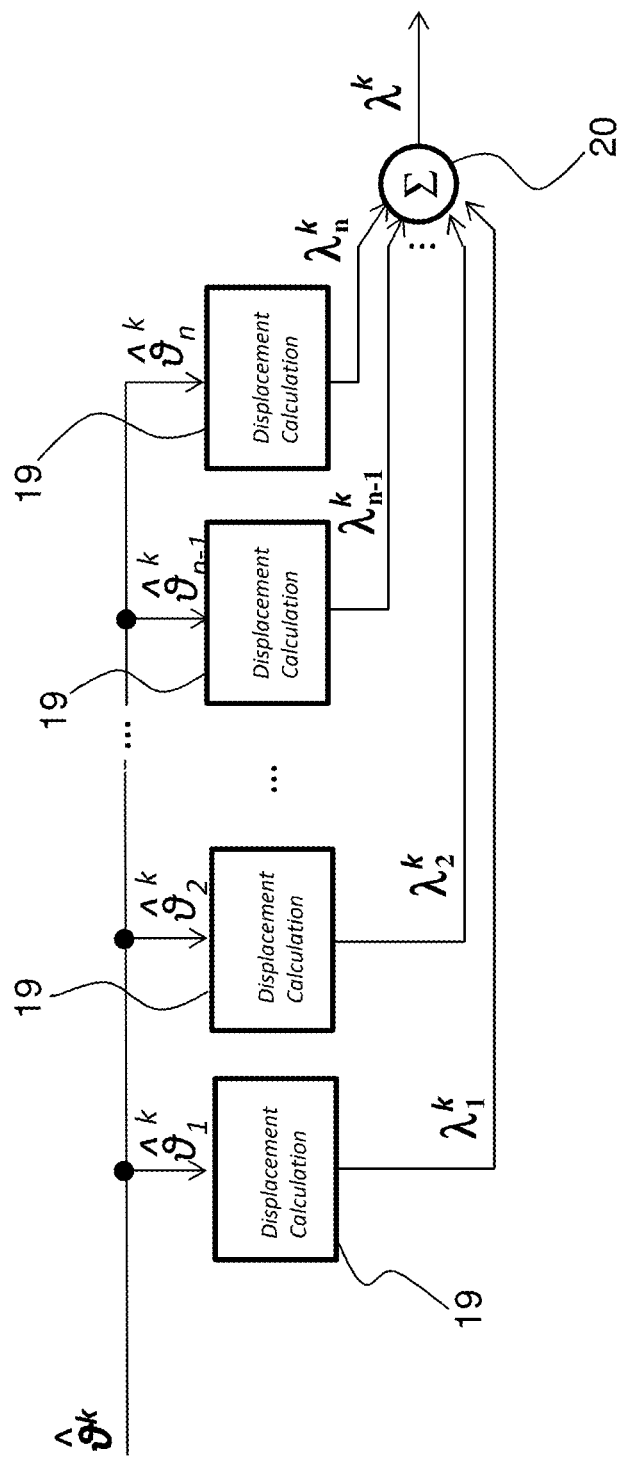
FIG. 4(c) illustrates an exemplary tendon-displacement-computing unit shown in FIG. 4(a).

FIG. 4(c) illustrates a control block diagram of the tendon-displacement-computing unit 16 shown in FIG. 4(a). By using every component in the vector $\theta^{k\wedge}$, a displacement calculation block 19 outputs a tendon displacement for each division.

This tendon displacement can be determined from a difference between a length of centroid and a length of tendon routing during bending. Consequently, the algorithm in the displacement calculation block 19 for division i is described as, $$\lambda_i^k = d_i \theta_i^{k\wedge} \qquad (8)$$

or, $$\lambda_i^k = d_i \operatorname{ArcTan}(\theta_i^{k\wedge}) \qquad (9)$$

After computation of a tendon displacement for every cell, a displacement-adding unit 20 generates the tendon displacement $\lambda^k$ by summing all of tendon displacements for each division.

FIG. 5 illustrates a control block diagram of another exemplary control apparatus according to the first embodiment. The control apparatuses illustrated in FIG. 5 are examples of combination with feed-forward control and feedback control.

In FIG. 5, blocks and signals with same functionality as the above-described examples are indicated by the same annotation signs and descriptions thereof are not repeated herein. Difference are described below.

Figure 5A:
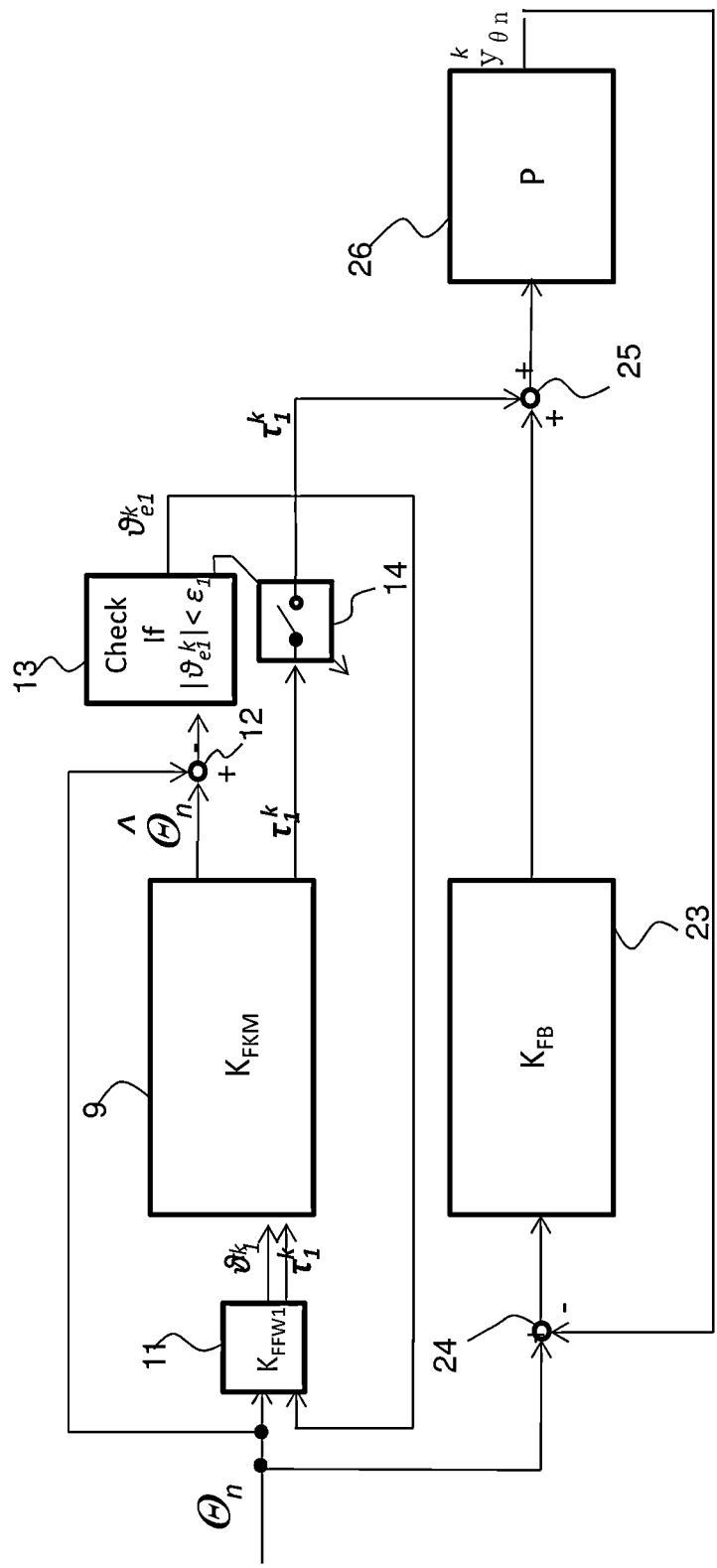
FIG. 5(a) illustrates an exemplary control unit and a plant including an actuator and tendon-driven device.

FIG. 5(a) illustrates a control block diagram of the control apparatus including the control unit 8 and a plant 26 including the actuator 4 and the tendon-driven device 31 shown in FIG. 1. The control unit 8 in FIG. 5(a) includes the control unit in FIG. 3(a) as feed-forward control system. A feedback control unit 23 is combined with this control unit to improve control accuracy. Thus, the control signal can be compensated based on measured data obtained from sensors located on one or more of the body segments of the apparatus and control accuracy can be improved.

The control target $\Theta_n^k$ is input to the feedback adding unit 24 as well as the initial-value-generating unit 11. The feedback adding unit 24 computes a difference between the control target $\Theta_n^k$ and observation signal $Y\theta_n^k$ of the angular displacement of the body 1 in the tendon-driven device 31.

In an exemplary embodiment, the observation signal $Y\theta_n^k$ is obtained via sensors (not shown), such as electromagnetic field sensors. One or more of these sensors may be placed on the body 1. The sensors may include strain gauges to measure mechanical strain of the body 1. In one exemplary embodiment, multiple sensors for obtaining observation signal $Y\theta_n^k$ are attached along a longitudinal direction of the body 1. For example, a sensor may be placed on each of the body segments along a longitudinal direction of the body 1.

In the exemplary embodiment shown and described herein, the feedback control unit 23 is a proportional-integral-derivative (PID) controller. Based on this difference, the feedback control unit 23 generates a compensation signal and outputs this compensation signal to a compensation-adding unit 25.

The compensation-adding unit 25 compensates the tension $\tau_1^k$ from the switch unit 14 by using the output of the feedback control unit 23, and then outputs this compensated tension $\tau_1^k$ to the plant 26.

Figure 5B:
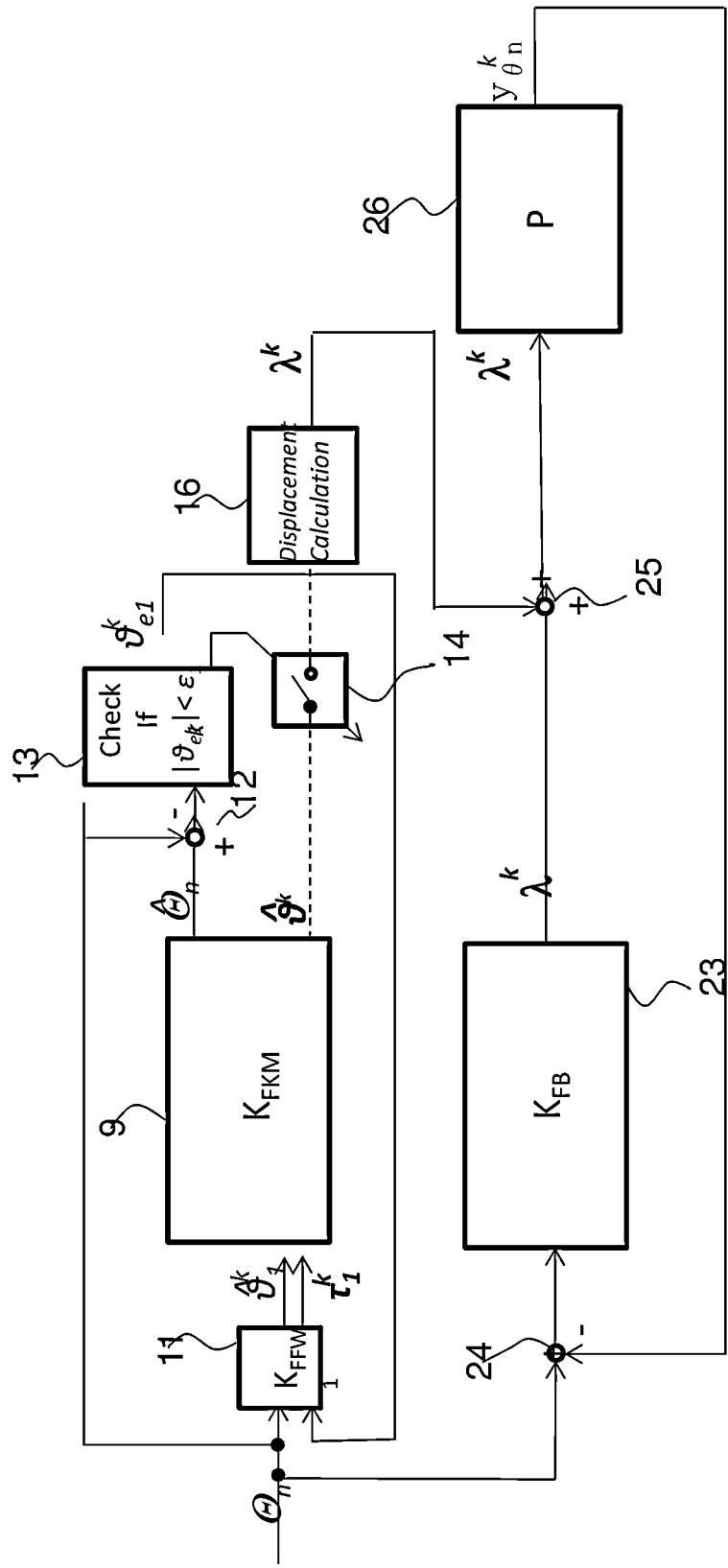
FIG. 5(b) illustrates an example of a control apparatus combined with feedback control.

FIG. 5(b) is yet another example of the control apparatus combining with feedback control. The difference from the control apparatus in FIG. 5(a) is to use the control unit shown in FIG. 4 instead of the control unit shown in FIG. 3.

In FIG. 5(b), the feedback control unit 23 outputs the compensation signal for the tendon displacement $\lambda^k$ from the tendon-displacement-computing unit 16. And then, the compensation-adding unit 25 compensates the tendon displacement $\lambda^k$ and sends this compensated tendon displacement $\lambda^k$ to the plant 26.

In another exemplary embodiment, the configuration of the control apparatus is similar to the control apparatus of FIG. 1. However, the forward-kinematic-mapping unit 9 includes a tension-calculating function of the angular displacement to calculate a tension in the proximal end 6 as the control signal 10 for actuator 4.

Figure 6A:
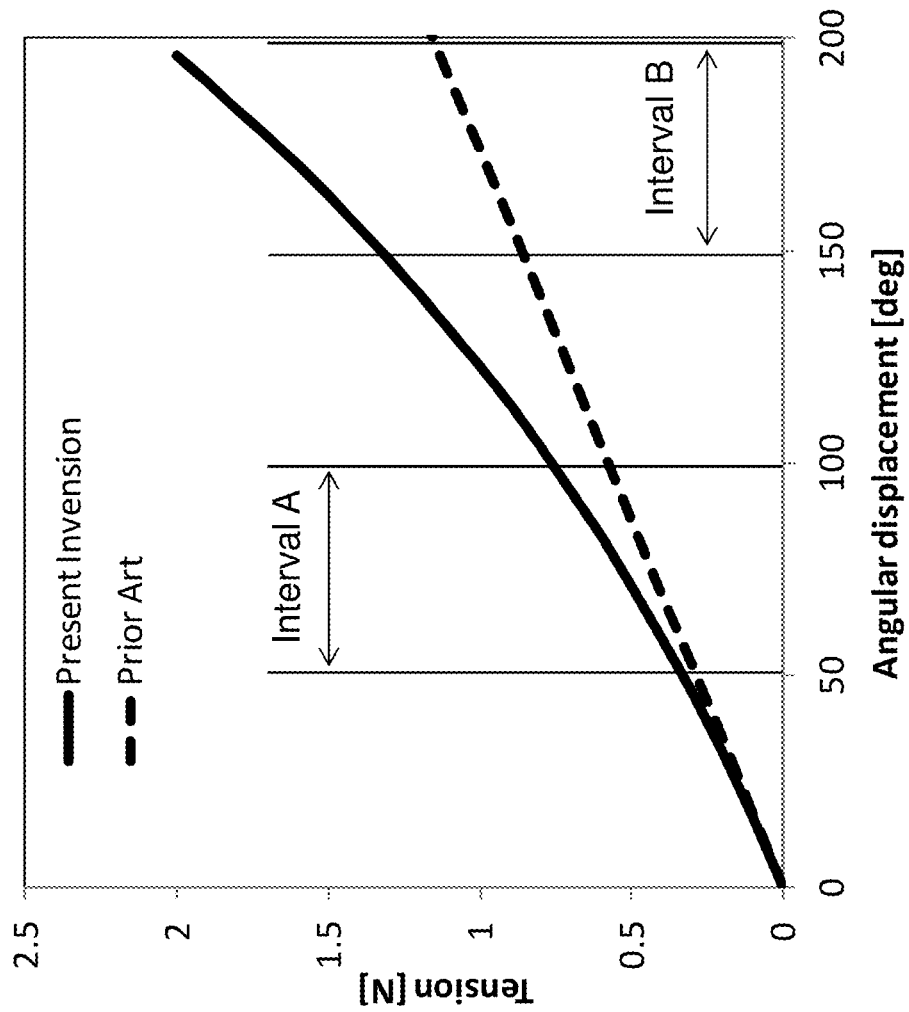
FIG. 6(a) illustrates the angular displacement v. tension for the present invention compared to a device where tension is not taken into account.

FIG. 6(a) is a graph of an example of the tension-calculating function. The solid line is an exemplary the tension-calculating function of the present invention.

A tension validation measurement is also depicted in FIG. 6(a) for comparison. This measurement ignores the friction between the tendon 2 and the body 1 is presented as a dotted line in the graph. Consequently, the relationship between the tension in the proximal end 6 and the angular displacement at the distal end 5 is linear. Compared to this measurement, the exemplary tension-calculating function described by the solid line is a non-linear increasing function. Therefore, an increment of a tension within the same interval of the angular displacement is increasing with the increase in the angular displacement. For example, interval A and B in the FIG. 6(a) have the same width of the angular displacement (i.e., interval "A" which has an angular displacement from $x_1$ to $x_{1+A}$, is equal to interval "B" which has an angular displacement from $x_2$ to $x_{2+A}$). However, the increment of the tension in these intervals is different. Particularly, the increment of tension in interval B is larger than the increment of tension in interval A since the angular displacement increases, the nonlinearity and the deviation from the frictionless model increases.

In some embodiments, the tension-calculating function can be the sequential calculation using, for example, the ratio of a tension in equations (6), (17) and (18). By using one of these equations, a friction force in each division can be determined. Then, by sum up the friction force in all of divisions, a required tension to compensate the friction can be calculated.

These functions can have pre-determined parameters so that these non-linear monotonically increasing functions fit to the experimental data of a required tension for an angular displacement. In some embodiments, the non-linear monotonically increasing function is determined from fitting the data from the tension calculated in one or more of equations (6), (17) and (18).

Thus, the present invention includes determining the tension-calculating function based on these ratios or, for example, a table based on these ratios. Other embodiments include non-linear equations such as an exponential function and a polynomial function that can be used to determine the tension. Tabulated values may include tables where friction is not positively defined but yet the tabulated values have the same relationships between the tension and angular displacement is also within the scope of the present invention.

Figure 6B:
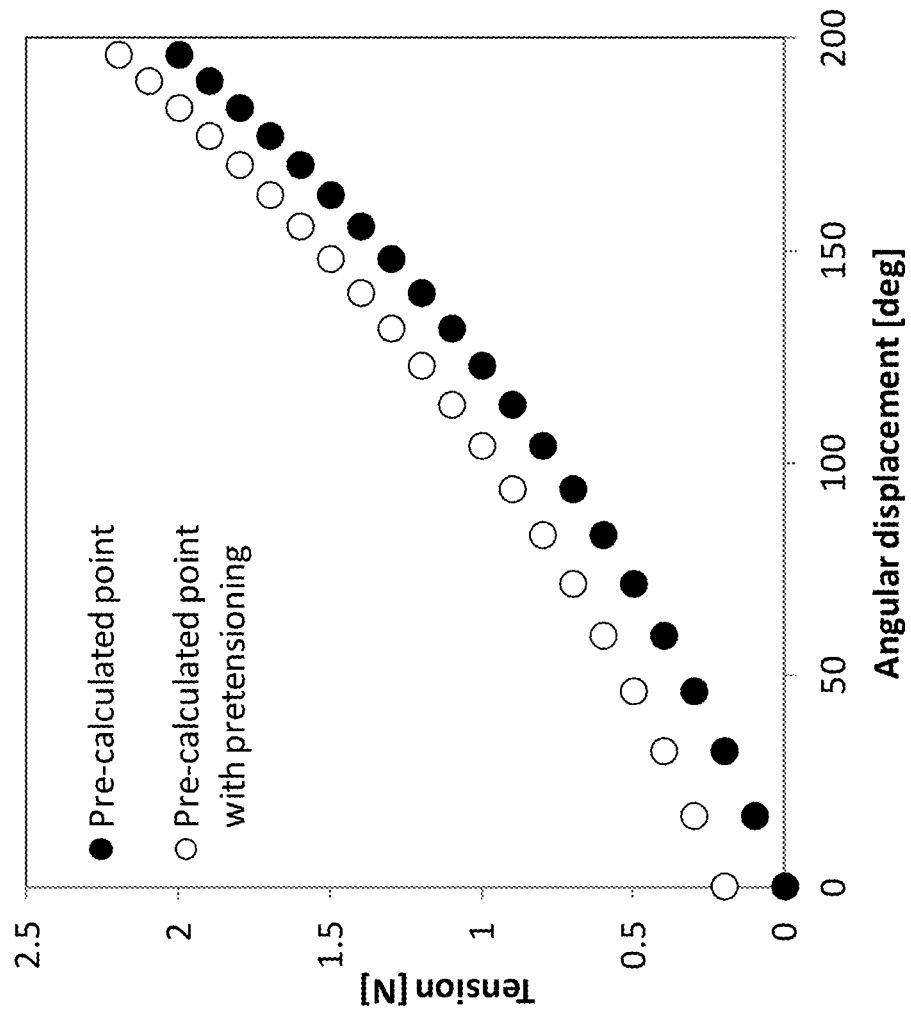
FIG. 6(b) illustrates the angular displacement v. tension where a pre-tension is included.

FIG. 6(b) is another example of an embodiment where a numerical table is used to determine tension. The forward-kinematic-mapping unit 9 in FIG. 6(b) has a numerical table determined in advance instead of the tension-calculating function. The solid markers in FIG. 6(b) denote data in the numerical table. These data can be predetermined experimentally. Furthermore, the tension between adjoining solid dots can be determined by using a linear interpolation.

The open in FIG. 6(b) depict similar data in the numerical table. However, in this example, the tension has pre-tensioning value to avoid a slack of a tendon. Therefore, the open markers are offset from the solid markers that were not subject to pre-tensioning.

Second Embodiment

FIG. 7(a) illustrates of an exemplary control apparatus according to a second embodiment. A control unit 8 controls actuators 4 by a control signal 10. The actuators 4 are connected to four tendons 2 in a tendon-driven device 31. The tendon-driven device 31 includes two body segments, hereinafter referred as a distal body segment 1A and a proximal body segment 1B, connected serially. The distal body segment 1A is extended from a distal end 5 to a tip of the proximal body 21. On the other hand, the proximal body segment 1B is extended from a boundary of sections 21 to a proximal end 6. In this example, each body segment has two tendons 2. By using these pairs of tendons 2, the actuators 4 can bend the tendon-driven device 31 with two bending sections.

FIG. 7(b) is a cross-sectional view along line C-C shown in FIG. 7(a). The tendons 2 are located with an offset from a centroid 7. Four tendons have an offset distance $d_1, d_2, d_3, d_4$. The tendons with distance $d_1$ and $d_2$ consist of an antagonistic pair for the distal body 1A. Thus, these tendons are terminated on the distal end 5. The offset distance d1 and d2 are signed scalar values. Therefore, these are same magnitude of distance but have different signs, i.e., a positive value and negative value. In FIG. 7(*b*), $d_1$ is positive value.

In the same manner, the tendons with distance $d_3$ and $d_4$ are attached to the proximal body segment 1B. These are terminated on the boundary of sections 21. The offset distance $d_3$ is positive value and the offset distance $d_4$ is negative value. Although these are same magnitude as each other, the sign is different.

FIG. 8 illustrates an exemplary control unit 8 according to the second embodiment. FIG. 8(*a*) illustrates an exemplary control unit 8 and FIG. 8(*b*) illustrates an exemplary forward-kinematic-mapping unit 9 in the control unit 8 shown in FIG. 8(*a*). FIG. 8(*c*) illustrates another example of the control unit 8 combining with a feedback controller. In the diagram, every signal is a discrete-time signal for discrete time k. There are n divisions in the device 31, thus, the division 1 denotes the division 29 at the proximal end 6 and the division n denotes the division 29 at the distal end 5. Furthermore, division h denotes the division 29 with its edge of a proximal side on the boundary of sections 21.

The control unit 8 controls two targets of the angular displacement for the distal body segment 1A as well as the proximal body segment 1B. The one is the angular displacement $\Theta_n^k$ on the distal end 5 based on a coordinate system on the proximal end 6. The other one is the angular displacement $\Theta_h^k$ on the boundary of sections 21 based on a coordinate system on the proximal end 6.

The control unit 8, as well as other control units as described herein (for example, in FIGS. 3, 4, 5, 8 and 9) can implement each function as described herein by any or a combination of technologies including via hardware such as CPU or ROM or RAM or via discrete logic circuit(s), application specific integrated circuits, or via programmable logic.

To control the four actuators 4, the control unit 8 sends a tendon-displacement vector $\lambda^k$ whose components are tendon displacements of four tendons 2 for corresponding actuators as the control signal 10. The tendon-displacement vector $\lambda^k$ is described as, $$\lambda^k = [\lambda_1^k, \lambda_2^k, \lambda_3^k, \lambda_4^k]^T \tag{10}$$

The component $\lambda j^k$ denotes the tendon displacement of a tendon j.

The control targets $\Theta_n^k, \Theta_h^k$ are input to an initial-value generating unit 11. The initial-value-generating unit 11 outputs an estimation of angular displacement $\theta_1^{k\wedge}$ at the proximal end 6 and a tension vector $\tau_1^k$ at the proximal end 6. Specifically, the tension vector $\tau_1^k$ composes tensions in each tendon 2 at the proximal end 6. The tension vector $\tau_1^k$ is described as, $$\tau_1^k = [\tau_{1,1}^k, \tau_{1,2}^k, \tau_{1,3}^k, \tau_{1,4}^k]^T \tag{11}$$

The component $\tau_{i,j}^k$ of the tension vector $\tau_i^k$ denotes a tension in the tendon j at the division i.

The estimation of angular displacement $\theta_1^{k\wedge}$ and the tension vector $\tau_1^k$ are input to the forward-kinematic-mapping unit 9. Moreover, a vector $\theta^{k-1\wedge}$ of estimations of angular displacement for divisions at previous time, i.e., time k−1 is input from a second memory unit 22. The vector $\theta^{k-1\wedge}$ is defined by equation (7). The forward-kinematic-mapping unit 9 outputs estimations of angular displacement $\Theta_n^{k\wedge}, \Theta_h^{k\wedge}$ and the vector of estimations of angular displacement $\theta^{k\wedge}$ at present time k.

The vector of estimations of angular displacement $\lambda^k$ is input to the second memory unit 22 as well as switch unit 14. The second memory unit 22 stores the vector $\lambda^k$ and will send this vector to the kinematic-mapping unit 9 at time k+1. On the other hand, the estimations of angular displacement $\Theta_n^{k\wedge}, \Theta_h^{k\wedge}$ are input to an adding unit 12. The adding unit 12 calculates differences $\theta e_1^k, \theta e_2^k$ between the control targets and the estimations. These differences $\theta e_1^k, \theta e_2^k$ are input to a checking unit 13. The checking unit 13 compares an absolute value of the differences $\theta e_1^k, \theta e_2^k$ with convergence criteria $\varepsilon_1, \varepsilon_2$.

In the checking unit 13, if the differences $\theta e_1^k, \theta e_2^k$ are smaller than the convergence criteria $\varepsilon_1, \varepsilon_2$, the checking unit 13 outputs an activate signal to switch unit 14. Once the activate signal is input to the switch unit 14, the vector of estimations of angular displacement $\theta^{k\wedge}$ is sent to a tendon-displacement-computing unit 16.

The tendon-displacement-computing unit 16 outputs a tendon displacement vector) $\lambda^k$ to the actuator 4 as control signal 10. After that, the next control targets $\Theta_n^{k+1\wedge}, \Theta_h^{k+\wedge}$ at k+1 are processed.

However, if the differences $\theta e_1^k, \theta e_2^k$ are larger than the convergence criteria $\varepsilon_1, \varepsilon_2$, the checking unit 13 sends the differences $\theta e_1^k, \theta e_2^k$ to the initial-value-generating unit 11. The initial-value-generating unit 11 calculates the estimation of angular displacement $\theta_1^{k\wedge}$ and the tension $\tau_1^k$ based on both the control target $\Theta_n^{k\wedge}, \Theta_h^{k\wedge}$ and the differences $\theta e_1^k, \theta e_2^k$ iteratively.

The initial-value-generating unit 11 is further described by the exemplary embodiment of FIG. 9. The control targets are input separately to two adding units. These two adding units output differences between the control target $\Theta_n^{k+1\wedge}, \Theta_h^{k+\wedge}$ and the differences $\theta e_1^k, \theta e_2^k$ from the checking unit 13 (see FIG. 8(*c*)). The estimation of angular displacement $\theta_1^{k\wedge}$ is determined by multiplying a ratio of a length of divisions $s_1/s_{proximal}$ to this difference. The length $S_{proximal}$ denotes the length of the proximal body segment 1B.

These differences are input to another adding unit to compute a difference between each other. This difference is the angular displacement of the tip of the distal body segment 1A based on the bottom of the distal body 1A. This angular displacement of the tip of the distal body segment 1A is input to a bending stiffness block for the distal body 1A. By multiplying bending stiffness $K_{\theta\_distal}$ of body A, this block computes a bending torque for the distal body 1A.

The bending torque for the distal body segment 1A is input to a tension-allocation unit 36. The tension-allocation unit 36 determines the tensions at division h+1 for the two tendons 2 terminated on the tip of the distal body 1A. The division h+1 denotes the most bottom division in the distal body 1A.

To determine tensions for tendons 2 at division h+1 for this example, the tension-allocation unit 36 solves the following optimization as an algorithm 16 that can be described by the equation.

$$\text{minimize Max}(\tau_{h+1}) \tag{12}$$

$$\text{subject to} \begin{cases} \tau_{h+1} \geq 0 (\text{or } T_\varepsilon) \\ (1/K_{\theta\_distal})d_{h+1} - \tau_{h+1} = (\Theta_n - \theta_{e1}) - (\Theta_h - \theta_{e2}) \end{cases}$$

In the equation (12), $T_\varepsilon$ denotes a tension for pre-tensioning to avoid slacks of tendons and $d_{h+1}$ is a moment-arm vector for division h+1. This vector is described as, $$d_{h+1} = [d_1, d_2, 0, 0] \tag{13}$$

A pre-tension $T_\varepsilon$ may be applied to the apparatus prior to use and its effects are described by the equations above. The amount of pre-tension applied may be varied based on the use of the apparatus. Preferably, any pre-tension applied to the apparatus is applied to each of the tendons equally. The equation (12) can allocate minimum tension fulfilling the pre-tensioning condition to the tendons for the distal body 1A.

To determine tensions for rest of tendons, a second tension-allocation unit 37 performs an algorithm by using a bending torque for the proximal body segment 1B from the bending stiffness block $K_{\theta\_proximal}$ as well as the tension vector $\tau_{h+1}$ at division h+1. The algorithm of the second tension-allocation unit 37 is described as, $$\text{minimize Max}(\tau_1) \quad (14)$$
$$\text{subject to} \begin{pmatrix} \tau_1 \geq 0 (\text{or } T_\varepsilon) \\ (1/K_{\theta\_proximal})d_1 - \tau_1 = \Theta_h - \theta_{e2} \\ T_{j,1} = T_{j,h+1} \text{ if } T_{j,h+1} \neq 0 \end{pmatrix}$$

In equation (14), $d_1$ denotes the moment-arm vector for division 1. This vector is described as, $$d_1 = [d_1, d_2, d_3, d_4] \quad (15)$$

By using this algorithm, the second tension-allocation unit 37 outputs the tension vector for division 1.

Figure 8A:
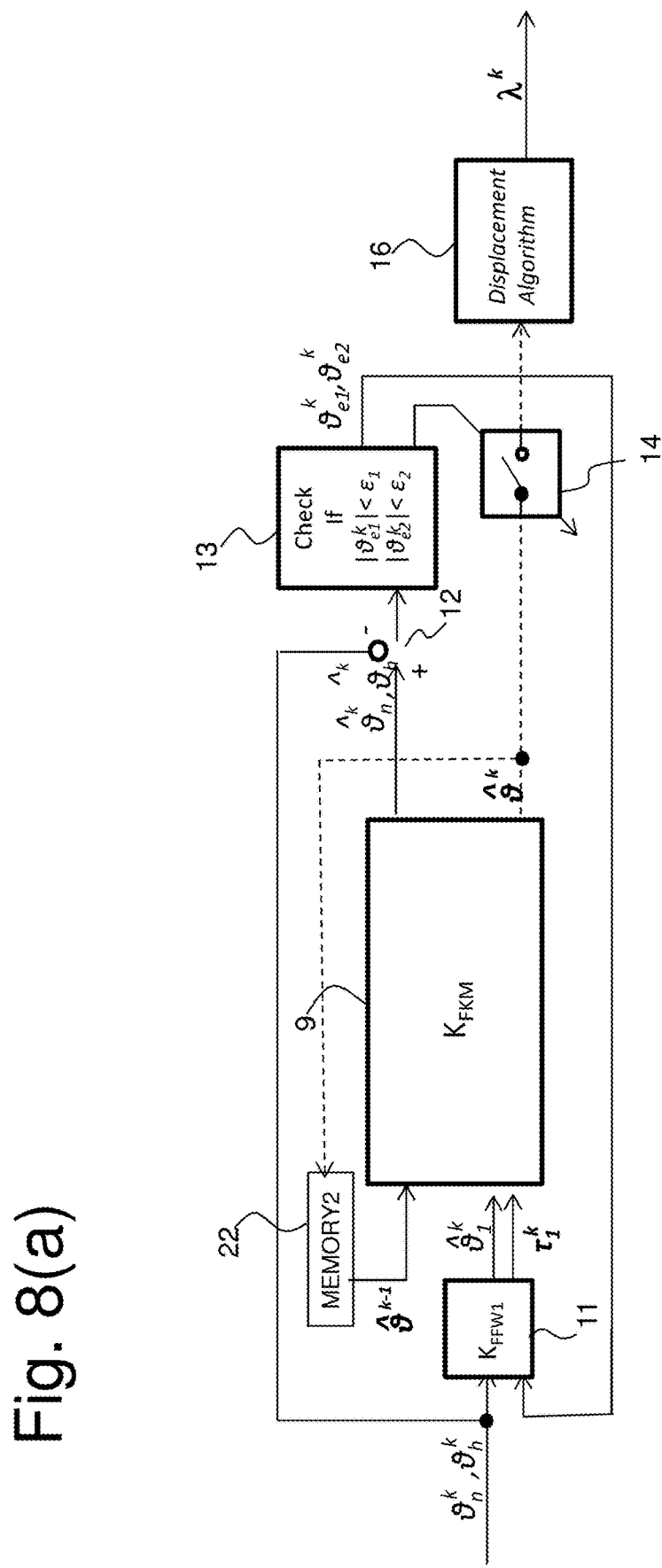
FIG. 8(a) illustrates and exemplary control unit.
Figure 8B:
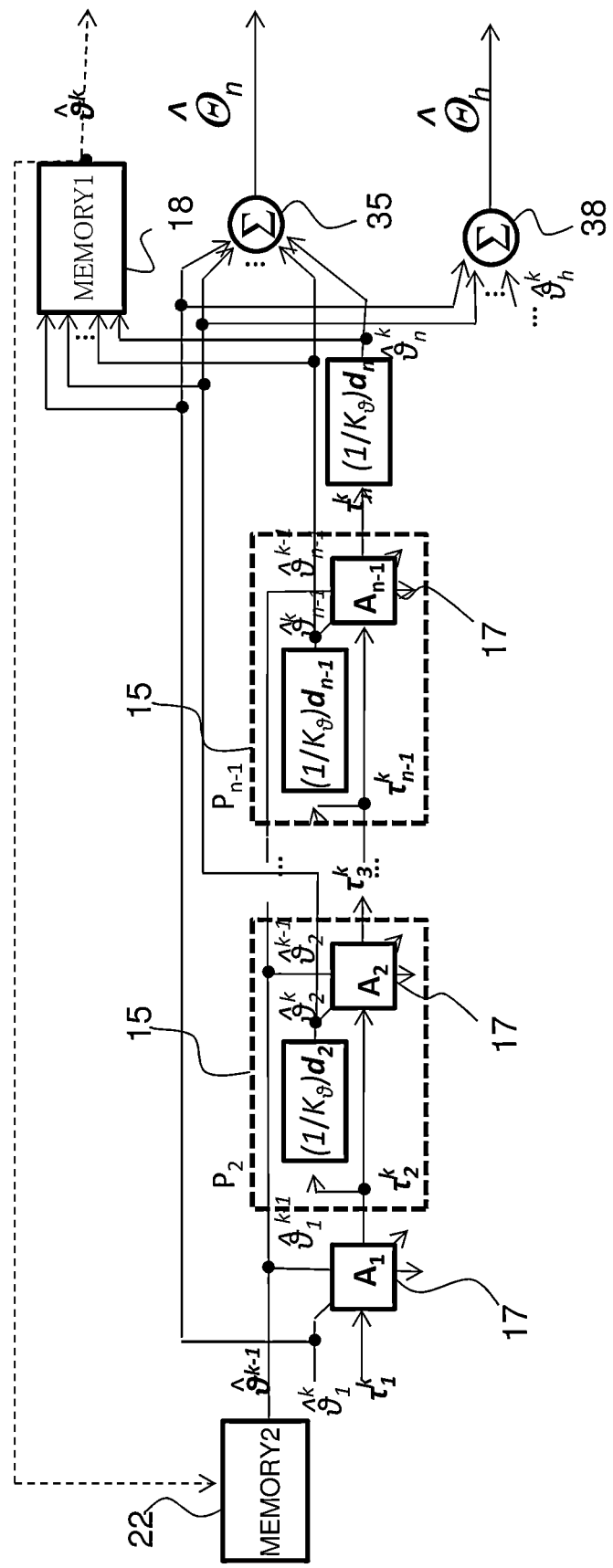
FIG. 8(b) illustrates an exemplary forward-kinematic-mapping unit in the control unit shown in FIG. 8(a)

In further detail, FIG. 8(b) illustrates an exemplary forward-kinematic-mapping unit 9 shown in FIG. 8(a). The forward-kinematic-mapping unit 9 computes the estimations $\Theta_n^{k+1\wedge}$, $\Theta_h^{k+\wedge}$. The basic calculation is based on equations (1) and (6), however, these are vectorized for multiple tendons. A division-computing unit 15 shown in a dashed line in FIG. 8(b) computes an estimation of angular displacement for each division serially. The division-computing unit $P_i$ calculates the estimation of angular displacement for division i and the tension for division i+1.

The tension vector $\tau_i$ for division i is mapped to the estimation of angular displacement $\theta_i^{k\wedge}$ by a block of $(1/K_\theta)$ $d_i$ based on equation (1). However, this block performs inner product between the tension vector $\tau_i$ and the vector $(1/K_\theta)$ $d_i$.

The tension ratio block 17 generates the tension vector $\tau_{i+1}$, for division i+1 from the tension vector $\tau_i$ for division i and the estimation of angular displacement $\theta_i^{k\wedge}$, $\theta_i^{k\wedge}$ for division i at time k and k−1.

The tension ratio block 17 performs linear transformation from the tension vector $\tau_i$ to the tension vector $\tau_{i+1}$, by multiplying the following matrix $A_i$ for division i in case of m tendons in the device.

$$A_i = \begin{bmatrix} \alpha_{i,1}^k & & & 0 \\ & \ddots & & \\ & & \alpha_{i,j}^k & \\ & & & \ddots \\ 0 & & & \alpha_{i,m}^k \end{bmatrix} \quad (16)$$

where $$\alpha_{i,j}^k = \frac{\tau_{i+1,j}^k}{\tau_{i,j}^k} = \left(\frac{1 - \mu\sin(|\theta_i^k|/2)}{1 + \mu\sin(|\theta_i^k|/2)}\right)^{sgn(d_{i,j})sgn(\theta_i^k - \theta_i^{k-1})}$$

In equation (16), Sgn is a sign function defined as, $$Sgn(x) := -1 \text{ if } x<0, 0 \text{ if } x=0, 1 \text{ if } x>0 \quad (17)$$

The sign function in equation (16) manages the direction of friction force between tendons and the body against tensions in tendons. The direction of friction force depends on the position of tendon j against the centroid 7, i.e., Sgn ($d_j$). Furthermore, by using estimation of angular displacement $\theta_i^{k-1\wedge}$ at previous time k−1, matrix $A_i$ can consider a hysteresis feature of friction force. Therefore, the direction of friction force is also dependent on a bending direction of division i at time k, i.e., Sgn ($\theta_i^{k\wedge} - \theta_i^{k-1\wedge}$).

After calculating estimations of an angular displacement for all of divisions, an angular-displacement-adding unit 35 and a second angular-displacement-adding unit 38 generate estimation $\Theta_n^{k\wedge}$, $\Theta_h^{k\wedge}$ by summing them up. A first memory unit 18 stores estimations of angular displacement for every division, then outputs the vector of angular displacement for divisions. Meanwhile, the second memory unit 22 stores the vector $\theta_k^{\wedge}$. The vector stored in the second memory unit 22 will be used at next time k+1 as input for the division-computing unit 15.

Figure 8C:
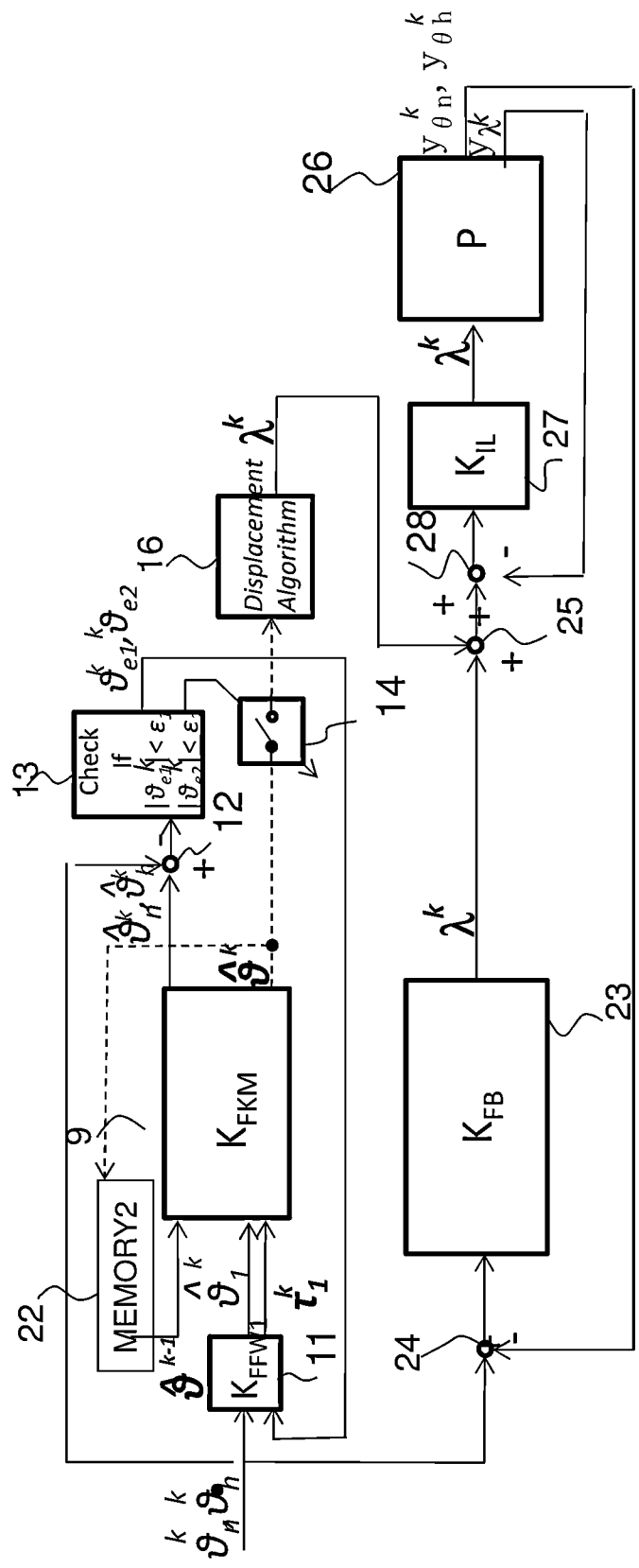
FIG. 8(c) illustrates another exemplary control apparatus according to the second embodiment.

FIG. 8(c) illustrates another exemplary control apparatus according to the second embodiment. This control apparatus is an example of a combination with feed-forward control and feedback control. In FIG. 8(c), blocks and signals with same functionality as the above-described examples indicated by the same reference numbers and descriptions thereof are not repeated herein. Specifically, only the differences are described below.

FIG. 8(c) illustrates a control apparatus including the control unit 8 and a plant 26 including the actuator 4 and the tendon-driven device 31 shown in FIG. 7. The control unit 8 in FIG. 8(c) includes the control unit in FIG. 8(a) as a feed-forward control system. A feedback control unit 23 is combined with this control unit to improve control accuracy.

The control targets $\Theta_n^k$, $\Theta_h^k$ are input to the feedback adding unit 24 as well as the initial-value-generating unit 11. The feedback adding unit 24 computes a difference between the control targets $\Theta_n^k$, $\Theta_h^k$ and observation signal $Y_{\Theta nk}$, $Y_{\Theta hk}$ of the angular displacement of the body segments 1A, 1B in the tendon-driven device 31.

The exemplary feedback control unit 23 shown in FIG. 8(c) is a proportional-integral-derivative (PID) controller. Based on this difference, the feedback control unit 23 generates a compensation signal and outputs this compensation signal to a compensation-adding unit 25.

The compensation-adding unit 25 compensates the tendon-displacement vector $\lambda_1^k$ from the tendon-displacement-computing unit 16 by using the output of the feedback control unit 23, and then outputs this compensated tendon-displacement vector $\lambda_1^k$ to the inner-loop-feedback adding unit 28.

The inner-loop-feedback adding unit 28 and an inner-loop unit 27 create an inner loop feedback system for accurate targeting of the tendon displacement. The inner-loop-feedback adding unit 28 computes a difference between the tendon displacement vector $\lambda_1^k$ and a vector of observation signal of the tendon displacement $Y_{\lambda 1k}$. The inner-loop unit 27 is a PID controller. Therefore, the inner-loop unit 27 computes a compensation signal for the tendon displacement vector $\lambda_1^k$.

The inner-loop unit 27 can increase control accuracy for the tendon displacement as well as a control band width for the control unit 8.

The embodiments described in detail above describe a multi-section continuum robot. Such a robot may be used, for example, for endoscopic surgical clipping of intracranial aneurysms. The robot may have one, two, three, four, or more sections for bending actuated by tendon wires. In on embodiment, the robot has two sections for bending actuated by tendon wires. By actuating the two sections independently, the robot can generate a variety of posture combinations by these sections while maintaining the top angle. Each body section may be actuated by a single tendon wire. Alternatively, two or more tendon wires may be used to actuate each body section (see FIG. 7(a)) where the tendon wires are on opposite sides of the centroid. The features as described herein offer more flexibility in positioning of the tip than a conventional endoscope for large viewing and/or working angles of up to 180 degrees.

Kinematic Mapping with Tension Propagation Model

Figure 14A:
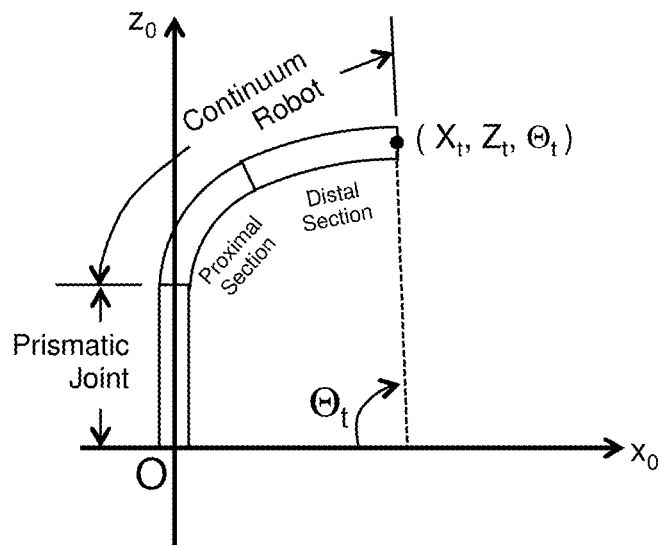
Figure 14B:
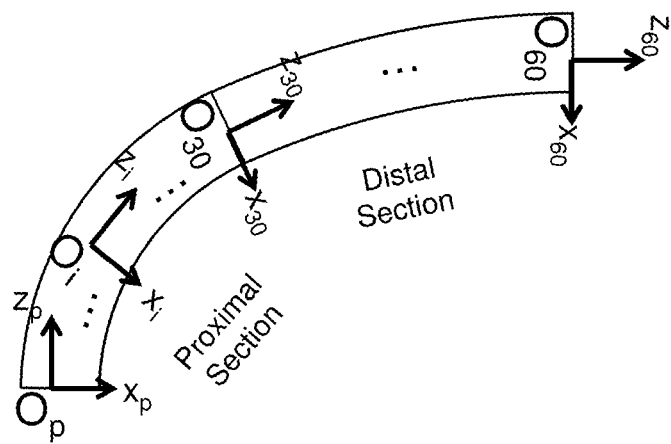

FIG. 14 is a schematic joint configuration of an exemplary robot. The planer bending continuum robot is mounted on the prismatic joint grounded on the task space coordinate mechanically. To derive kinematic mapping for this robot, we choose the exemplary frame convention in FIG. 14A, especially we define +z-axis to be tangent to the base of the continuum robot as well as the prismatic joint. FIG. 14B shows an enlarged illustration about the frame convention of the continuum robot. We set the tip frame of each cell in the continuum robot as individual joint coordinates. Therefore the proximal and distal sections have thirty joint coordinates in our model. Other points and fewer or more divisions are also contemplated. These coordinates represent the backbone configuration, e.g. the robot posture. In some embodiments, these coordinates of cells are modeled as under-actuated joints at two bending sections constrained by friction force between tendons and the eyelets.

The kinematic mapping process and methods as described herein is able to provide models that arrive at the transformation that gives the actuator parameters of the robot. These include the pull amount of tendons in the continuum robot and displacement of the prismatic joint, based on the tip frame characterized by ($X_t$, $Z_t$, $\theta_t$ algorithm for inverse kinematic mapping) in the task space coordinate. This transformation can be split into to two steps. First, we extended forward kinematic mapping (FKM) of the continuum robot to vectorized form for multi tendons in multi-section continuum robot. Second, by using this forward kinematic mapping (extended FKM), we presented iterative alg g (IKM) from the tip frame to the pull amount of tendons and the displacement of the prismatic joint.

To extend the forward kinematic mapping model for mapping to multiple tendon situations, we assume that we have available to use m appropriately distributed tendons for multiple sections. This allows one to write the tension of tendons at cell i at time k as the following vector.

$$\tau_i^k = [\tau_1^k \ldots \tau_j^k \ldots \tau_m^k]^T \qquad (18)$$

In the same manner, tendon moment arms in the robot can be defined by the following matrix form.

$$D = \begin{bmatrix} d_1 \\ \vdots \\ d_n \end{bmatrix} = \begin{bmatrix} d_{1,1} & \ldots & d_{1,j} & \ldots & d_{i,m} \\ \vdots & & \vdots & & \vdots \\ d_{n,1} & \ldots & d_{n,j} & \ldots & d_{n,m} \end{bmatrix} \qquad (19)$$

Especially, when tendons 1 to l are terminated at the tip of the robot, e.g. cell n, and tendons (l+1) to m are terminated at cell q that is the tip of the proximal section, the matrix in equation 19 is described as, $$D = \begin{bmatrix} d_1 \\ \vdots \\ d_q \\ d_{q+1} \\ \vdots \\ d_n \end{bmatrix} = \begin{bmatrix} d_{1,1} & \ldots & d_{1,l} & d_{1,l+1} & \ldots & d_{1,m} \\ & \vdots & & & \vdots & \\ d_{q,1} & \ldots & d_{q,l} & d_{q,l+1} & \ldots & d_{q,m} \\ d_{q+1,1} & \ldots & d_{q+1,l} & 0 & \ldots & 0 \\ & \vdots & & & \vdots & \\ d_{n,1} & \ldots & d_{n,l} & 0 & \ldots & 0 \end{bmatrix} \qquad (20)$$

where zero components in equation (20) denotes that tendons are terminated at the previous cell. In the same fashion, tendon moment arm matrix D can express the tendon routing for any number of multi-section by placing zero components.

Equation (20) is described as inner product of the tendon moment arm vector $d_i$ and the tension vector $\tau_i^k$ for cell i.

$$\theta_i^k = \frac{1}{K_\theta} d_i \tau_i^k \qquad (21)$$

On the other hand, tension vector $\tau_i^k$ is transformed to $\tau_{\{i+1\}}^k$ by a tension ratio matrix $A_i$, $$\tau_{i+1}^k = A_i \tau_i^k \qquad (22)$$

where the tension ratio matrix $A_i$ is the following diagonal matrix of the tension ratio for each tendon, $$A_i = \begin{bmatrix} \alpha_{i,1}^k & & & 0 \\ & \ddots & & \\ & & \alpha_{i,j}^k & \\ & & & \ddots \\ 0 & & & & \alpha_{i,m}^k \end{bmatrix} \qquad (23)$$

Figure 15:
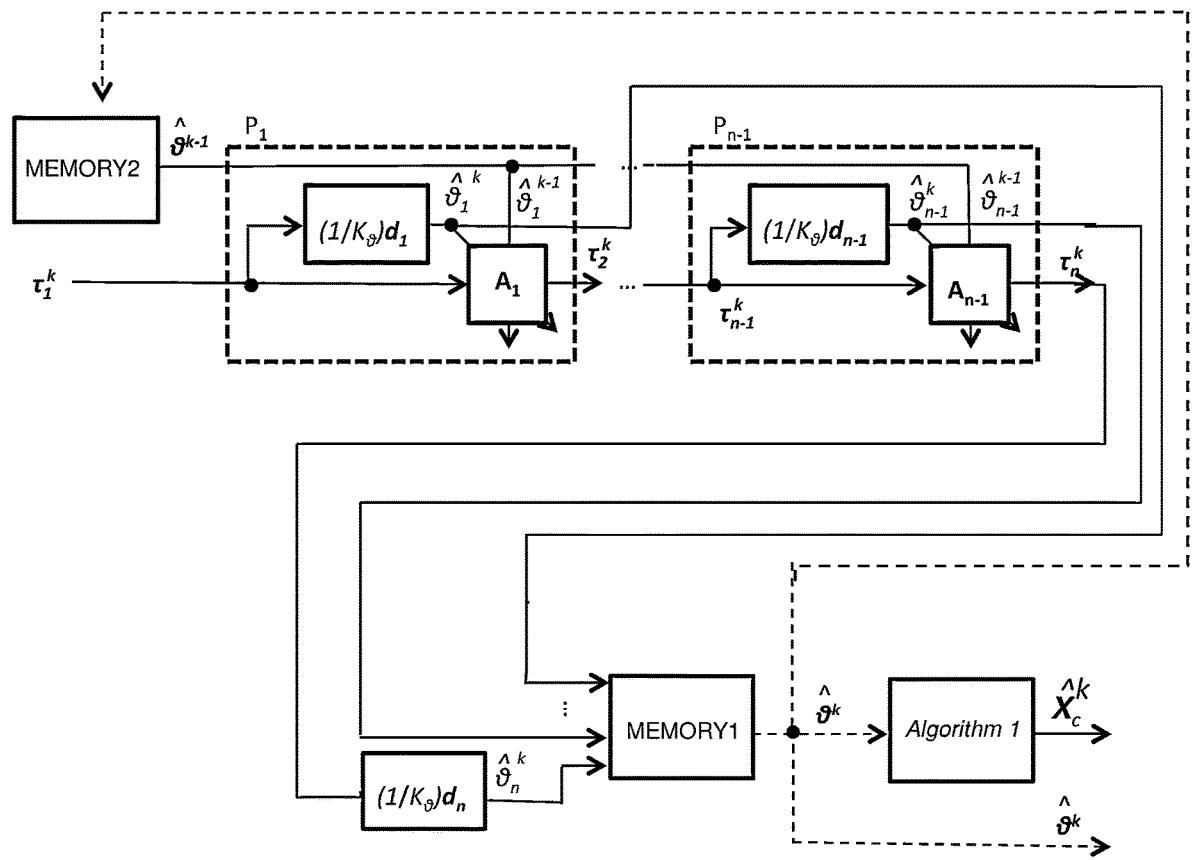
FIG. 15 illustrates an exemplary forward-kinematic-mapping unit.

Finally, the entire forward kinematic mapping is derived from $k_1$ to $\theta^k$ as a block diagram as exemplified in FIG. 15. In this block diagram form, the information flow through the various transformations can be understood or modified. In some embodiments, the block diagram is partitioned differently to distinguish the nature of the transformations. In the exemplary diagram of FIG. 15, the dashed blocks $P_1$ to $P_{n-1}$ with equations (21)-(23) perform mechanics transformations leading to the bending angle $\theta_i^k$ for each cell from the tension vector $\tau_i^k$. This transformation performs in cell-by-cell calculation propagating tension in tendons from the proximal to distal cell. Moreover this transformation includes tension interference at the proximal section that is a general phenomenon about multi-section tendon-driven continuum robot (See Camarillo D B, et al. IEEE Transactions on Robotics. 2009, 25 and Webster R J III, et al. Intl. J. of Robotics Research. 2010, 29(13):1661-1683). The block associated with equation (21) attains this interference using superposition principal of the linear spring system as the inner product calculation. As shown in FIG. 15, $X_c^{\wedge k}$ is a coordinate vector of the robot. The vector $X_c^{\wedge k}$ includes the position and rotation for the frame of each cell based on the task space coordinate.

On the left side of the diagram, the memory 2 block gives the information on bending angles at the previous time k−1. By comparing this information with the present bending angles at time k in the block $A_i$ associated with equation (23), we determine the appropriate direction of the friction force considering the tendon layout even when the robot has an antagonistic pair of tendons. Besides, the mapping can manage a hysteresis of bending angles reached by bending or extending.

Once the bending angle vector $\theta^k$ is determined, the algorithm 1 block transforms this bending angle vector $\theta^k$ to the tip frame $X^k$ of the robot based on the task coordinate. This transformation is the kinematic (geometric) transformation. To attain this transformation in the algorithm b block, we utilize a homogeneous transformation matrix parameterized by the arc parameters in Webster et al, 2010 and applied the matrix for the tip frame of all cells. By multiplying this transformation matrix by cells, the tip position can be determined. Moreover, this transformation gives information of the backbone configuration, which is position of all cells. This feature is advantage for planning for exploration in constrained sensitive cavities to avoid undesirable collisions to the anatomy. Thus, the apparatus as positioned using this transformation provide particularly advantageous function within a patient.

Figure 16:
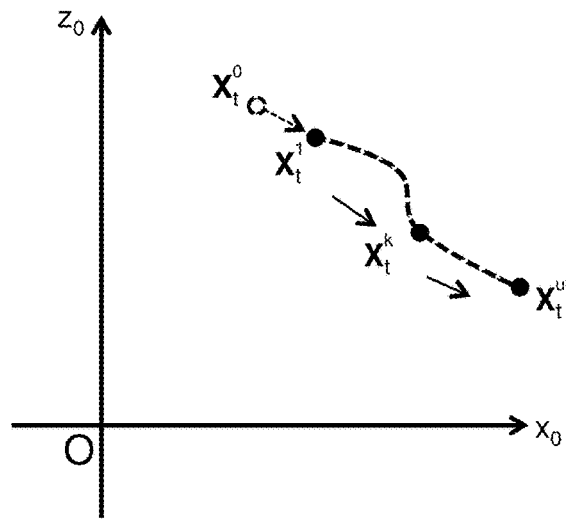
FIG. 16 is a graph showing trajectory generation.

To accomplish higher degree-of-freedom observation tasks, the tip of the continuum robot with an endoscope follows the desired trajectory with the desired observation direction. Thus, there is provided an inverse kinematic mapping. FIG. 16 shows this target trajectory schematically. To identify this trajectory, a set of the target tip frames characterized by $X^k_t$, $Z^k_t$, $\theta^k_t$ at time series k can be defined.

To transform these target tip frames to corresponding actuator parameters for both the continuum robot and the prismatic joint, the target tip frame may be decoupled into the tip frames of the continuum robot $X^k_c$, $Z^k_c$, $\theta^k_c$ and the prismatic joint o, $Z^k_p$, o as follows.

$$\begin{bmatrix} X^k_t \\ Z^k_t \\ \Theta^k_t \end{bmatrix} = \begin{bmatrix} X^k_c \\ Z^k_c \\ \Theta^k_c \end{bmatrix} + \begin{bmatrix} 0 \\ Z^k_p \\ 0 \end{bmatrix} \quad (24)$$

In equation (24), the displacement of the prismatic joint is decoupled from contribution to $X^k_t$ and $\theta^k_t$. Therefore, we can split the entire IKM into two steps, which are the inverse mapping of the continuum robot about $X^k_c$, $\theta^k_c$, and the prismatic joint about $Z^k_p$.

For the continuum robot part, to determine the vector of pull amount of tendons for the target parameters $X^k_t$ and $\theta^k_t$ we initially map the target parameters $X^k_t$ and $\theta^k_t$ to the tension vector of tendons by using the FKM. We define this mapping as a nonlinear optimization problem with the FKM. For a cost function of this optimization problem, we define the following normalized error norm $|E^k_X|$.

$$\|E^k_X\| = \sqrt{(X^k_e/\epsilon_X)^2 + (\Theta^k_e/\epsilon_\theta)^2} \quad (25)$$

where $\epsilon_x$ and $\epsilon_\theta$ are convergence criteria for $X^k_t$ and $\theta^k_t$ and $X^k_e$ and $\theta^k_e$ are residuals based on the target parameters as follow.

$$X^k_e = X^k_c - X^k_t \quad (26)$$

$$\Theta^k_e = \Theta^k_c - \Theta^k_t \quad (27)$$

By using this cost function, we determine the tendon vector $\tau^k_1$ as the values to minimize the error norm in equation (25) as the following optimization problem.

Minimize $\|E^k_X\|$ subject to $(X^k_c, \Theta^k_c) = FKM(\tau^k_1)$ $\tau^k \geq 0$ \quad (28)

This optimization problem may be solved, for example, by the Nelder-Mead Simplex Method (See Lagarias:1998aa) with fminserch function in Matlab. In this method of optimization, all targets except for the target at time 1 have the target at previous time near the target to estimate. Therefore you can find the optimized target successfully by using the tensions at previous target as the initial search values for this algorithm. Moreover, the bending angles at previous time can be set for the bending angles in the memory 2 in FIG. 15 to manage the friction force direction during this optimization calculation. Consequently, by solving the target along the time flow, the solutions include the hysteresis operation property of the continuum robot correctly.

Once the tension vector is determined for the target parameters $X^k_t$, $\theta^k_t$ the vector of pull amount of tendons is calculated by the following equation with assumption A3 and the hinged wire guide structures.

$$\lambda^k = [\lambda^k_1 \ldots \lambda^k_m] = \theta^k D \quad (29)$$

Specifically, in the robot designs as disclosed herein, the moment arm of tendon j for all cell 1 to n are equal. Therefore if we represent the moment arm for each cell as the moment arm at cell 1, the equation (29) can be simplified as follows.

$$\lambda^k = [\Theta^k_c d_{1,1} \ldots \Theta^k_c d_{1,l} \Theta^k_b d_{1,l+1} \ldots \Theta^k_b d_{1,m}] \quad (30)$$

Where $\theta^k_b$ is the bending angle of cell l+1, which is the tip of the proximal section, based on the task coordinate.

The equation (30) gives a physical interpretation for the relation between bending angle and pull amount of tendons. The pull amount of tendons is a function of only the moment arm and the bending angle at the tip where tendons are terminated. The pull amount is independent from any bending angle distribution on the way to the tip, like the uneven curvature by friction force between tendons and eyelets or the bending angle of the intermediate section when the robot has multiple sections.

Figure 17:
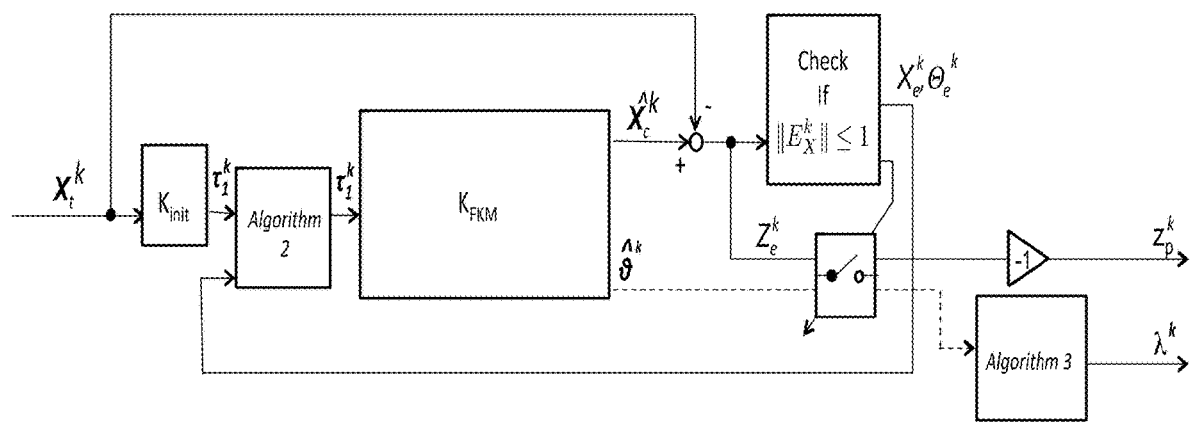
FIG. 17 illustrates an exemplary forward-kinematic-mapping unit.

Finally, the entire inverse kinematic mapping can be derived as shown in the exemplary block diagram form shown in FIG. 17. The inverse kinematic mapping maps the target tip frame $X^k_t$ to the vector of pull amount of tendons $\lambda^k$ and the displacement of the prismatic joint $Z^k_p$. In the diagram, the block $K_{\{FKM\}}$ denotes the FKM in FIG. 15. The algorithm 2 associated with equation (28) executes the iterative calculation to minimize the error norm in (28). When this minimized norm is less than or equal to 1, the bending angles calculated by the FKM is used to determine the vector of pull amount of tendons in the algorithm 3 block associated with equation (30). On the other hand, the displacement of the prismatic joint is calculated from the residual $Z^k_e$, which is defined as $Z^k_c - Z^k_t$, based on equation (24).

The target at time 1 does not have the target at previous time before time 1. Therefore, the appropriate initial tension vector for the optimization calculation is not available for time 1. This initial tension vector is provided by the block $K_{init}$ on the left side in the diagram. To generate this initial values in the block $K_{init}$ we use the conventional piece-wise-constant approximation (PCCA) for the inverse kinematics. The closed-form geometric approach for the inverse kinematics is given for single and multiple sections with known tip position of each multi-sections. However, instead of tip position of sections, we map the tip position and the direction to the bending angle of two bending sections. Assuming that the continuum robot has two bending sections with constant curvature in the task coordinate in FIG. 14, we derive the following equation to relate the tip frame of the robot and the curvature of the distal bending section.

$$X_t = \frac{(2\kappa_2 s - \Theta_t)\cos(\kappa_2 s - \Theta_t) - (\kappa_2 s - \Theta_t)\cos(\Theta_t) - \kappa_2 s}{\kappa_2(\kappa_2 s - \Theta_t)} \quad (31)$$

where s is length of the one section and $\kappa_2$ is curvature of the distal bending section.

By solving equation (31) numerically, the curvatures for two bending sections are determined from the tip frame of the robot. The tension vector for these determined curvatures can be calculated by using the similar constitution equation to equation (1).

Increased Precision for Attitude Estimation

The first embodiment involves deriving an equation regarding equilibrium between force and moment, based on assumptions A1 through A5, and solving the equation to obtain the angle $\theta_i$ of each division. However, if the body 1 bends greatly these assumptions do not hold as well, and estimation error of the attitude increases. For example, assumption A3 assumes that the inclined angle of the tendon 2 as to the body arm 1 is small. Accordingly, equation (1) does not take into consideration bending moment around the divisions due to normal force $N_{i+1,j}$. However, if the body 1 bends greatly the inclined angle of the tendon 2 increases, and the normal force $N_{i+1,j}$ increases as can be seen in equation (2). The moment due to the normal force $N_{i+1,j}$ acts to increase the angle $\theta_i$, so the angle $\theta_i$ estimated according to the method described in the first embodiment, which does not take this moment into consideration, will be smaller than the actual value.

The first embodiment also involves approximating $(\theta_i/2)$ which is the inclined angle of the adjacent tendon 2 as to the $\sin(\theta_{i+1}/2)$ to be equal, so as to solve the simultaneous equations of equations (2), (4), and (5). However, in an actual robot, the closer to the tip of the body 1 is, the smaller the angle $\theta_i$ is due to the influence of friction, as illustrated in FIG. 12. In addition, the moment equilibrium equation in equation 1 does not take into consideration the influence of reactive force imparted by an adjacent division. This approximation also is a factor in degrading the estimation precision of attitude. Thus, while the first and second embodiments as discussed above provide a novel and useful estimation, increased precision can be attained for attitude estimations when one or more of the normal force $N_{i+1,j}$, inclined angle, and/or reactive force imparted by an adjacent division are also taken into account.

Third Embodiment

Figure 21:
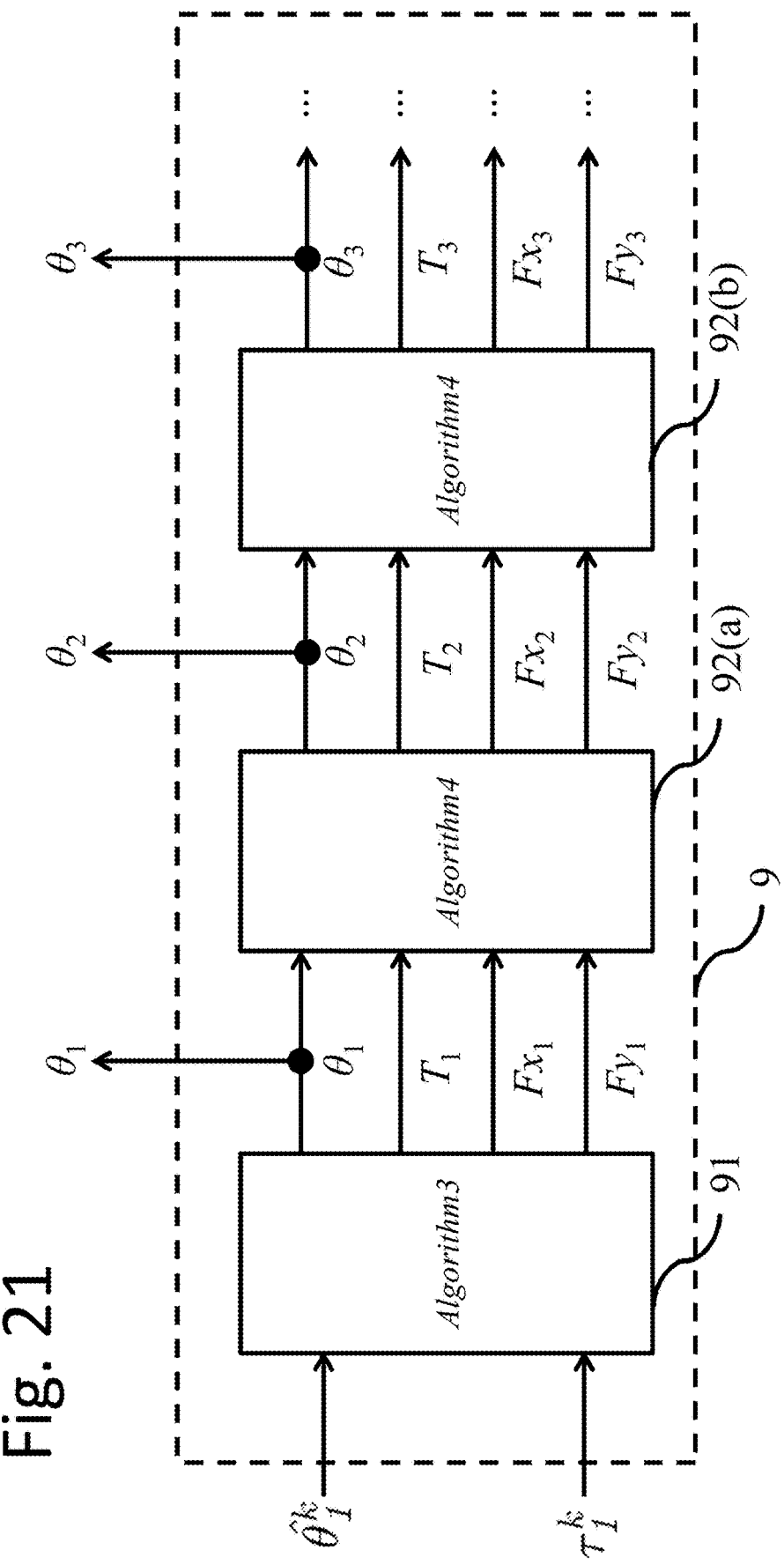
FIG. 21 is a block diagram illustrating the forward-kinematic-mapping unit 9 according to several embodiments.

Accordingly, the present embodiment derives a forward-kinematic-mapping unit 9 with less approximation and more precise attitude estimation as compared to the first embodiment. FIG. 21 is a block diagram illustrating the forward-kinematic-mapping unit 9 according to the present embodiment. This forward-kinematic-mapping unit 9 includes a computing unit 91 configured to compute the angle $\theta_1$, tensile force $T_1$, and reactive forces $Fx_1$ and $Fy_1$ of the division 1, based on an initial value $\hat{\theta}_1^k$ of an angle estimation value and tensile force $\tau_1^k$ at the proximal end of the division 1, and computing units 92 configured to compute the angle $\theta_{i+1}$, tensile force $T_{i+1}$, and reactive forces $Fx_{i+1}$ and $Fy_{i+1}$ of the division i+1, based on the angle $\theta_i$, tensile force $T_i$, and reactive forces $Fx_i$ and $Fy_i$ of the division i. In the present embodiment, first, an equilibrium equation of force and moment is derived which takes into consideration the inclination of the tendon 2 as to the longitudinal direction of each division, and the reactive force imparted from an adjacent division. The force and moments acting on the tip side division can be obtained by solving the simultaneous equations with the force and moments acting on the base side division as known values. Note however, that numerical solutions are computed using iterative calculation, since analytical solving of the simultaneous equations according to the present embodiment is difficult.

FIG. 22 illustrates a coordinates system of a robot according to the present embodiment. FIG. 22(a) represents force and moment acting on division i, and FIG. 22(b) represents force acting on tendon 2 at a point of contact Pi of the division i and tendon 2. In FIGS. 22(a) and (b), frictional force $f_{i+1}$ and normal force $N_{i+1}$ represent the frictional force and normal force acting between the division i and tendon 2, and tensile forces $T_i$, $T_{i+1}$ represent the tensile forces acting in the proximal end and the distal end of the tendon 2. Further, of the reactive forces acting upon the division i from the division i−1, the component in the longitudinal direction of the division i is represented by $Fx_i$, and the radial direction component as $Fy_i$. In the same way, of the reactive forces acting upon the division i from the division i+1, the component in the longitudinal direction of the division i+1 is represented by $Fx_{i+1}$, and the radial direction component as $Fy_{i+1}$. Moreover, the relative angle on the longitudinal direction between division i−1 and division i is represented by the angle $\theta_i$, and number of divisions by n, the length of each division by 2l, and moment arm by d, the bending stiffness of a division by k, and the friction coefficient between a division and tendon 2 by $\mu$.

An equilibrium equation between force and moment acting on each division is derived. FIG. 22(c) illustrates force and moment acting on the proximal end and division 1. It can be seen from FIG. 22(c) that resistive forces $Fx_1$ and $Fy_1$, and moment $M_1$ act between the division 1 and the proximal end. Accordingly, an equilibrium equation between force and moment at the proximal end has to be derived in order to obtain these resistive forces and moment. Accordingly, the proximal end is conceived of being part of the body 1 in the present embodiment, and this is taken as division o to derive the equilibrium equation between force and moment. Note however, that boundary conditions are difference between the division o and all other divisions. Accordingly, cases where i≥1 and where i=o will be handled separately.

First, an equilibrium equation will be derived for a case where i≥1. From FIG. 22(a), the force equilibriums for the longitudinal direction and radial direction of division i is described by equations (32) and (33), respectively.

$$-Fx_{i+1}\cos(\theta_{i+1}) + Fy_{i+1}\sin(\theta_{i+1}) + Fx_i - f_{i+1} = 0 \quad (32)$$

$$-Fx_{i+1}\sin(\theta_{i+1}) - Fy_{i+1}\cos(\theta_{i+1}) + Fy_i N_{i+1} = 0 \quad (33)$$

Taking the counterclockwise direction as forward, the equilibrium equation of moment centered on $O_i$, which is the base side endpoint of the division i is described by equation (34) using the bending moment $M_i$ of the division i.

$$-M_i + M_{i+1} + df_{i+1} + 1N_{i+1} - 2l\{Fx_{i+1}\sin(\theta_{i+1}) + Fy_{i+1}\cos(\theta_{i+1})\} = 0 \quad (34)$$

In a case where i≥1, the moment $M_i$ is described by equation (35) using angle $\theta_i$ and bending stiffness k, thus yielding equation (36) by substituting equation (35) into equation (34).

$$M_i = k\theta_i \tag{35}$$

$$-k\theta_i + k\theta_{i+1} + df_{i+1} + 1N_{i+1} - 2l\{Fx_{i+1}\sin(\theta_{i+1}) + Fy_{i+1}\cos(\theta_{i+1})\} = 0 \tag{36}$$

Also, from FIG. 22(a), the equilibrium equations for the forces in the $Fx_i$ direction and $Fy_i$ direction acting on the tendon 2 are described in equations (37) and (38).

$$T_{i+1}\sin\left(\frac{\theta_{i+1}}{2}\right) + T_i\sin\left(\frac{\theta_i}{2}\right) - N_{i+1} = 0 \tag{37}$$

$$T_{i+1}\cos\left(\frac{\theta_{i+1}}{2}\right) - T_i\cos\left(\frac{\theta_i}{2}\right) + f_{i+1} = 0 \tag{38}$$

Further, assuming Coulomb friction between the tendon 2 and division in the same way as the first embodiment yields equation (39).

$$f_{i+1} = \mu N_{i+1} \tag{39}$$

Note however, that equations (37) through (39) are identical to equations (2) through (4) according to the first embodiment, except that the suffixes of the normal force $N_{i+1}$ and the friction force $f_{i+1}$ are different.

$\theta_i$, $T_i$, $Fx_i$, and $Fy_i$ are known values in the equilibrium of division i described in equations (32), (33), and (36) through (39), so the number of unknowns is the six of $N_{i+1}$, $f_{i+1}$, $\theta_{i+1}$, $T_{i+1}$, $Fx_{i+1}$, and $Fy_{i+1}$. The number of unknowns is thus the same as the number of independent equations, so all unknowns can be found be solving the simultaneous equations of (32), (33), and (36) through (39).

First, the right side and the left side of equation (37) are each divided by the right side and the left side of equation (38), and further equation (39) is substituted into equation (38) to eliminate the friction force $f_i$, which yields equation (40).

$$\tan\left(\frac{\theta_{i+1}}{2}\right) + \frac{N_{i+1} - T_i\sin\left(\frac{\theta_i}{2}\right)}{\mu N_{i+1} - T_i\cos\left(\frac{\theta_i}{2}\right)} = 0 \tag{40}$$

Further, equations (39) and (33) are substituted into equation (36) to eliminate the reactive forces $Fx_{i+1}$ and $Fy_{i+1}$ and $f_{i+1}$, which yields equation (41).

$$N_{i+1} = \frac{k}{l - \mu d}\theta_{i+1} - \frac{2lFy_i + k\theta_i}{l - \mu d} \tag{41}$$

Equation (41) is substituted into equation (40) to eliminate the normal force $N_{i+1}$, which allows equation (42), which includes only the angle $\theta_{i+1}$ as an unknown, to be derived.

$$\tan\left(\frac{\theta_{i+1}}{2}\right) + \frac{(k\theta_{i+1} - 2lFy_i - k\theta_i) - (l - \mu d)T_i\sin\left(\frac{\theta_i}{2}\right)}{\mu(k\theta_{i+1} - 2lFy_i - k\theta_i) - (l - \mu d)T_i\cos\left(\frac{\theta_i}{2}\right)} = 0 \tag{42}$$

However, equation (42) contains a tangent having the unknown $\theta_{i+1}$ as a parameter, so analytical solution is not easy. Accordingly, in the present embodiment, a numerical solution is obtained for the angle $\theta_{i+1}$ by iterative calculation using Newton's method. If the angle $\theta_{i+1}$ at the m'th iterative calculation is described as $\theta_{i+1}{}^m$, the m'th computation result is described as equation (43).

$$\theta_{i+1}^{m+1} = \theta_{i+1}^m - \frac{H(\theta_{i+1})}{H'(\theta_{i+1})} \tag{43}$$

The function $H(\theta_{i+1})$ in equation (43) is the left side of equation (42). The function $H'(\theta_{i+1})$ is the derivative of the angle $\theta_{i+1}$ of the function $H(\theta_{i+1})$, and is described in equation (44).

$$H'(\theta_{i+1}) = \frac{1}{2\cos^2\left(\frac{\theta_{i+1}}{2}\right)} + \frac{k(l - \mu d)T_i\left\{\mu\sin\left(\frac{\theta_i}{2}\right) - \cos\left(\frac{\theta_i}{2}\right)\right\}}{\left\{\begin{array}{c}\mu(k\theta_{i+1} - 2lFy_i - k\theta_i) - \\ (l - \mu d)T_i\cos\left(\frac{\theta_i}{2}\right)\end{array}\right\}^2} \tag{44}$$

The angle $\theta_{i+1}$ is then updated using equations (42) through (44) until the function $H(\theta_{i+1})$ is a sufficiently small positive number $\varepsilon_H$ or smaller. Note that in the present embodiment, the initial value $\theta_{i+1}{}^1$ for iterative calculation is set to the angle $\theta_i$ of division i. The reason is that the number of times of iterative calculations necessary for convergence can be reduced by using the angle $\theta_i$ of an adjacent division as the initial value, since the angle $\theta_i$ of each division gradually changes from the proximal end to the distal end.

The angle $\theta_{i+1}$ after convergence is substituted into equation (41) to compute the normal force $N_{i+1}$, and the normal force $N_{i+1}$ is substituted into equation (39) to obtain the friction force $f_{i+1}$. The angle $\theta_{i+1}$ and normal force $N_{i+1}$ are substituted into equation (37) to obtain the tensile force $T_{i+1}$. The angle $\theta_{i+1}$, normal force $N_{i+1}$, and tensile force $T_{i+1}$ are substituted into equations (32) and (33) to calculate the link reactive forces $Fx_{i+1}$ and $Fy_{i+1}$.

Next, an equilibrium equation for division o where i=o, and a method for computing a numerical solution, will be described. First, in the present embodiment, division o is assumed to be a stiff body, so the angle $\theta_o$ is o.

$$\theta_0 = 0 \tag{45}$$

Thus, at the proximal end of division o the tendon 2 is parallel to division o as illustrated in FIG. 22(c), so the tensile force $\tau_1{}^k$ at the base acts in the longitudinal direction of the division o. Also, if the entire body 1 including the division o is considered to be a rigid body system, the only external force acting on the system is the tensile force $\tau_1{}^k$, and the reactive forces $Fx_o$ and $Fy_o$ acting on the division o. The sum of force from external force and moment is 0 in a case of equilibrium between force and moment, so the reactive forces $Fx_o$ and $Fy_o$ and moment $M_o$ are described in equations (46) through (48).

$$Fx_0 = \tau_1{}^k \tag{46}$$

$$Fy_0 = 0 \tag{47}$$

$$M_0 = \tau_1{}^k d \tag{48}$$

Substituting equations (45) through (48) into equations (32), (33), and (36) through (38), yields equilibrium equations (49) through (53) for division o.

$$T_1 \sin\left(\frac{\theta_1}{2}\right) - N_1 = 0 \quad (49)$$

$$T_1 \cos\left(\frac{\theta_1}{2}\right) - \tau_1^k + f_1 = 0 \quad (50)$$

$$-Fx_1 \cos(\theta_1) + Fy_1 \sin(\theta_1) + \tau_1^k - f_1 = 0 \quad (51)$$

$$-Fx_1 \sin(\theta_1) - Fy_1 \cos(\theta_1) + N_1 = 0 \quad (52)$$

$$-\tau_1^k d + k\theta_1 + df_1 + lN_1 - 2l\{Fx_1 \sin(\theta_1) + Fy_1 \cos(\theta_1)\} = 0 \quad (53)$$

The simultaneous equations (39) and (49) through (53) are solved using the same method as for the case where $i \geq 1$ with the tensile force $\tau_1^k$ as a known value, thus obtaining the unknowns $\theta_1$, $T_1$, $Fx_1$, and $Fy_1$. First, equation (49) is divided by equation (50), and the friction force $f_1$ is eliminated using equation (39), which yields equation (54).

$$\tan\left(\frac{\theta_1}{2}\right) + \frac{N_1}{\mu N_1 - \tau_1^k} = 0 \quad (54)$$

Also, equations (39) and (52) are substituted into equation (53) to eliminate link reactive forces $Fx_1$ and $Fy_1$ and friction force $f_1$, which yields equation (55).

$$N_1 = \frac{k\theta_1 - \tau_1^k d}{l - \mu d} \quad (55)$$

Further, equation (55) is substituted into equation (54) to eliminate the normal force $N_i$, allowing equation (56), which includes only the angle $\theta_1$ as an unknown, to be derived.

$$\tan\left(\frac{\theta_1}{2}\right) + \frac{k\theta_1 - \tau_1^k d}{\mu k \theta_1 - \tau_1^k l} = 0 \quad (56)$$

However, analytical solution of equation (56) is not easy, for the same reason as equation (43). Accordingly, a numerical solution is obtained equation (56) using Newton's method. If the angle $\theta_1$ at the m'th iterative calculation is described as $\theta_1^m$, the m'th computation result is described as equation (57).

$$\theta_1^{m+1} = \theta_1^m - \frac{G(\theta_1^m)}{G'(\theta_1^m)} \quad (57)$$

The function $G(\theta_1)$ is the left side of equation (56). The function $G'(\theta_1)$ is the derivative of the angle $\theta_1$ of the function $G(\theta_1)$, and is described in equation (58).

$$G'(\theta_1) = \frac{1}{2\cos^2\left(\frac{\theta_1}{2}\right)} + \frac{(\mu d - l)k\tau_1^k}{\{\mu k \theta_1 - \tau_1^k l\}^2} \quad (58)$$

Note that the initial value $\theta_i^1$ for iterative calculation in equation (57) is the output $\hat{\theta}_1^k$ of the initial-value-generating unit 11, in the present embodiment.

The angle $\theta_{i+1}$ after convergence is substituted into equations (39) and (49)-(53), whereby the unknowns $T_1$, $Fx_1$, and $Fy_1$ are obtained in the same way as in the case of $i \geq 1$.

Figure 23A:
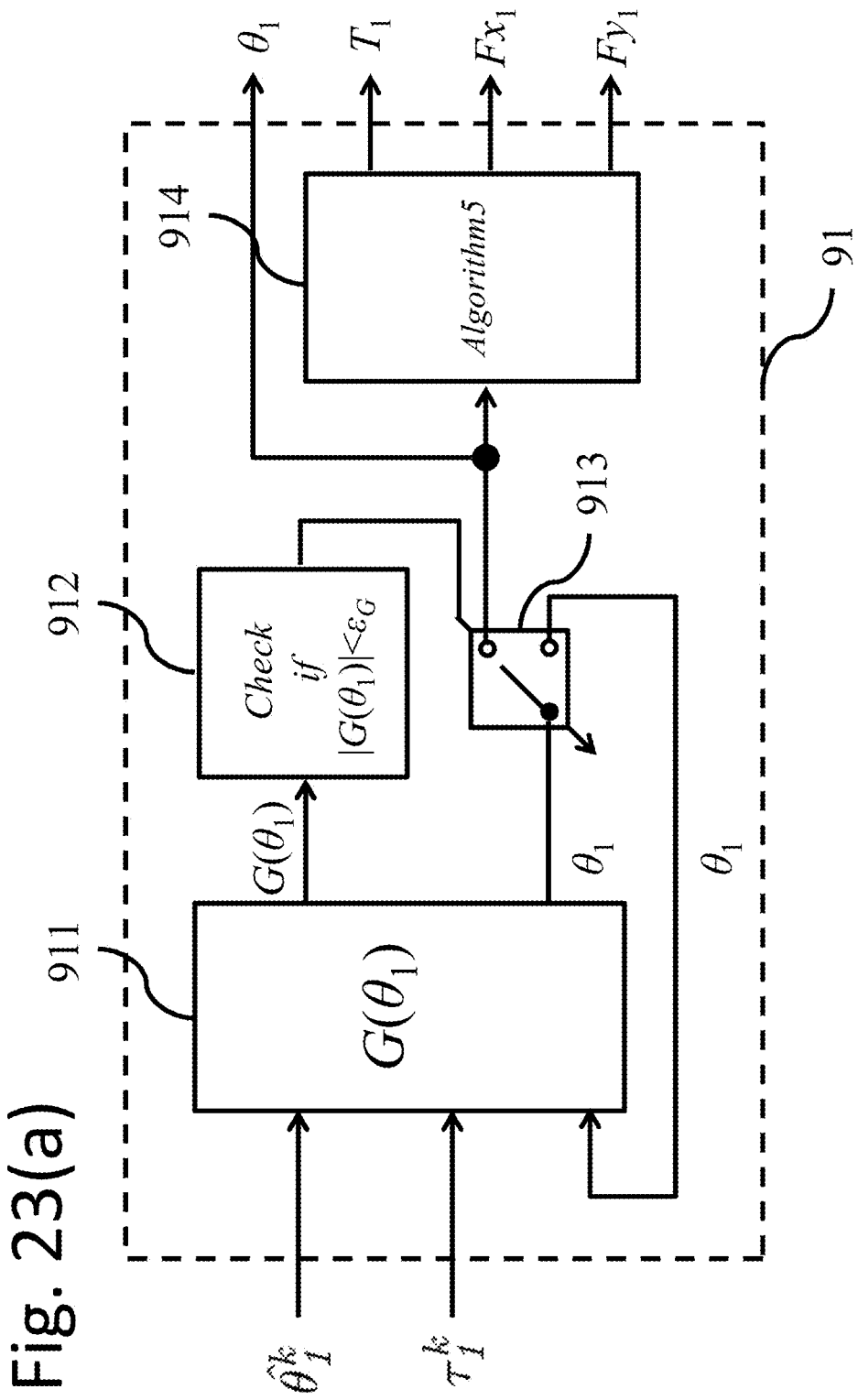
FIGS. 23(a) and 23(b) are block diagrams of the computing units 91 (FIG. 23(a)) and 92 (FIG. 23(b)) that compute the functions $G(\theta_1)$ and $H(\theta_{i+1})$, respectively.
Figure 23B:
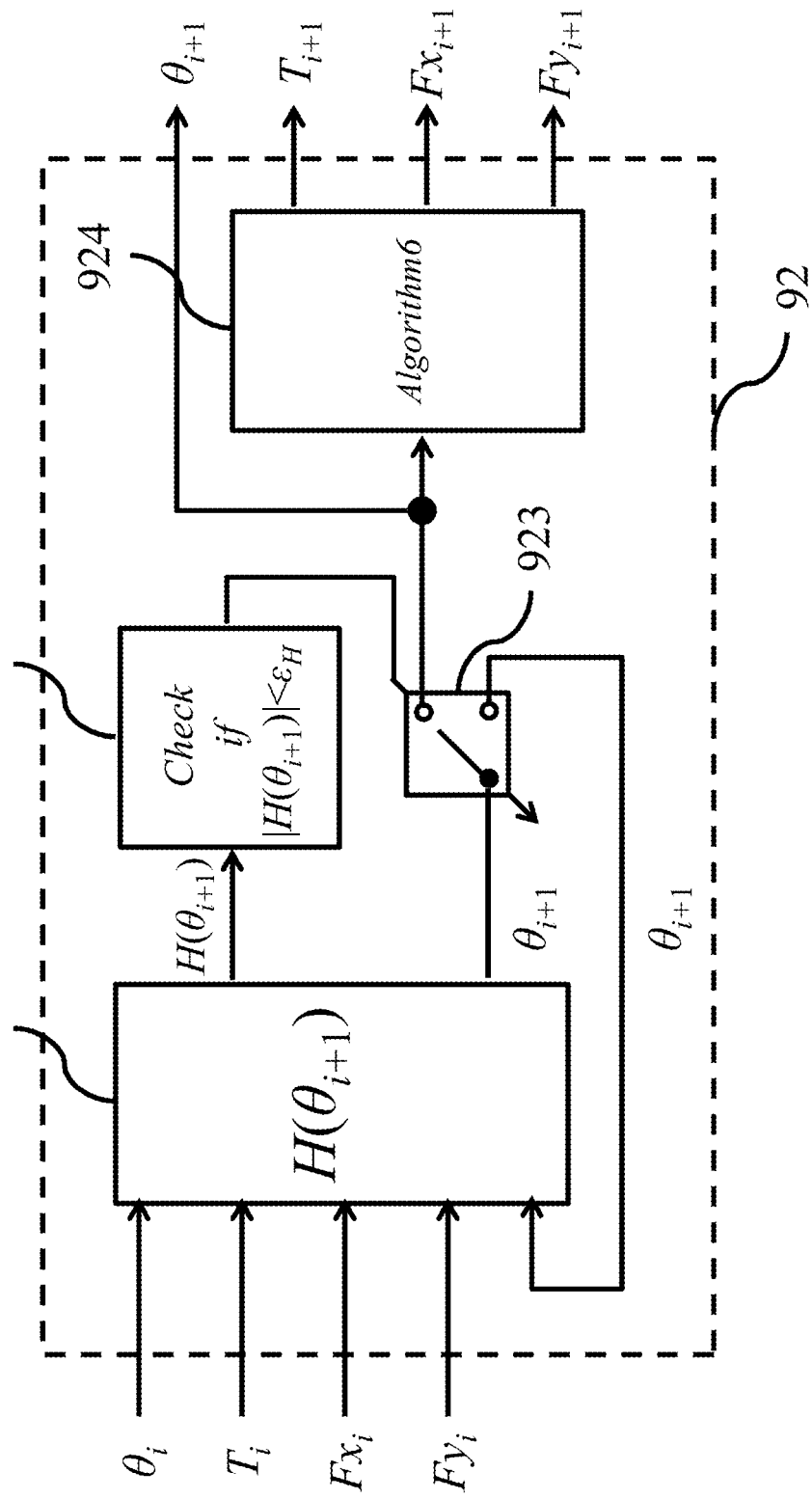

FIGS. 23(a) and (b) are block diagrams of the computing units 91 and 92. A computing unit 911 in FIG. 23(a) computes the function $G(\theta_1)$ using equation (56), and a checking unit 912 outputs a command to a switch 913 to output the angle $\theta_1$ if the function $G(\theta_1)$ is not greater than a threshold value $\varepsilon_G$. A computing unit 914 calculates the unknowns $T_1$, $Fx_1$, and $Fy_1$ using the angle $\theta_1$. The computing unit 921, checking unit 922, switch 923, and computing unit 924 illustrated in FIG. 23(b) respectively correspond to the computing unit 911, checking unit 912, switch 913, and computing unit 914, of the computing unit 91, and perform the same computing processing.

Calculation of Numeric Values According to Third Embodiment

This section illustrates an example of calculation of numerical values using the forward-kinematic-mapping-unit 9 designed in the previous section. In the present embodiment, the length l of a division is set to 0.5 mm, the number of divisions n is 30, the moment arm d is 0.7 mm, the friction coefficient is 0.33, and stiffness k is 0.2 Nmm/rad.

Figure 24A:
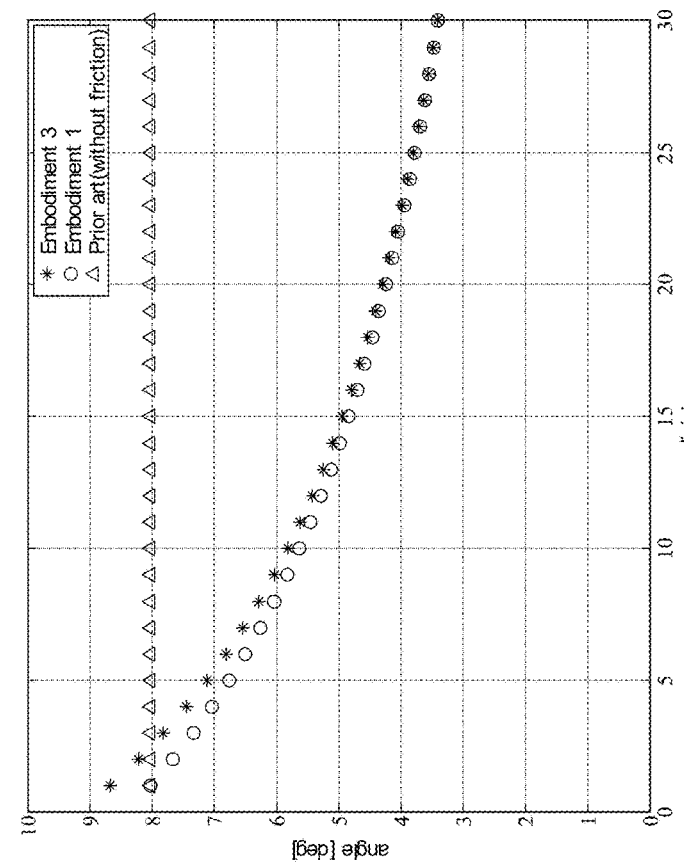
FIGS. 24(a) and 24(b) are charts that respectively illustrate the tensile force $T_i$ and angle $\theta_i$, for each division with the tensile force $\tau_1^k$ at the proximal end set to 0.4 N.

FIGS. 24(a) and (b) respectively illustrate the tensile force $T_i$ and angle $\theta_i$, for each division with the tensile force $\tau_1^k$ at the proximal end set to 0.4 N. In FIG. 24, the asterisks, circles, and triangles respectively represent response according to the method of the present embodiment, the method of the first embodiment, and the related art where friction is not taken into consideration. This is the same in the subsequent drawings as well. It can be seen from FIG. 24(a) that the closer the divisions are to the tip, the lower the tensile force $T_i$ is in the present embodiment and first embodiment. On the other hand, the tensile force $T_i$ is the same at all divisions in the related art. This is because the present embodiment and the first embodiment take into consideration loss of tensile force $T_i$ due to friction force between the tendon 2 and the divisions. The tensile force in the method according to the present embodiment is smaller than the tensile force according to the first embodiment at all divisions. This is because the present embodiment takes into consideration loss of tensile force due to friction force when computing the tensile force $T_1$ of division 1 from the tensile force $\tau_1^k$ at the proximal end.

Figure 24B:
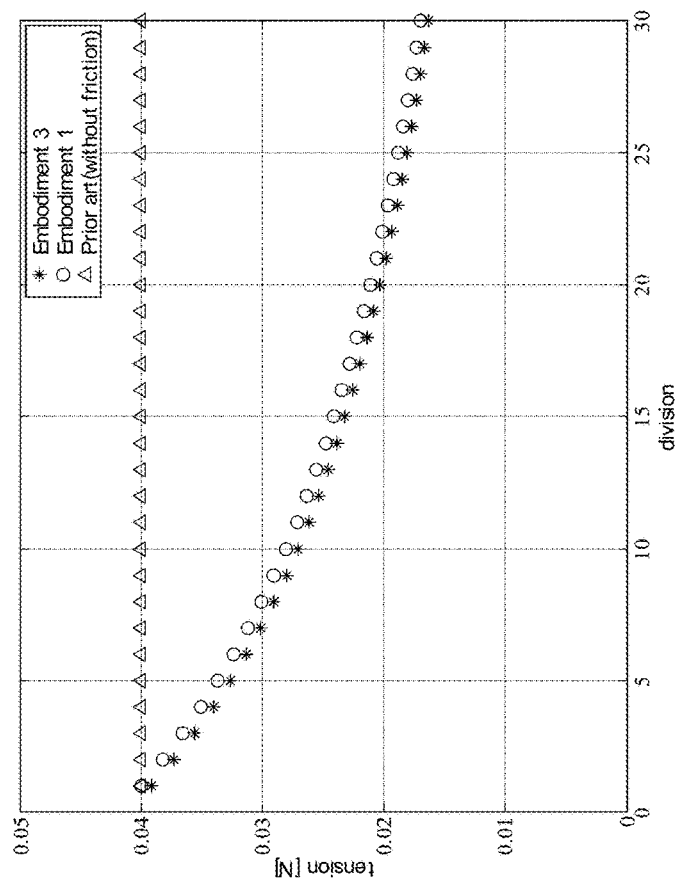

It can be seen from FIG. 24(b) that whereas the angle $\theta_i$ is the same for all divisions in the related art, the closer the divisions are to the tip, the smaller the angle $\theta_i$ is in the present embodiment and first embodiment. This is because whereas the tensile force $T_i$ is the same in the related art, the closer the divisions are to the tip, the lower the tensile force is in the present embodiment and first embodiment. It can also be seen that the angle $\theta_i$ according to the present embodiment is greater than the angle $\theta_i$ in the first embodiment with regard to divisions 1 through 20. This is because the method according to the present embodiment takes into consideration moment due to normal force. On the other hand, the angles match well in the present embodiment and first embodiment, with regard to divisions 1 through 20. The reason is that the effects of moment due to normal force are relatively smaller at division toward the tip where the angle $\theta_i$ is smaller, since the normal force $N_i$ is proportionate to the angle $\theta_i$, as shown in equations (2) and (37).

Figure 25:
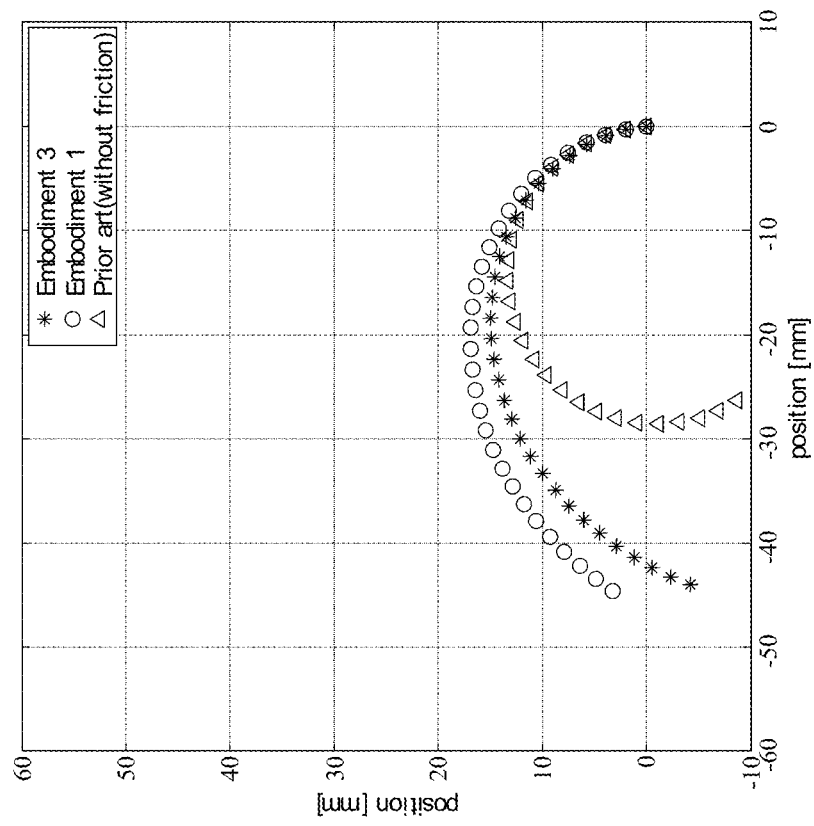
FIGS. 25 (a), (b), and (c) illustrate the tip position of each division with the tensile force $\tau_1^k$ at the base set to 0.1 N, 0.2 N, and 0.4 N. Note that in FIG. 25, the point of origin is the proximal end, and the vertical direction in these drawings in the longitudinal direction of division o.

FIGS. 25(a), (b), and (c) illustrate the tip position of each division with the tensile force $\tau_1^k$ at the base set to 0.1 N, 0.2 N, and 0.4 N. Note that in FIG. 25, the point of origin is the proximal end, and the vertical direction in these drawings in the longitudinal direction of division o. It can be seen from FIGS. 25(a), (b), and (c) that the difference in attitude between the present embodiment and the first embodiment is small when the tensile force $\tau_1^k$ is 0.1 N, but the difference in attitude increases as the tensile force increases to 0.2 N and to 0.4 N. This is because the larger the angle $\theta_i$ is, the greater the moment due to normal force $N_i$ is, as described earlier. Accordingly, the method according to the present embodiment has to be used for estimating the attitude of the body 1 with high precision in cases where the angle $\theta_i$ is great. On the other hand, when the tensile force $\tau_1^k$ is 0.1, the difference between the attitude of the related art and the attitude of the present embodiment and first embodiment is marked, but the difference between the attitude of the present embodiment and the attitude of the first embodiment is small, as can be seen from FIG. 25(*a*). Accordingly, the method according to the first embodiment may be used when the angle $\theta_i$ is small.

Fourth Embodiment

The attitude estimation method according to the third embodiment enables the attitude to be estimated with high precision as compared to the first embodiment even when the angle $\theta_i$ is great. However, the angle $\theta_i$ is calculated by iterative calculation as shown in equations (49) and (54), so the calculation time increases if the number of divisions increases. Also, if the angle $\theta_i$ is small, the difference in attitude as calculated by the methods according to the first and third embodiments is small, as can be seen from FIG. 25(*a*). According to the present embodiment, in a case where the target angle $\Theta_n^k$ is equal to or above a threshold $\varepsilon_s$ the method according to the third embodiment, which is more precise, is used, and in a case where the target angle $\Theta_n^k$ is below the threshold $\varepsilon_s$ the method according to the first embodiment, which uses fewer calculations, is used. Thus, the calculation load can be reduced.

Figure 26:
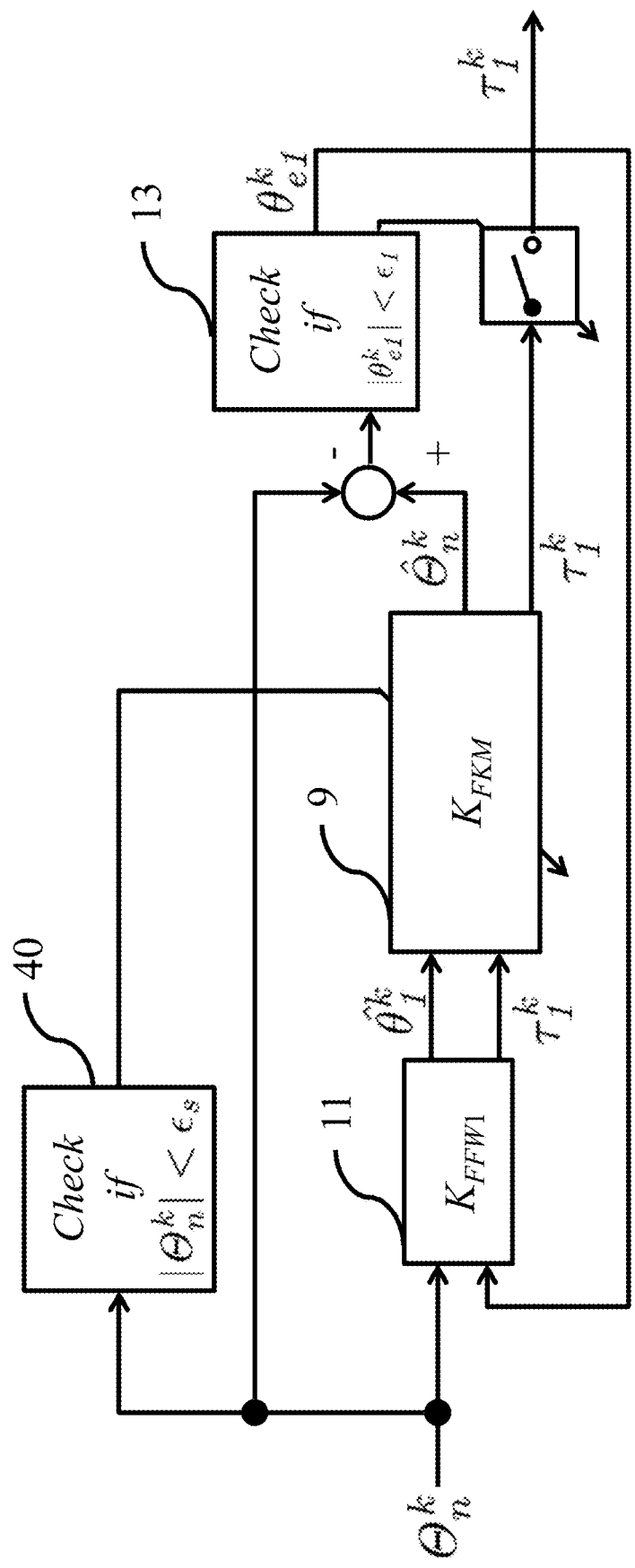
FIG. 26 is a block diagram illustrating a control apparatus according to several embodiments.

FIG. 26 is a block diagram illustrating a control apparatus according to the present embodiment. The control apparatus differs from that in the first embodiment with regard to the point at a checking unit 40 is included. The checking unit 40 instructs the forward-kinematic-mapping unit 9 to calculate the angle estimation value $\hat{\Theta}_n^k$ using the method according to the first embodiment in a case where the target angle $\Theta_n^k$ is below the threshold $\varepsilon_s$, and using the method according to the third embodiment in a case where the target angle $\Theta_n^k$ is equal to or greater than the threshold $\varepsilon_s$.

Friction Modification

In embodiments as discussed above, friction is presumed to be constant. However, friction is not constant and may change according to various environmental conditions such as the running time of the device, abrasion, fitting, surface oxidation, environment, humidity, and temperature. Thus, in some embodiments, the equations as discussed herein are solved using a latest and/or current value for the friction coefficient. This friction coefficient can be determined by understanding the relationship between the angular direction at the tip and the length the tendon was pulled to create the angular direction.

Surprisingly, in a tendon-driven apparatus, the direction of the tip, or of the top cell within a section that is controlled by one or more tendons (e.g., in a multi-segment apparatus) is dependent on the length the tendon was pulled and is not affected by the posture of the middle section or sections of the apparatus. Thus, an apparatus with a distal tip angle $\theta_{tip}$ will have the same pulled tendon length $L_x$ regardless of whether the apparatus contains a single curve to provide the $\theta_{tip}$ angle or is in an "S" shape where the angle at the tip is $\theta_{tip}$.

To describe these embodiments, a parallel curves characteristic is provided and used to calculate the direction of the tip. The parallel curve characteristic describes the relationship between (i) the angular difference between an end direction and a tip direction wherein each of two parallel tendon have the same end direction and tip direction, and (ii) the difference between the first curved end position and the second curved line end position.

For example, in an apparatus having two tendons, when one tendon located in a first position in the device is pulled a length L, the second tendon located in a second position is pulled in reverse by the same length L to effect a curve in the apparatus such that the direction of the tip of the device (or the top cell within a division controlled by the tendon) is $\theta$. Thus, the difference between the two tendons is 2 L. The directions of all top cells (the location of the tendon in the first position) in all sections are determined by the each amount of pulling tendon (L). In this embodiment, each tendon is connected to each top cell. This is not affected by any posture of the middle part of the device. In this embodiment, it is assumed that the tendons run parallel to the axis of the device and that the stretch of the strings can be ignored. The process as discussed above can be applied as well for apparatus with multiple sections and/or sections with different lengths.

This can be described as discussed above in Equation (44) which gives a physical interpretation for the relation between bending angle and pull amount of tendons, where the pull amount of tendons is described as a function of only the moment arm and the bending angle at the tip where tendons are terminated.

In a first exemplary calculation, where only a single wire is present, it is assumed that, with a tension applied to the tendon of T and a friction coefficient of $\mu_1$, the direction of the tip can be calculated with equation (45)

$$\theta_1 = FKM(T, \mu 1) \tag{59}$$

where FKM is the forward kinematic mapping as described above. In this embodiment, the current friction coefficient, $\mu$ is described as:

$$\mu = \mu_1 + \delta\mu \tag{60}$$

The direction of the tip can then be calculated with the assumption when a tension is T, as $$\theta_2 = FKM(T, \mu_1 + \delta\mu) \tag{61}$$

The direction of the tip with the tendon moment arm d:

$$\theta = \lambda/d \tag{62}$$

is calculated based on the parallel curves characteristic where the tendon pulling displacement is $\lambda$. This calculation is based on equation (30). As discussed above, this equivalence is independent of any internal directions of the apparatus. From this information the latest or current friction coefficient can be estimated using the equation:

$$\mu = \mu 1 + \delta\mu * (\theta - \theta_1)/(\theta_2 - \theta_1) \tag{63}$$

Figure 28:
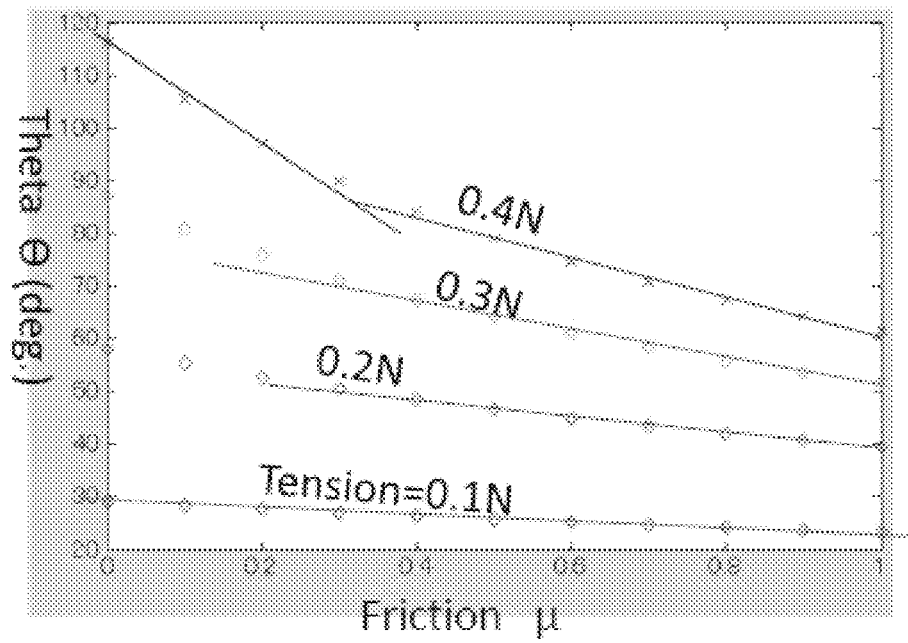
FIG. 28 is a chart providing the angle (θ) versus friction for different tension in the tendon.
Figure 29:
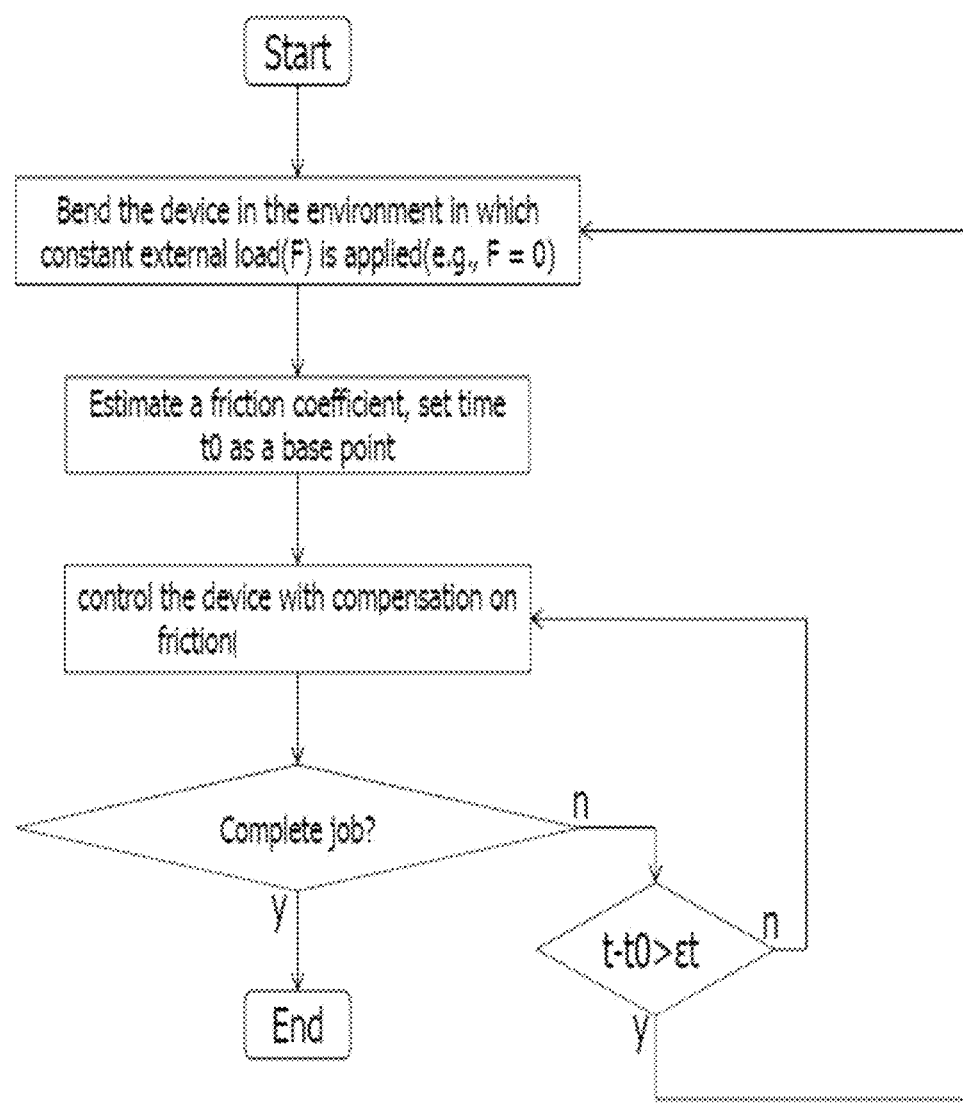
FIG. 29 is a flow chart for workflow in one embodiment of the invention.

In some embodiments, the equation (63) is valid. In others, it may be calculated as a curve with the three or more points ($\theta_1$, $\theta_2$, $\theta_3$ . . . ), with the equation adapted as appropriate. In these embodiments, the graph shown in FIG. 28 may be used as a reference.

The device can be bent in an environment in which no external load is applied to the device. The distance between a centroid of the device (See 7 of FIG. 7(*b*)) and a tendon is described by the distances $d_1$, $d_2$, $d_3$, and $d_4$ of FIG. 7(*b*). It can also be important to know the bending rigidity, or bending stiffness of a restoring element. This is depicted as $K_\theta$ in FIG. 1(*c*), 33). The length of the restoring element of the apparatus is L.

In another embodiment, the calculations are provided for determining the friction coefficient when two antagonistic wires are present. The tension applied to the first tendon is T1 and the tension applied to the second tendon is T2. The friction coefficient is $\mu_1$, and the direction of the tip can be calculated with the equation $$\theta_1 = FKM(T1, T2, \mu 1) \quad (64)$$

where FKM is the forward kinematic mapping as described above. In this embodiment, the current friction coefficient, K is described as:

$$\mu = \mu_1 + \delta\mu \quad (65)$$

The direction of the tip can then be calculated with the assumption when the tendon tensions are T1 and T2 as $$\theta_2 = FKM(T1, T2, \mu_1 + \delta\mu) \quad (66)$$

The direction of the tip under the assumption of non-elongation of the tendons:

$$\theta = \lambda_1/d_1 (= \lambda_2/d_2) \quad (67)$$

is calculated based on the parallel curves characteristic. Specifically, the moment arm d1 and d2 are the opposite signed value since the two tendons locates on the opposite side on the coordinate system from Z axis. Also, λ1 and λ2 have the opposite signed values. In the two antagonistic tendon embodiment, one tendon is pulled by instance |λ1| and the second tendon is pulled in reverse by |λ2|, for a total difference in length of |λ1|+|λ2|. From this information the latest or current friction coefficient can be estimated using the equation:

$$\mu = \mu 1 + \delta\mu^*(\theta - \theta_1)/(\theta_2 - \theta_1) \quad (68)$$

In yet another embodiment, where a single tendon is embodied, the effect of tendon stretch is considered. In prior embodiments, the tendon was presumed to move without stretch. However, it has been found that elongation, or stretch of the tendon during operation can occurred. It is possible to adjust for the tendon stretch as shown herein below. Additionally, the method can be applied to other embodiments, for example, those with multiple tendons, each of which has a stretch.

In this embodiment, the apparatus is defined as having n cells, an applied tension of T, and the tendon has an elastic modulus of E. Thus, assuming a friction coefficient of $\mu_1$, the direction of the tip can be calculated with the equation (59) as in the prior embodiment where the current friction coefficient, μ is described by equation (60). Similarly, equation (61) is used to calculate $\theta_2$.

The wire stretch is then calculated:

$$dL_i = \frac{T_i}{E} \frac{L}{n} \cos\left(\frac{\theta_i}{2}\right) \quad (69)$$

where dL is defined as follows:

$$dL = \Sigma dL_i \quad (70)$$

The direction of the tip $$\theta = \frac{(\lambda - dL)}{d} \quad (71)$$

This equation is calculated based on the parallel curves characteristic where the tendon pulling displacement is calculated according to equations (69) and (70). From this information the latest or current friction coefficient can be estimated using the equation (63).

In some embodiment, it is contemplated that an angle sensor is used to detect the angle directly. This angle sensor can be located on or near the tip of the apparatus. Thus, the direction of the tip is obtained directly from the sensors instead of the equation (62) by using tendon displacement λ. The computation procedure is the same as described above except for the equation (62). Non-limiting examples of angle sensors that may be used in these embodiments are: Examples of an angle sensors are: an external magnetic field, where there is a coil at the robot tip; an external magnetic field where there is a hall effect element at the robot tip; an external magnetic field where there is a magnetic resistance element at the tip; and an angular velocity detector such as a gyro sensor.

In some embodiment, it is contemplated that a positioning sensor detecting the position directly is equipped at the tip. For these embodiments, a friction coefficient is presumed and the tip position is calculated with FKM when the tension T is applied. Instead of $\theta_1$ and $\theta_2$ as calculated above, P1 and P2 are calculated according to the following equations:

$$P1 = FKM(T, \mu_1) \quad (72)$$

$$P2 = FKM(T, \mu_1 + \delta\mu) \quad (73)$$

where P is the tip position acquired by the position sensor. Non-limiting examples of the positioning sensor are a magnetic positioning sensor, such as an Aurora positioning sensor and image analysis.

Figure 27:
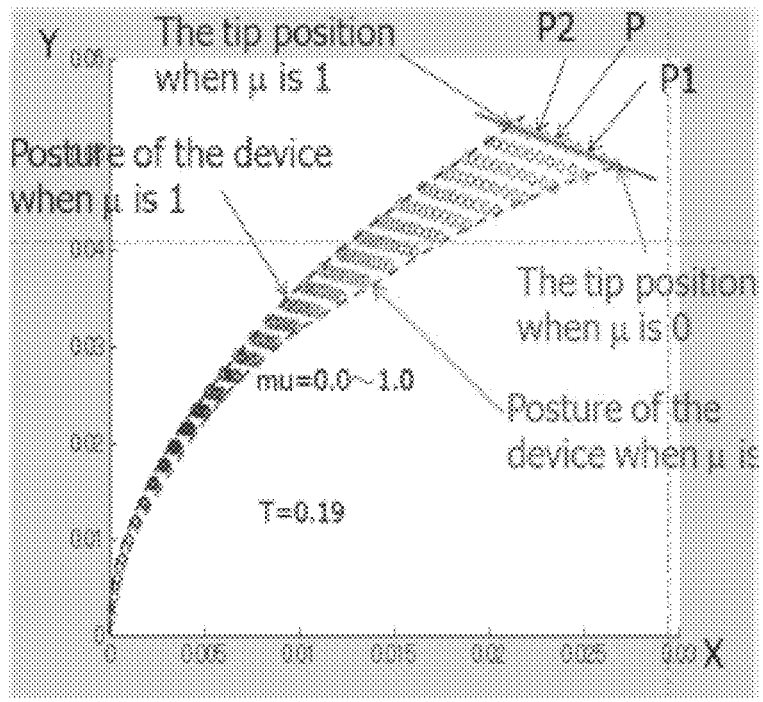
FIG. 27 is a chart providing posture of the apparatus as calculated for apparatus having different friction coefficients.

As shown in FIG. 27, the position of a continuum robot along the vertical and horizontal axes (x and Y) is shown. When T is 0.19 N, the graph shows the linear relationship between positions and a friction coefficients when a friction coefficient is changed from m=0 to m=1.0. P: The tip position detected by the position sensor. P1 is the tip position when m is assumed to be $\mu_1$ and P2 is the tip position when m is assumed to be $\mu_2$.

In some embodiments, P1, P2, and P are on the same line and P can be calculated by proportion. In other embodiments, P can be calculated by finding the nearest position on the line, which is formed by P1 and P2, to the sensed position. This can be done by first creating a line through points P1 and P2. Then, point P3 is computed on this line, where P3 is the nearest point to Point P. Then, updated μ can be computed as $$\mu = \mu 1 + \delta\mu^*(x_3 - x_1)(x_2 - x_1)(\text{or } = \mu 1 + \mu^*(z_3 - z_1)/(z_2 - z_1)) \quad (74)$$

where x1, x2 and x3 are the x position of Point P1, P2 and P3. Also z1, z2 and z3 are the z position of Point P1, P2 and P3.

Thus, some embodiments provide for the estimation of μ with sensors. Such embodiments are particularly advantageous since the system can be the robust to the internal properties, for example initial length or elasticity of tendons and the moment arm of tendons.

Some embodiments provide for the estimation of μ with tendon displacement without the integration of additional sensors on the robot. Such embodiments are particularly advantageous since the robot can be miniaturized more than a robot that requires room for such sensors and which can complicate the structure. Also, for medical application, it is preferable for sterilization to not have additional sensors, etc. Further, this feature avoids any adverse influence to the mechanical properties like stiffness or weight from the sensors.

The robots as described herein may include additional surgical tools, such as surgical tools including clamps, graspers, scissors, staplers, needle holders, and other like tools that can be used to manipulate body parts (organs or tissue) during examination or surgery. This robot may also include additional sensors or other measuring devices to, for example, aid in determining the location, posture, or other orientation of the apparatus.

In use, the multi-section continuum robot may be continuously actuated as it is moved into place inside a patient. Thus, as each division enters the patient, additional tension is added to or removed from the tendon wires to effect the desired angular displacement of the distal end of the robot as well as the angular displacement of the division(s) of the robot moving into the patient.

Therefore, the apparatus as described herein provides an apparatus that allows for improved control accuracy for determining both the angular displacement at the distal end as well as the angular displacement of each of the various divisions as the apparatus is moved through a patient. This allows for a reduction in the risk of collisions to critical anatomy and reduces the invasiveness of the surgical procedure using the apparatus as described herein.

Example 1

Figure 10C:
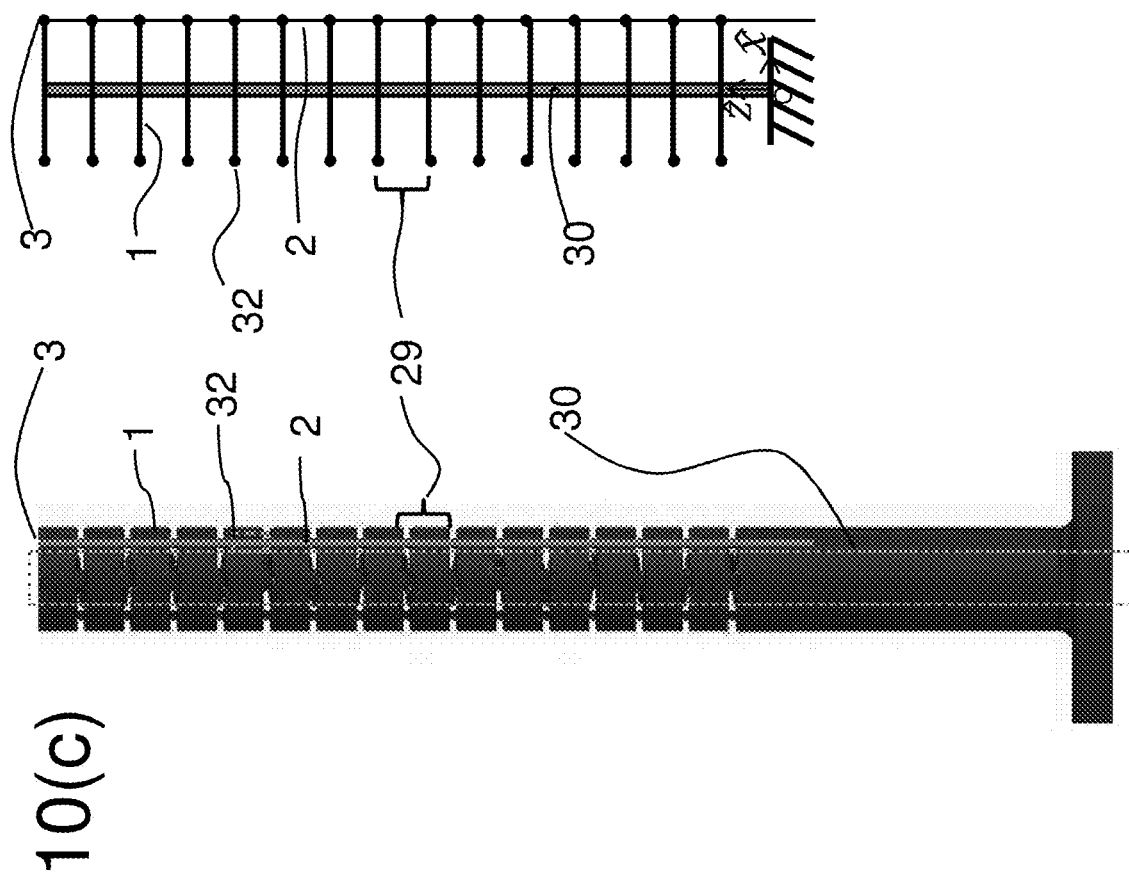
FIG. 10(c) illustrates a correspondence relationship between physical structure of the prototype and the lamped-parameter model.

To validate the lamped-parameter model, the prototype of the tendon-driven device depicted in FIGS. 10(a) and 10(b) was developed. This example has the proximal body section 1A and the distal body section 1B (FIG. 10(a)). Specifications for the prototype shown in FIG. 10 are shown below:

| | |
|---|---|
| Outer diameter of proximal and distal body segments: | 14.6 mm |
| Length of body segments (length of proximal body + length of distal body): | 208 mm |
| Length of division: | 6.95 mm |
| Number of divisions: | 30 (15 in proximal body segment and 15 in distal body segment) |
| Bending stiffness of division: | $2.7 \times 10^{-2}$ m/rad |
| Moment arm of tendons: | 5.5 mm |

FIG. 8(c) illustrates a correspondence relationship between physical structure of the example and the lamped-parameter model. The prototype has a physical structure comprising node rings that can be individually tilted and correspond with the divisions in lamped-parameter model. Hinged wire guides made of ABS polymer were stacked with a coil spring as restoring element in the body segments.

The two tendons were embedded in the prototype (FIG. 11). The tendon displacement control was performed. The input wire pull $L_{proxL}$, $L_{distR}$ as control signal were −5.4 mm, 17.4 mm. the negative value is the amount of wire feeding.

FIG. 12 illustrates validation result of the prototype. FIG. 12 shows the mean position of each division. Error bars in the figure represent the 95% t-based confidence interval among 15 measurements. The solid circles denote measured values and open circles denote predicted values by the lamped-parameter model in the control unit 8 shown in FIG. 8 with a friction coefficient μ=0.33. Additionally, previous prediction values not considering friction force are plotted in the same figure (denoted by triangles).

As can be seen in FIG. 12, the lamped-parameter model predicted the mean position of each division produces improved results over the prediction without accounting for friction.

Example 2

Figure 13A:
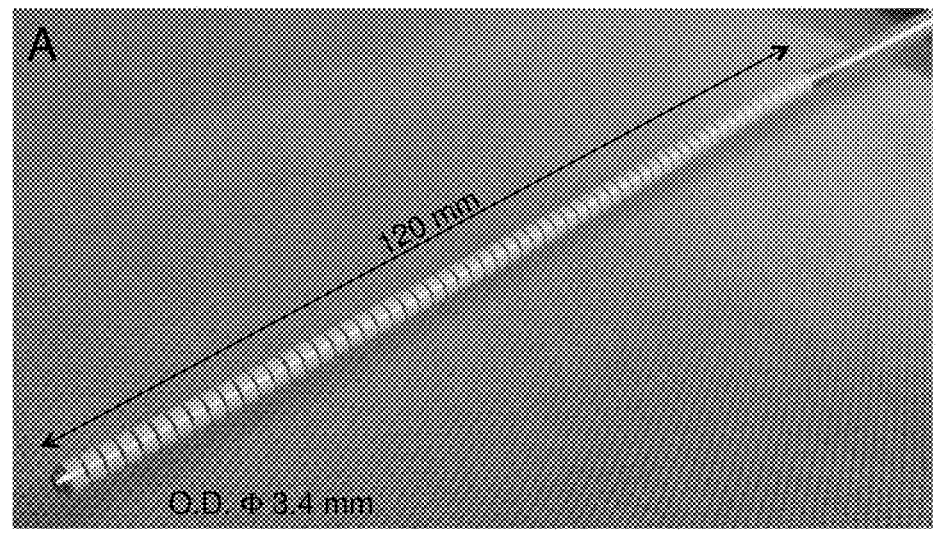
FIGS. 13(A) and 13(B) show an exemplary prototype of the tendon-driven device including a proximal body and a distal body.
Figure 13B:
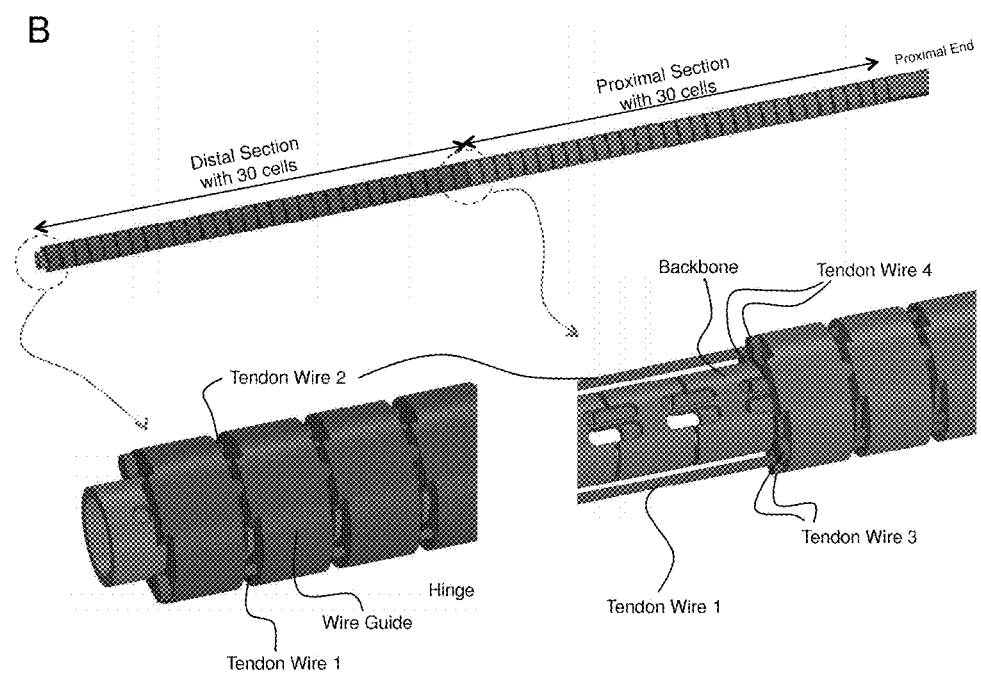

FIG. 13 shows the structure of the prototype of the continuum robot. We developed this prototype based on the teachings herein. The prototype has the outer diameter (O.D.) of 3.4 mm, a length of 120 mm and consists of two sections, each with one degree of freedom. The robot has a 1.4 mm-diameter tool channel for an imaging device. Two groups of three tendon wires run opposite each other through wire guides. The two groups of tendon wires (tendon wire 3 and 4 in FIG. 13B) start at the robot's proximal extremities and end at the robot's midpoint. The other tendon wires (tendon wire 1 and 2) start at the robot's proximal extremities and end at the distal extremities. The tendon wires are spread apart 1.4 mm from the centroid of the robot. The wire guides are made of polyether ether ketone (PEEK). The backbone is monolithically made of super elastic TiNi array (Nitinol) with leaser cutting. The hinges of wire guides are aligned to the spring feature in the backbone by stacking the wire guides without additional alignment process.

Each cell, which are the unit of linear spring system and curvature, has a length of 2 mm and a bending stiffness of $8.0 \times 10^{-3}$ Nm/rad measured after fabrication.

Example 3

Two sets of studies were conducted to assess the capability of our robot to trace the target trajectory. The first set of experiments measured the posture of one bending section robot with tension input experimentally to validate the accuracy of the FKM to the prototype. We observed the posture reached by bending and extending to assess the direction combination of tension and friction force in the model. The second set of experiments measured the accuracy of the tip position and the direction from the planned trajectory. We developed the two-sections continuum robot with a slide stage as the prismatic joint for this validation. By using the IKF, we generated the command for the prototype to trace the straight-line trajectory. We observed the tip position and direction for each commanded point. The deviation of the observed tip positions from the planed tip positions was determined followed by this observation. To validate improvement of position control accuracy with our tension propagation model, we compared this deviation with the deviation observed by the command with conventional piecewise constant curvature approximation.

Figure 18:
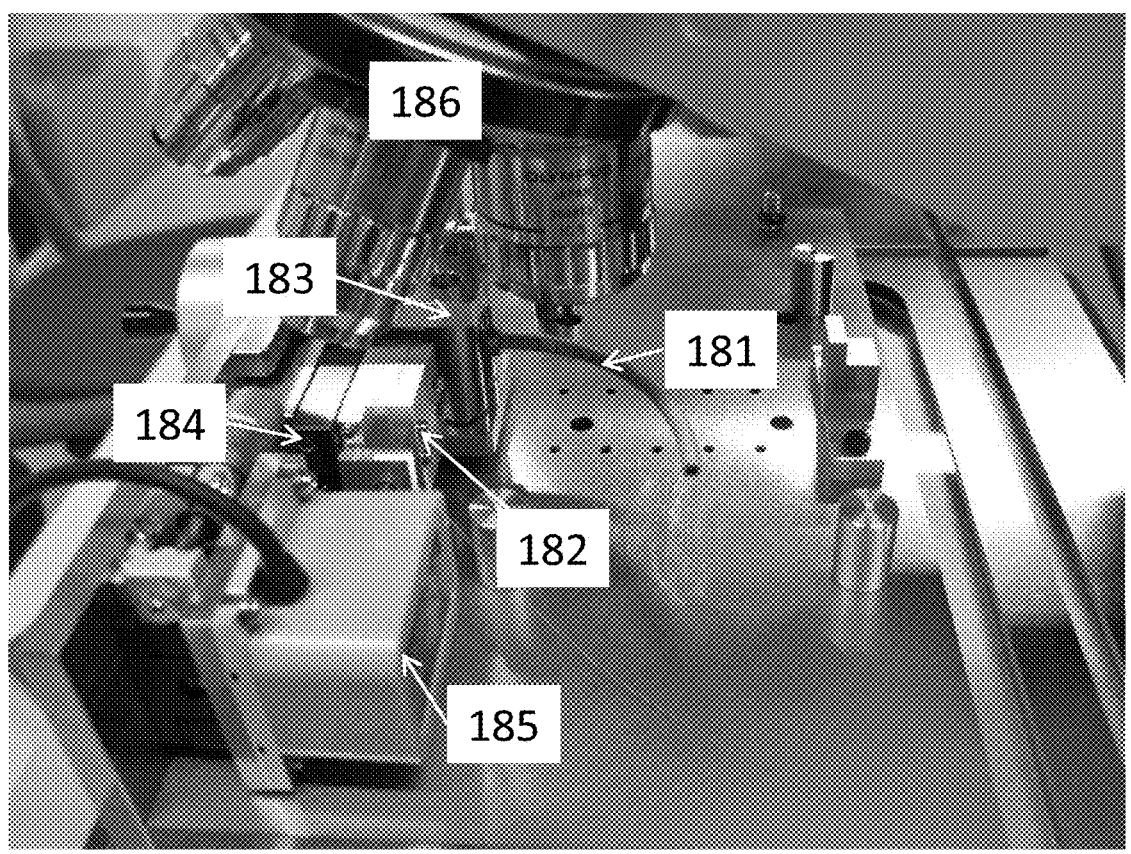
FIG. 18 is an image of an exemplary validation apparatus.

We measured the posture of one bending section with tension input to validate the tension propagation model for the prototype of the continuum robot in FIG. 13. The FIG. 18 shows the experimental apparatus for this validation. The one bending section of the continuum robot was placed with its bending plane aligned horizontally. The robot supported itself without tip draping because of the large anisotropic bending stiffness of the backbone. The tip draping was small in this experimental setting. To minimize experimental complexity, the robot has single tendon embedded on the one side (+x direction from the centroid of the robot in FIG. 14). However, robots with additional tendons can also be used following the processes as defined herein.

We performed tension control in the tendon to operate the robot. The tendon out of the robot is terminated at the tractor through the idler pulley in FIG. 18. The tractor is mounted on the slide stage and pulled by the load cell to measure the tension in tendon during actuation. We observed the posture of the robot by the microscope located above the robot. The microscope has the digitized position stage to record the position of the view. We recorded the tip position of all cells based on the feature of hinges by using this position stage.

The independent variables we set for this embodiment are tension in tendon and the bending direction for the robot. The tension is set to 0.39 N for the maximum bending angle of the section and the half value (0.18 N) of this maximum tension. The bending direction is set to direction of bending and extending with the same tension value (0.18 N) to validate the direction combination of tension and friction force in the tension propagation model. The posture measurement was conducted at three times for each tension with each bending direction. The posture data were compared to the predicted values by the FKM.

To determine if there were significant differences in prediction accuracy between the FKM we proposed and conventional PCCA, we performed paired t-test for tip-to-tip error (hereafter referred to as residual distance) of these two predictions for three tip heights. We considered differences significant at $P<0.01$.

Example 4

Figure 19A:
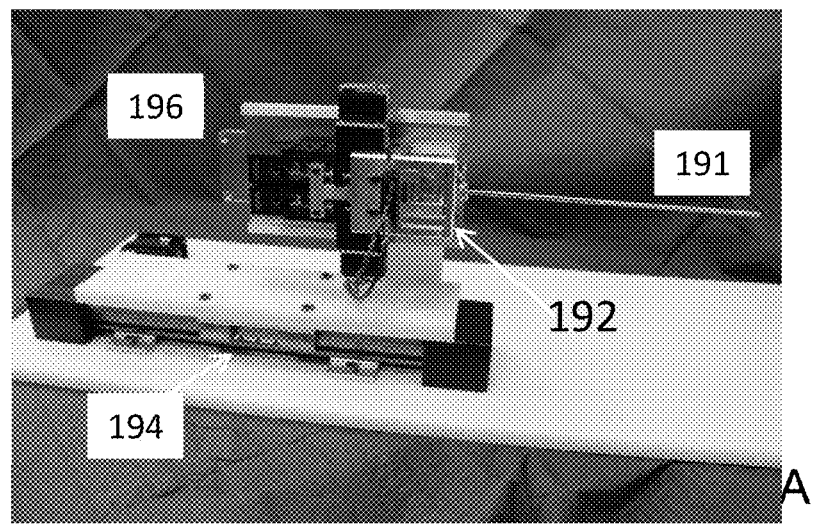
FIGS. 19(A) and 19(B) are images of an exemplary configuration tracking apparatus.
Figure 19B:
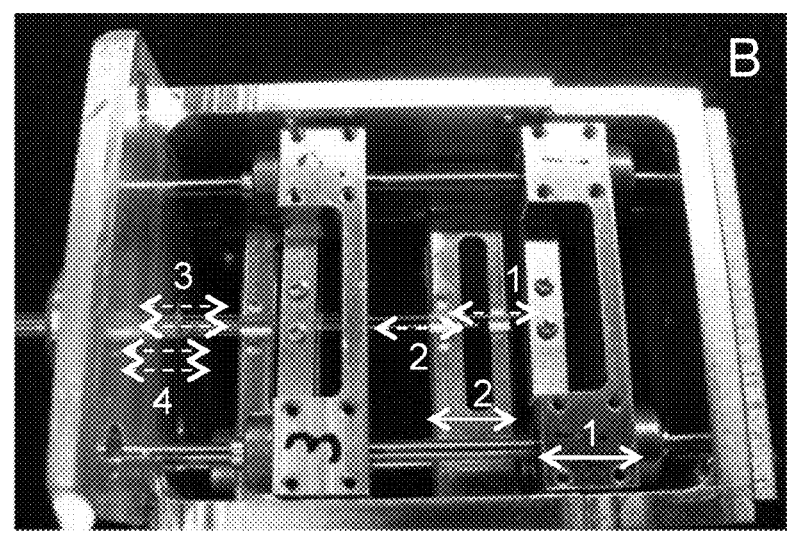
Figure 20:
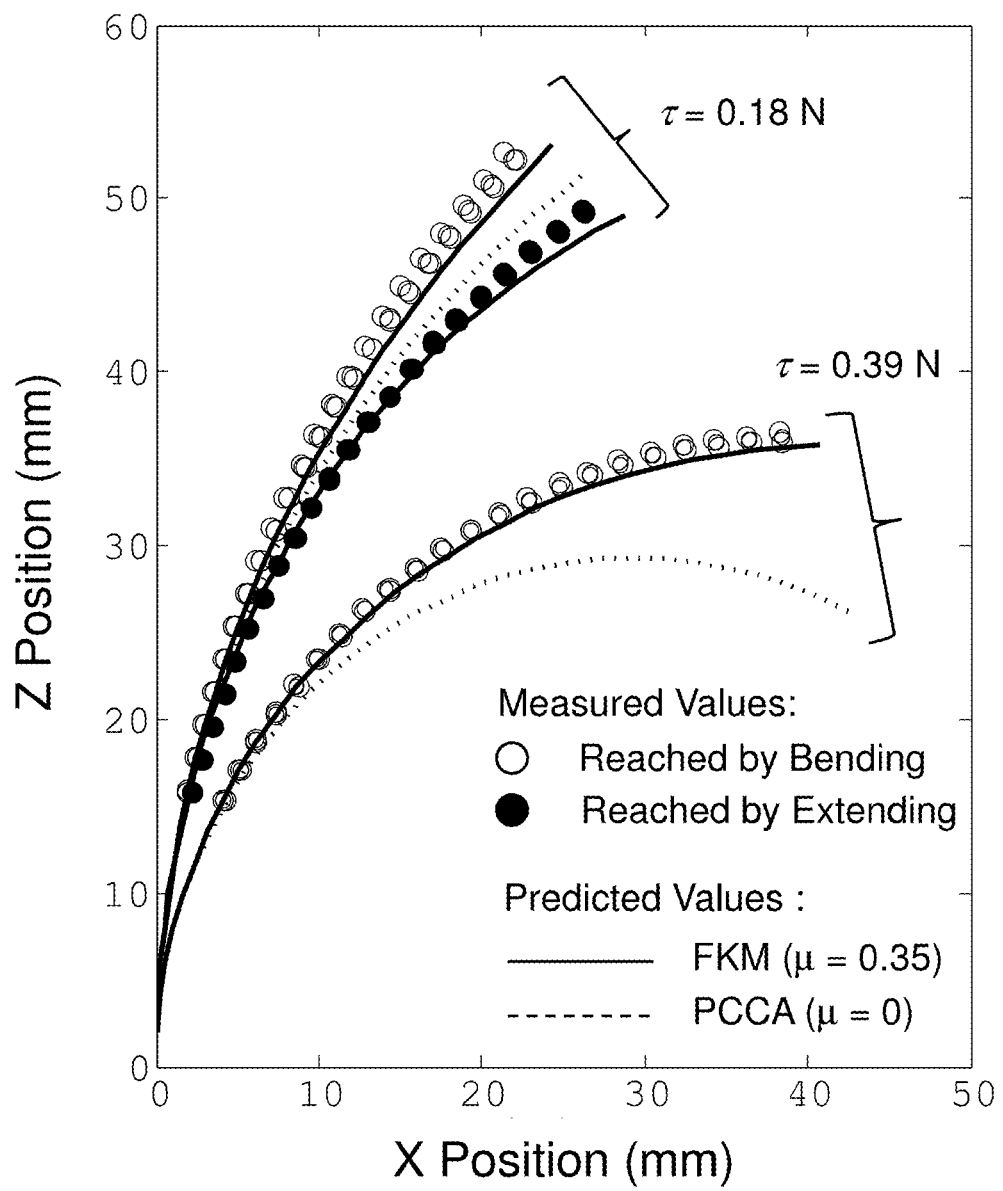
FIG. 20 is a graph showing the tracking of the line scanning trajectory.

To validate whether the robot trace the planed trajectory keeping the target tip direction, we conducted tracking of the tip positions and direction in the commanded trajectory. This is shown in FIG. 20. We developed the prototype of two-section continuum robot with a slide stage as the prismatic joint for this validation (FIG. 19). The slide stage (ZLW-1040, Igus) is motorized by the one servomotor (Dynamixel MX64, Robotis) with maximum stroke 200 mm. The continuum robot mounted on this slide stage has the actuator units to pull six tendons for two bending sections pictured in FIGS. 13(A) and 13(B). The actuator unit has the tendon tractors motorized two servomotors (FIG. 19B). These tendon tractors consists two pairs for antagonistic tendons at two bending sections. For the distal section, the tendon 1 and 2 are actuated by one pair of tractors illustrated in FIG. 19B. On the other hand, the other pair of tractors actuates the tendon 3 and 4 while the tendon 1 and 2 are penetrating through the tractors. The pair of tractors for each section is attached to a dedicated steel belt actuated by one of the servomotors to generate feeding and pulling motion by motor rotation.

To measure the tip position and direction of the prototype, we acquired a digital still photograph by a digital camera (EOS X6i, EF-S18-135 IS STM, Canon Inc.) from the top of the bending plane. We extracted the pixel position of the feature at the center of the wire guide for each cell from the photos. To determine the position with a physical metric scale, we converted these pixel position data to the metric ones based on pixel length of a known graph grid.

The independent variables we set are the target tip angle and the length of the straight-line trajectory. The target angle is set to 0 degree for forward observation and 75 degree for angled observation.

Example 5

Experimental Design of Articulation Experiment

To determine whether extending forward kinematic mapping model improves the prediction accuracy of the posture in extending from the curved shape, tendon-driven continuum robots were moved back and forth between the initial straight posture and the posture in maximum bending while observing the robot posture at the identical input tension between the arching and the extending postures. This experiment allowed direct comparison between the arching and the extending postures and determined the improved prediction accuracy for the extending posture comparing to the arching posture. Both a single tendon robot and a multiple, or antagonistic tendon robot layouts were analyzed.

The robot posture was observed loading the tension with the experimental apparatus in FIG. 18. The experiments were organized in two distinct tendon layouts in the one bending section of the robot. The first layout was a single tendon layout. In this layout, a single tendon was embedded on one portion of the robot arm with a moment arm of 1.40 mm. The single tendon layout allowed evaluation of the extended FKM with the simplest tendon layout. The second layout was an antagonistic pair of tendons. In this layout, two tendons were set on both sides with the identical moment arm of 1.40 mm. This layout evaluated the sign function of moment arm in tension propagation model which managed the direction of the friction force in tendons determined by the geometry between tendons and the bending direction of the robot.

For both tendon layouts, the initial posture of the robot was set to a substantially straight shape. The straight posture provides identical initial conditions without the hysteresis since the tendons in the straight posture are not subjected to the frictional forces. In this example, the straight posture was obtained with 0.00 N in the tendon for the single tendon layout and with (0.12, 0.12) N for the antagonistic tendon layout, which were 0.12 N for the tendon embedded on the −x and +x direction from the centroid of the robot.

The posture was measured with multiple input tensions to evaluate the extended FKM over the articulation range of the robot. The input tensions were set from 0.10 N to 0.40 N at 0.10 N intervals for the single tendon, (0.12, 0.24) N and (0.12, 0.48) N for the antagonistic tendon. After setting the straight posture, the tension in tendons was increased to these values in a series. We measured the posture with these ascending tensions as the arching postures. After completion of the measurement for the arching postures, we increased the input tension to 0.55 N for the single tendon layout and (0.12, 0.65) N for the antagonistic tendon layout as the posture in maximum bending. This posture was a halfway point for the articulation experiment and was followed by the measurement of an extending posture. We decreased the input tension from 0.40 N to 0.10 N at 0.10 N intervals for the single tendon layout and (0.12 0.48) N to (0.12, 0.24) N for the antagonistic tendon layout. We measured the posture with these descending tensions as the extending posture.

In all posture measurement, we measured the position of thirty hinges of the robot as well as the tip of the robot, and determined the position of thirty cells by calculating middle points between adjoining hinges or the hinge and the tip. We performed three trials for the arching and the extending postures with each tendon layout. We recorded the one posture for every input tension in one trial.

To determine whether the prediction accuracy of the posture improved in the extended FKM from the FKM, we calculated the position errors of all sets of cells for both the extended FKM and the FKM, which is distance of all sets of cell positions between the measured and predicted values. The position errors are summarized as mean values of the three trials and were compared with the target error of 5 mm.

The friction coefficient for the computation was 0.33. This friction coefficient was determined experimentally. We measured angle of friction with the tendon wire and the wire guide of the robot. The wire guide hanging on the tendon wire was rotated by a manual rotational stage until it slipped on the tendon wire. Specifically, to get the appropriate contact between the tendon wire and the eyelets in the wire guide, we attached a weight of 1.5 grams on the wire guide during the measurement. Twenty trials were conducted for the measurement, and the friction coefficient was measured to be µ=0.33±0.07 (standard deviation).

FIG. 18 provides the experimental apparatus used for the articulation experiment. The one section of the tendon-driven continuum robot was positioned with its bending plane aligned horizontally, and supported its articulation posture by itself. The tendon was fixed to the tractor through the idler pulley. The tractor was mounted on the slide stage and pulled with the load cell (LTS-2KA, Kyowa Electronic Instruments) that connected to the signal conditioner (CDV-700A, Kyowa Electronic Instruments) to measure the tension in the tendon during actuation. The posture of the robot was observed with the measurement microscope (STM-UM, Olympus). The digitized position stage in the microscope recorded the position of the hinges as the posture. For the antagonistic tendon layout, we used a weight to apply gravitational forces on the tendon on the other side from the load cell (−x direction from the centroid of the robot). The weight was hanged on the end of tendons via idler pulleys to pull the tendon horizontally.

Hysteresis of Extending Postures.

Figure 30A:
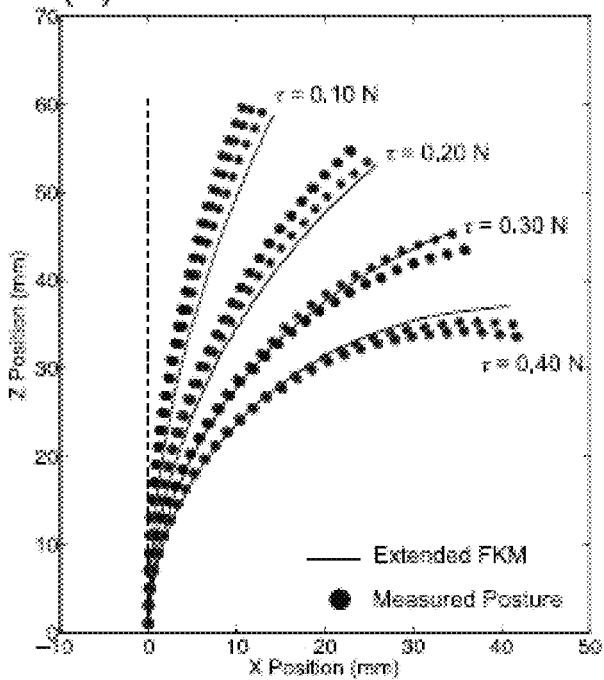
FIGS. 30(a) and 30(b) are charts showing calculated vs measured postures for tensions between 0.10 and 0.40 N for extending postures (FIG. 30(a)) and arching postures (FIG. 30(b)) for the single tendon layout.
Figure 30B:
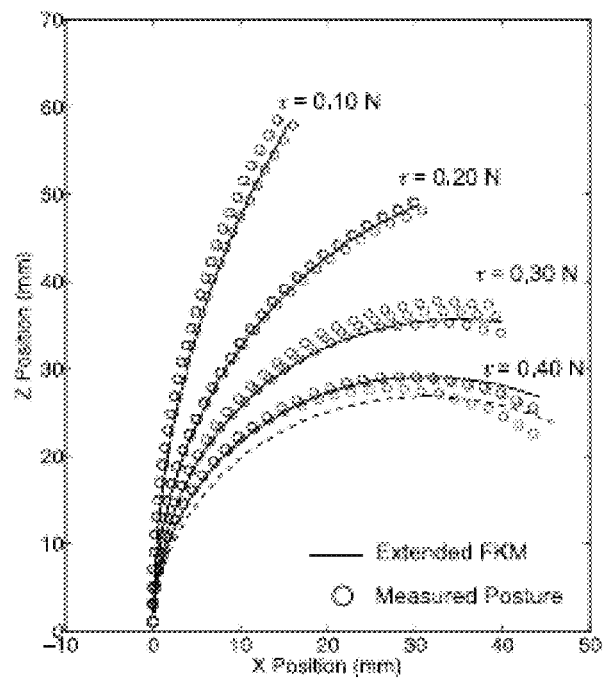
Figure 31A:
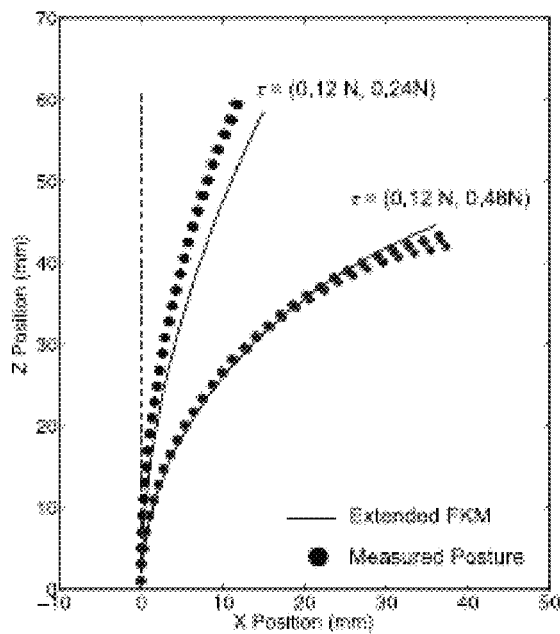
FIGS. 31(a) and 31(b) are charts showing calculated vs measured postures for tensions between 0.12N and −0.24 N and 0.12 N and 0.48 N for extending postures (FIG. 31(a)) and arching postures (FIG. 31 (b))
Figure 31B:
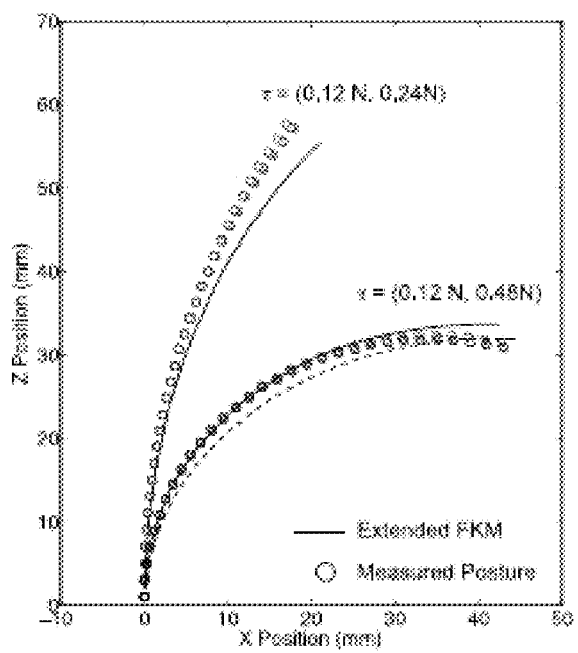

The extending postures at every input tension performed the larger bending than the arching posture at the same input tension for the single and the antagonistic tendon layout (FIGS. 30(a) and 30(b) in the single tendon layout, FIG. 31 in the antagonistic tendon layout). This hysteretic tendency of the extending postures was identical to in the extending postures predicted by the extended FKM. The mean discrepancy of the tip position of the extending posture from the arching postures were 9.84 mm at 0.4 N for the single tendon and 13.20 mm at (0.12, 0.48) N for the antagonistic tendon.

Position Errors of the Extended FKM.

Through the arching and the extending posture with the single and the antagonistic tendon layout, the extended FKM predicted the measured posture within the target position error of 5 mm (2.89 mm at maximum for the single tendon (FIG. 33) and 3.87 mm at maximum for the antagonistic tendon layout (FIG. 35)). In all experimental conditions, we observed the maximum position error at the most distal cell, which is Cell 30.

Figure 32A:
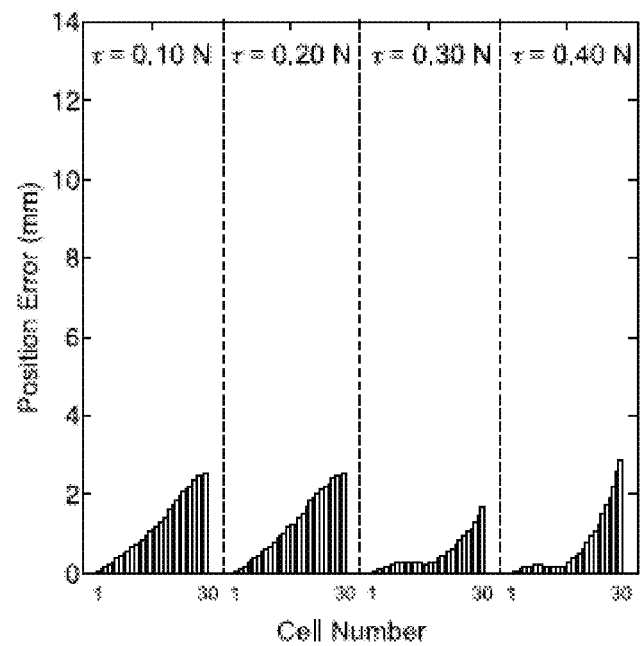
FIGS. 32(a) and 32(b) are charts showing the position error of the FKM in mm for each of the 30 cells within an embodied snake robot for tensions between 0.10 N and 0.40 N. The bars signify the mean values of the position error among three trials.
Figure 32B:
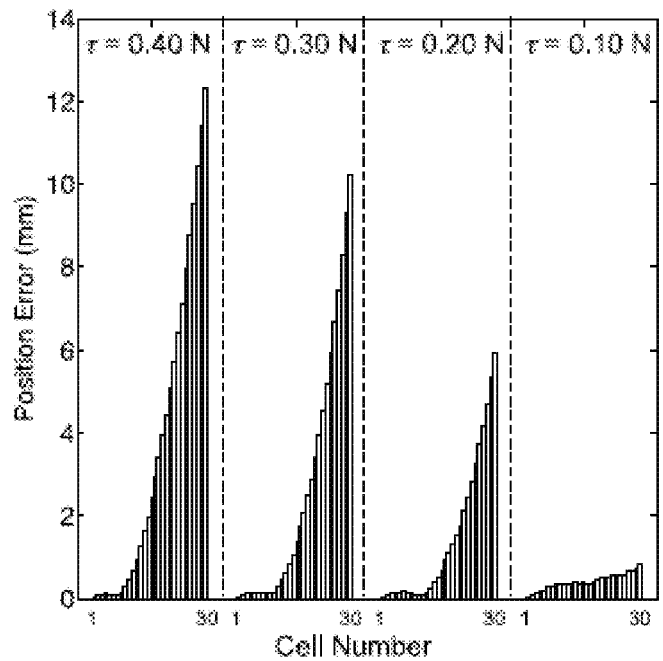
Figure 34A:
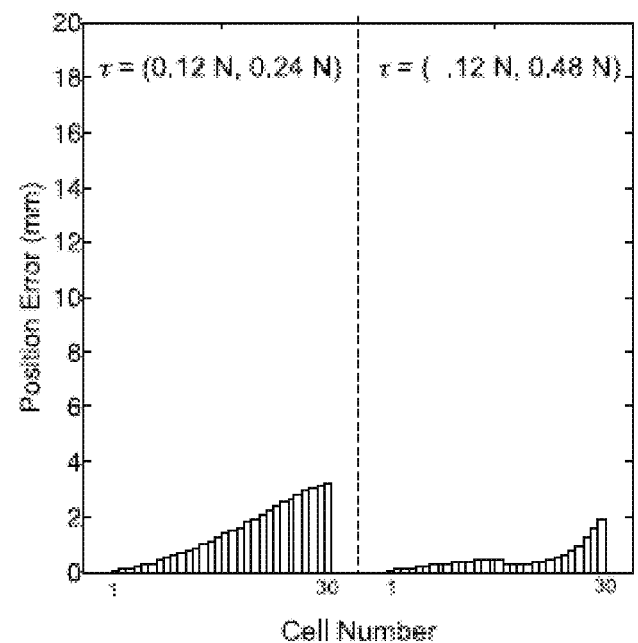
FIGS. 34(a) and 34(b) are charts showing the result of position error of the FKM for the antagonistic tendon layout. The position errors of a set of all cells were plotted. The bars signify the mean values of the position error among three trials.

Similarly, with the FKM, the maximum position error was the error at the most distal cell, but the maximum position error was more than two times larger than the target error of 5 mm. (12.36 mm for the single tendon layout (FIG. 32), 14.67 mm for the antagonistic tendon layout (FIG. 34).

Particularly, in comparison between the extended FKM and the FKM, the position error of the extending posture with the extended FKM was 81% lower than with the FKM for the single tendon layout and 74% lower for the antagonistic tendon layout (2.38 mm vs. 12.36 mm for the single tendon, 3.87 mm vs. 14.67 mm for the antagonistic tendon layout). These improved position error of the extending posture contributed the consistent lower value than the target error for the arching and the extending posture with the extended FKM.

FIGS. 30(a) and 30 (b). Result of the articulation experiment with the single tendon layout. The posture with a dotted line signifies the initial posture for each measurement. [Top] arching posture: the measured posture (black circles) was performed from the straight initial posture, [Bottom] extending posture: the measured posture (white circles) was performed from the initial posture in maximum bending of the robot. Y FIGS. 31 (a) and 31(b). Result of the articulation experiment with the antagonistic tendon layout. The posture with a dotted line signifies the initial posture for each measurement. [Top] arching posture: the measured posture (black circles) was performed from the straight initial posture, [Bottom] extending posture: the measured posture (white circles) was performed from the initial posture in maximum bending of the robot FIGS. 32(as) and 32(b). Result of the position error of the FKM for the single tendon layout. The position errors of a set of all cells were plotted. The bars signify the mean values of the position error among three trials. (Top) arching posture, (Bottom) extending posture.

Figure 33A:
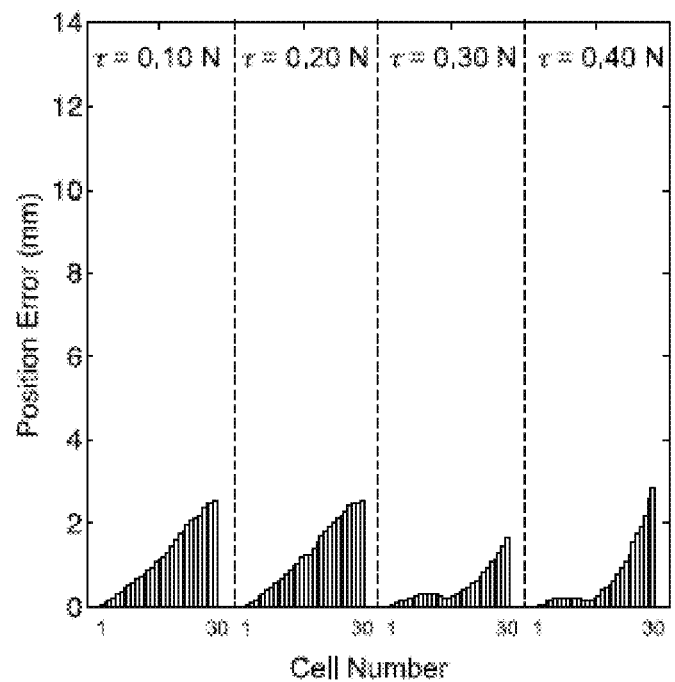
FIG. 33(a) is the arching posture.
Figure 33B:
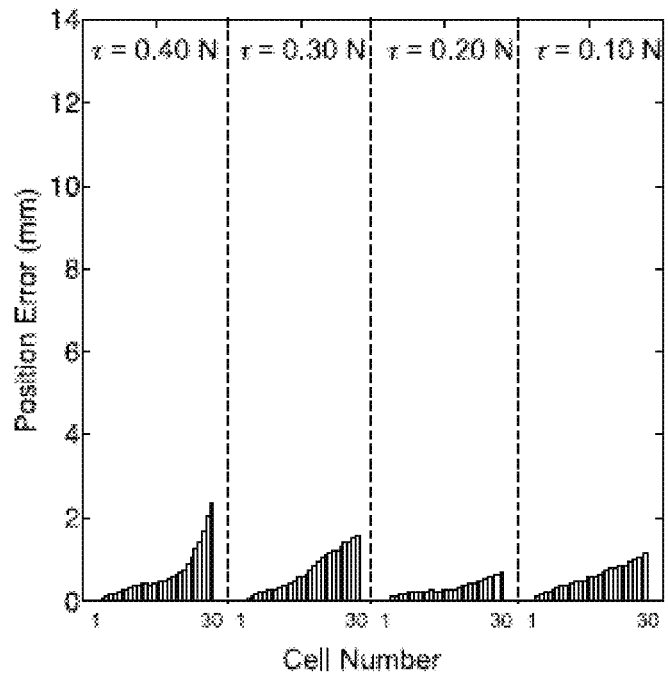
FIG. 33(b) is the extending posture.

FIGS. 33(as) and 33(b). Result of position error of the extended FKM for the single tendon layout. The position errors of a set of all cells were plotted. The bars signify the mean values of the position error among three trials. (Top) arching posture, (Bottom) extending posture.

Figure 34B:
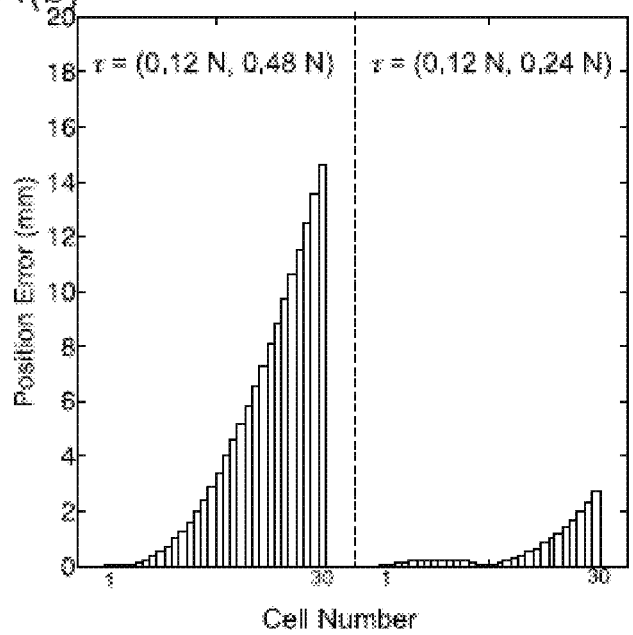

FIGS. 34(s) and 34(b). Result of position error of the FKM for the antagonistic tendon layout. The position errors of a set of all cells were plotted. The bars signify the mean values of the position error among three trials. (Top) arching posture, (Bottom) extending posture.

Figure 35A:
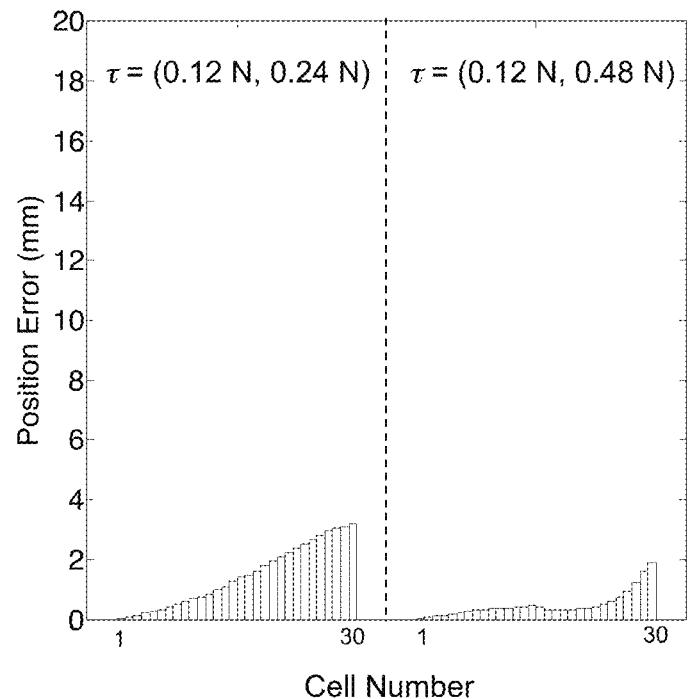
FIGS. 35(a) and 35(b) provide results of position error of the FKM for the antagonistic tendon layout. The position errors of the sets of all cells were plotted. The bars signify the mean values of the position error among three trials. (Top) arching posture, (Bottom) extending posture.
Figure 35B:
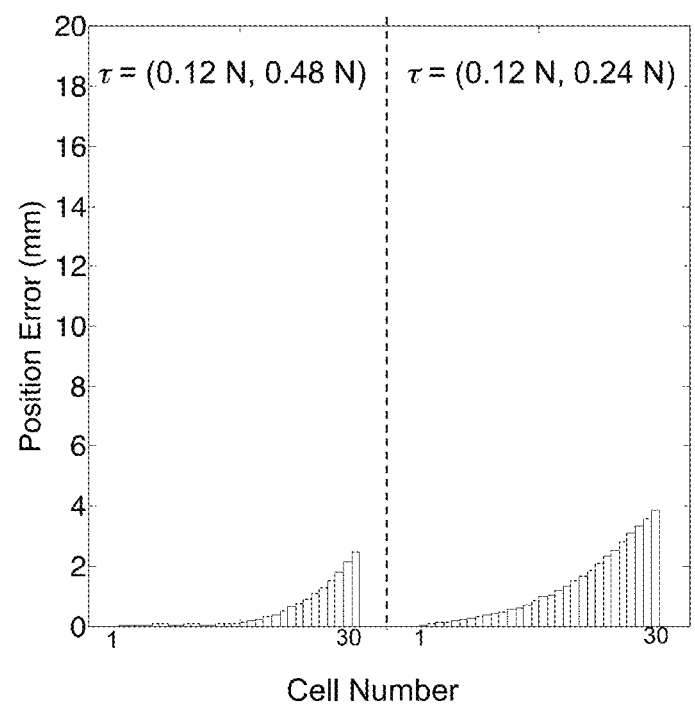

FIGS. 35(as) and 35(b). Result of position error of the FKM for the antagonistic tendon layout. The position errors of a sets of all cells were plotted. The bars signify the mean values of the position error among three trials. (Top) arching posture, (Bottom) extending posture.

This example presented the tendon-driven continuum robot for neuroendoscopy. We also proposed the extended FKM incorporating the tension propagation model to compute the hysteresis operation of the robot. The extended FKM characterized the hysteresis operation by coupling from the robot's posture at the previous time. We experimentally evaluated the prediction accuracy of the hysteresis operation by the extended FKM and compared the position error between the measured and the prediction posture by the extended FKM and the FKM. Our result indicated that the extended FKM predicted the measured posture within the target position error of 5 mm (2.89 mm for the single tendon 3.87 mm for the antagonistic tendon layout). We also found that the extended FKM helped to increase the prediction accuracy for the extending posture over the FKM (81 and 74% decrease for the single and the antagonistic tendon layout). Since the hysteresis operation appears in any maneuvers of neuroendoscopy, our extended FKM is useful for improving control accuracy of the robot for the maneuvers of neuroendoscopes.

In the articulation experiment, the extended FKM tended to predict larger bending angles for a set of cells of the robot than the measured values at the low tension and smaller bending angles at the high tension. This tendency was consistent in the arching and the extending posture for any tendon layouts. Therefore, the discrepancy between the extended FKM-predicted and measured values results from some factors of conservative quantity instead of the hysteresis quantity. We expected that this factor was probably the nonlinearity of the spring constant of the backbone, which the extended FKM does not take into account. Since the backbone was made of Nitinol, the young's modulus might show the soft spring effect. We also expect that the mechanical design of the backbone is helpful to reduce this unpleasant nonlinearity and to develop the robot with suitable control.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An apparatus comprising:
   a tendon-driven device having a proximal end fixed mechanically and a distal end, comprising:
   a bendable body, and
   a tendon attached to and extending a length of said bendable body,
   wherein multiple divisions can be described on said tendon-driven device between said distal end and said proximal end;
   an actuator connected to said tendon, configured to actuate said tendon based on a control signal; and
   a controller configured to send said control signal to said actuator for actuating said tendon based on the control signal, comprising a kinematic mapping unit that provides an estimate of angular displacement prior to actuation by the actuator, wherein the kinematic-mapping unit is configured for:
   iteratively calculating tension values for the multiple divisions of the device from the proximal to distal end,
   estimating an angular displacement at the distal end of said tendon-driven device using said tension values,
   propagating a tension ratio between adjacent divisions of said tendon-driven device from the tension of the more proximally located division, the tension ratio generated from information of friction between said tendon and said division and angular displacements of the adjacent divisions; and
   estimating the angular displacement in said divisions from said tension ratios,
   wherein the tension ratios between at least one adjacent division of said tendon-driven device vary to account for friction between said tendon and said division and angular displacements of the adjacent divisions,
   wherein the iterative calculation of tension values, estimating of angular displacement, propagating of tension ratio, and estimating of angular displacement is employed by the controller to actuate the tendon-driven device.

2. The apparatus of claim 1, further comprising mapping tension to curvature for a first division at the proximal end of said tendon-driven device from information of friction between said tendon and said first division and angular displacement of said first division.

3. The apparatus of claim 1, wherein said control signal actuating said tendon based on a control signal provides a tendon length.

4. The apparatus of claim 1, wherein said tendon-driven device further comprises a surgical assisting tool located in a tool channel in said bendable body.

5. The apparatus of claim 4, wherein said surgical assisting tool is an endoscope.

6. The apparatus of claim 1, wherein at least 30 equal divisions are described between said distal end and said proximal end of said tendon-driven device.

7. The apparatus of claim 1, wherein said controller further comprising a memory unit storing said estimations of angular displacement in divisions,
   wherein said tension ratio is changed in accordance with said estimations stored in said memory unit at a previous time.

8. The apparatus of claim 1, wherein there are a plurality of tendons in said tendon-driven device, and wherein said tension ratios form a matrix and the matrix elements of said tension ratio are calculated using information of friction between said tendons and said body.

9. The apparatus of claim 8,
   wherein said tension ratio for computation of said tension in tendon from 1 to m in division i is described by the matrix $$A_i = \begin{bmatrix} \alpha_{i,1}^k & & & & 0 \\ & \ddots & & & \\ & & \alpha_{i,j}^k & & \\ & & & \ddots & \\ 0 & & & & \alpha_{i,m}^k \end{bmatrix}$$

where $$\alpha_{i,j}^k = \frac{\tau_{i+1,j}^k}{\tau_{i,j}^k} = \left( \frac{1 - \mu \sin(|\theta_i^k|/2)}{1 + \mu \sin(|\theta_i^k|/2)} \right)^{sgn(d_{i,j})sgn(\theta_i^k - \theta_i^{k-1})}$$

$\theta_i^k$ is said estimation of angular displacement in division i at time k,
$\theta_i^{k-1}$ is said estimation of angular displacement in division i at time k−1,
μ is a friction coefficient between said tendon and said hole as said information of friction, and
$d_j$ is signed scalar of distance from centroid of said body to said tendon j at said positions of said tendons.

10. The apparatus of claim 1,
    wherein said bendable body comprises a plurality of body segments connected serially from said proximal end to said distal end of the tension-driven device, wherein at least one tendon is attached and extends the length each of the plurality of body segments.

11. The apparatus of claim 10, comprising two body segments, at least four tendons.

12. The apparatus of claim 1,
    wherein said tension ratio for computation of said tension in division i is described by the equation $$\left( \frac{1 - \mu \sin(\hat{\theta}_i^k/2)}{1 + \mu \sin(\hat{\theta}_i^k/2)} \right)$$

where
$\hat{\theta}_i^k$ is said estimation of angular displacement in division i at time k, and
μ is a friction coefficient between said tendon and said hole as said information of friction.

13. The apparatus of claim 1,
    wherein said tension ratio for computation of said tension in division i is described by the equation $$\left( \frac{1 - \mu(\hat{\theta}_i^k/2)}{1 + \mu(\hat{\theta}_i^k/2)} \right)$$

where
$\hat{\theta}_i^k$ is said estimation of angular displacement in division i at time k, and
μ is a friction coefficient between said tendon and said hole as said information of friction.

14. The apparatus of claim 1, wherein the tension of the tendon to obtain a desired angular displacement at the distal end of said tendon-driven device is calculated using a polynomial equation, a quadratic equation, or an exponential equation.

15. The apparatus of claim 1, wherein the tension of the tendon to obtain a desired angular displacement at the distal end of said tendon-driven device is controlled by values from a tabulated value.

16. The apparatus of claim 1, wherein said controller further comprises:
   an initial-value-generating unit capable of computing an angular displacement and a tension in said tendon at the proximal end from a control target;
   an adding unit capable of computing a difference between said control target and said estimations of angular displacement at the distal end;
   a checking unit capable of generating an activate signal if said difference is smaller than a convergence criterion; and
   a switch unit.

17. The apparatus of claim 16, wherein the switch unit is capable of sending said tension at said proximal end as said control signal to said actuator based on said activate signal from said checking unit.

18. The apparatus of claim 16, wherein the switch unit is capable of sending said estimations of angular displacement in said divisions to a tendon-displacement-computing unit based on said activate signal from said checking unit, said tendon-displacement-computing unit computing tendon displacement based on said estimations of angular displacement in said divisions and sending said tendon displacement to said actuator as said control signal.

19. The apparatus of claim 16, wherein said controller further comprises:
   a feedback-control unit capable of computing a compensation signal from a compensation-input signal;
   a compensation-adding unit capable of generating said control signal by adding said compensation signal to said tension at proximal end from said switch unit; and
   a feedback-adding unit capable of generating said compensation-input signal from a deviation of said angular displacement of said body from said control target.

20. An endoscopic apparatus comprising,
   a tendon-driven device having a proximal end fixed mechanically and a distal end, comprising:
      a bendable body having at least one tool channel,
      surgical assisting tool within said tool channel, and
      a tendon attached to and extending a length of said body,
      wherein multiple divisions can be described on said tendon-driven device between said distal end and said proximal end;
   an actuator connected to said tendon, configured to actuate said tendon based on a control signal; and
   a controller sending said control signal to said actuator, comprising,
      a kinematic-mapping unit computing estimations of an angular displacement at the distal end prior to advancement of the bendable body,
      wherein said kinematic-mapping unit defines divisions on said tendon-driven device along an extending direction of said tendon for computing said estimations,
      wherein said kinematic mapping unit computes estimations of an angular displacement on a distal side from estimations of a tension in said division on a proximal side combining with an iteratively calculated tension ratio for the multiple divisions of the device from the proximal to distal end,
      wherein said kinematic mapping unit propagates a tension ratio between adjacent divisions of said tendon-driven device from the tension of the more proximally located division and from information of friction between said tendon and said division and angular displacements of the adjacent divisions;
      wherein said kinematic mapping unit estimates the angular displacement in said divisions from said tension ratios,
      wherein said tension ratio is changed in accordance with said estimations of angular displacement in division on said proximal side, and
      wherein the tension ratios between at least one adjacent division of said tendon-driven device vary to account for friction between said tendon and said division and angular displacements of the adjacent divisions,
   wherein the iterative calculation of tension values, estimating of angular displacement, propagating of tension ratio, and estimating of angular displacement is employed by the controller to actuate the tendon-driven device.

21. The apparatus of claim 1, wherein the kinematic-mapping unit further comprises a computing unit configured to compute at least one of:
   angle and reactive force between adjacent divisions of the tendon-driven device,
   a tensile force of the tendon, and
   a frictional force and a normal force of a tendon and a division,
based on an angle and a reactive force of a certain division, and tensile force of a corresponding tendon.

22. The apparatus of claim 21,
   wherein the computing unit computes at least one of angle of adjacent divisions, reactive force, tensile force of the corresponding tendon, frictional force of the tendon and division, and normal force, using an iterative calculation.

23. The apparatus of claim 1, wherein the kinematic-mapping unit is further configured for calculating adjacent angular displacement based on an angle and reactive force of a n division of the tendon-driven device and calculating tensile force of a corresponding tendon, and wherein the apparatus further comprises a switching unit configured to switch between calculating angular displacement and adjacent angular displacement.

24. The apparatus of claim 1, wherein the controller updates the information of friction between the tendon and the body over time.

25. The apparatus of claim 1, wherein the tension values of the multiple divisions of the device are calculated by incorporating information relating to the friction between the divisions.

* * * * *